United States Patent
Olive et al.

(10) Patent No.: US 10,716,838 B2
(45) Date of Patent: Jul. 21, 2020

(54) ANTI-CD277 ANTIBODIES

(71) Applicants: Daniel Olive, Marseilles (FR); Marc Bonneville, Nantes (FR); Emmanuel Scotet, Nantes (FR); Christelle Harly, Nantes (FR); Yves Guillaume, Marseilles (FR)

(72) Inventors: Daniel Olive, Marseilles (FR); Marc Bonneville, Nantes (FR); Emmanuel Scotet, Nantes (FR); Christelle Harly, Nantes (FR); Yves Guillaume, Marseilles (FR)

(73) Assignees: INSERM (INSTITUT NATIONAL DE LA SANTE ET DE LA RECHERCHE MEDICALE), Paris (FR); INSTITUT JEAN PAOLI & IRENE CALMETTES, Marseilles (FR); UNIVERSITE D'AIX MARSEILLE, Marseilles (FR); UNIVERSITE DE NANTES, Nantes (FR); CENTRE NATIONAL DE LA RECHERCHE SCIENTIFIQUE—CNRS, Paris (FR)

( * ) Notice: Subject to any disclaimer, the term of this patent is extended or adjusted under 35 U.S.C. 154(b) by 0 days.

(21) Appl. No.: 16/282,733

(22) Filed: Feb. 22, 2019

(65) Prior Publication Data
US 2019/0201513 A1    Jul. 4, 2019

Related U.S. Application Data

(63) Continuation of application No. 14/791,528, filed on Jul. 6, 2015, now abandoned, which is a continuation-in-part of application No. 13/994,277, filed as application No. PCT/EP2011/072787 on Dec. 14, 2011, now abandoned.

(30) Foreign Application Priority Data

Dec. 15, 2010    (WO) .................. PCT/IB2010/003417

(51) Int. Cl.
*A61K 39/395*    (2006.01)
*C07K 16/28*    (2006.01)
*A61K 39/00*    (2006.01)

(52) U.S. Cl.
CPC ...... *A61K 39/0011* (2013.01); *C07K 16/2818* (2013.01); *C07K 16/2827* (2013.01); *A61K 39/00* (2013.01); *C07K 2317/55* (2013.01); *C07K 2317/74* (2013.01); *C07K 2317/75* (2013.01)

(58) Field of Classification Search
None
See application file for complete search history.

(56) References Cited

FOREIGN PATENT DOCUMENTS

WO    WO-2012080351 A1 *    6/2012    ......... C07K 16/2818

OTHER PUBLICATIONS

Connote et al., Eur. J. Immunol. 34: 2089-2099 (2004). (Year: 2004).*

* cited by examiner

*Primary Examiner* — Phillip Gambel
(74) *Attorney, Agent, or Firm* — W&C IP

(57) ABSTRACT

Described herein are anti-CD277 antibodies which: activates or inhibit the cytolytic function of Vγ9/Vδ2 T cells, and/or costimulates T cells together with CD3-TCR, and/or costimulates T cells in addition to CD28-B7 costimulation, and/or increases the activity and/or survival of monocytes and dendritic cells. The use of said antibodies in therapy is also described.

Figure 1A:
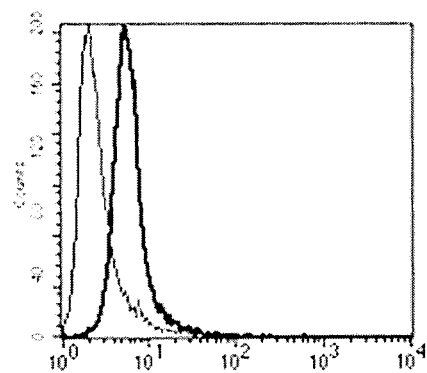

12 Claims, 16 Drawing Sheets
Specification includes a Sequence Listing.

Monocytes iDC anti-BT3 mAb
(clone 20.1)

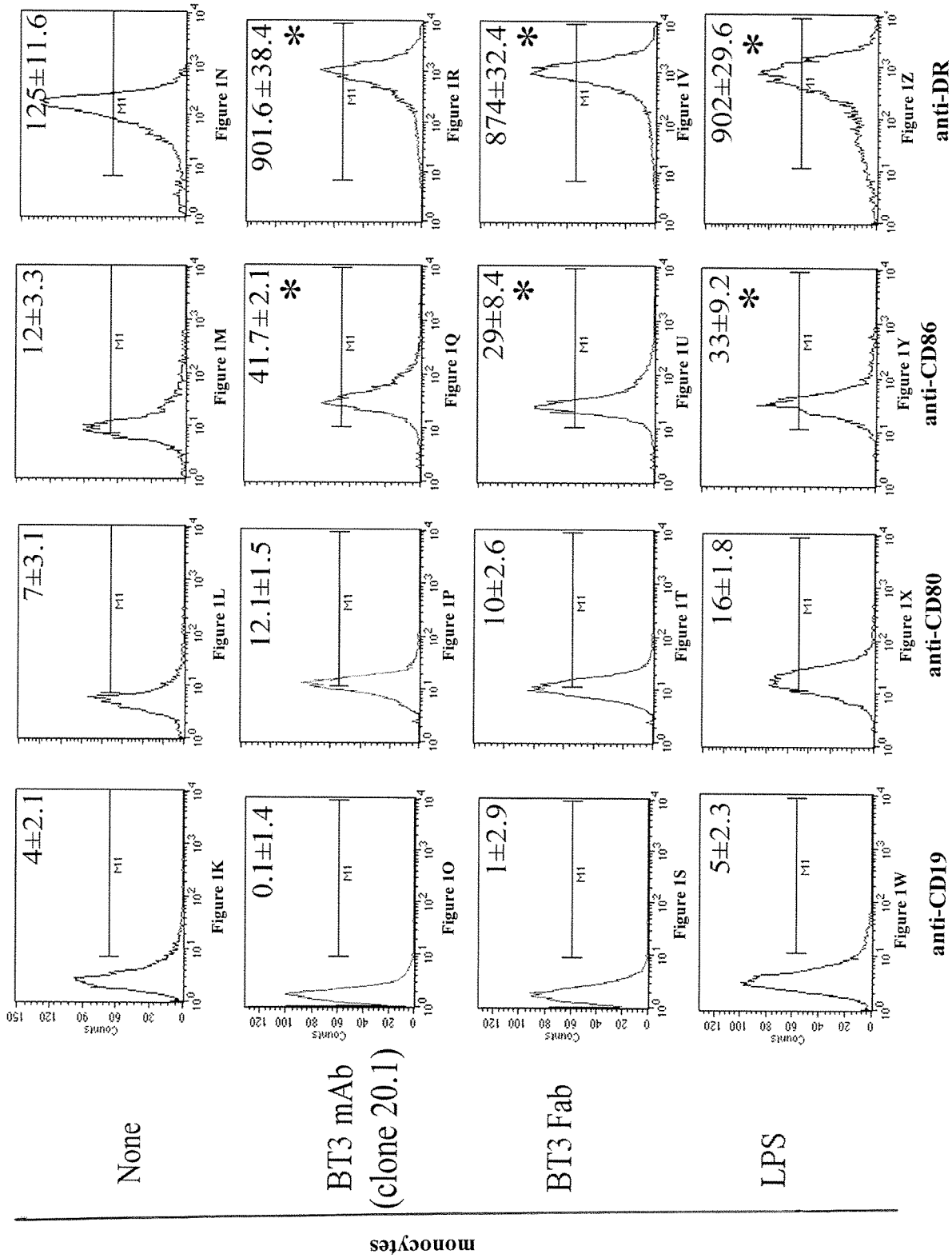

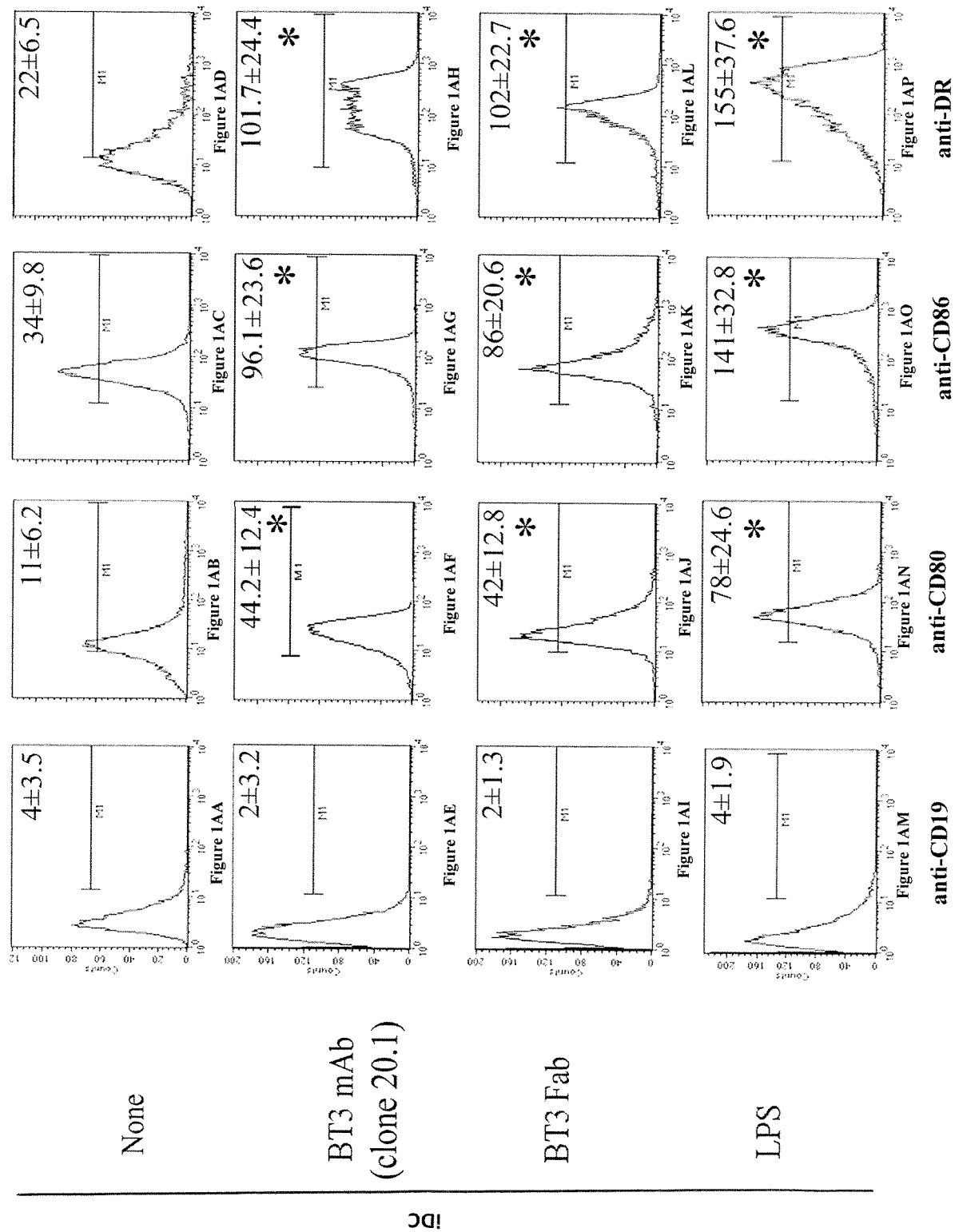

A

B

C

ANTI-CD277 ANTIBODIES

CROSS REFERENCE TO RELATED APPLICATIONS

The present application is a continuation application of U.S. patent application Ser. No. 14/791,528 filed on Jul. 6, 2015, which itself was a continuation-in-part of U.S. patent application Ser. No. 13/994,277 filed Sep. 24, 2013, which is a 371 national stage application based on PCT/EP2011/072787 filed Dec. 14, 2011, which claims priority to International Patent Application No. PCT/IB2010/003417 filed on Dec. 15, 2010, which is incorporated herein by reference in its entirety.

FIELD OF THE INVENTION

The invention relates to anti-CD277 antibodies and uses thereof.

BACKGROUND OF THE INVENTION

White blood cells are cells of the immune system involved in defending the body against pathogens. Among these cells, lymphocytes, monocytes, and dendritic cells can be cited. Monocytes may migrate from the bloodstream to other tissues and differentiate into tissue resident macrophages or dendritic cells. Dendritic cells play a role as antigen presenting cells (APC) that activate lymphocytes. Among lymphocytes, T cells can be divided into γδ T cells and αβ T cells.

Vγ9/Vδ2 T cells are important effectors of the immune defense. They lyse directly pathogen infected or abnormal cells. In addition, they regulate immune responses by inducing dendritic cell (DC) maturation as well as the isotypic switching and immunoglobulin production. This important cell platform of the immune system is strictly regulated by surface receptors, chemokines and cytokines.

The priming of T cells is modulated by involvement of specialised cells and secretion of chemotactic cytokines. Nowadays, we know that T-cell activation is the result of two synergistic events. The first is the interaction between the receptor of T cell (TCR) and the major histocompatibility complex (MHC) conjugated with processed antigen on the surface of the antigen presenting cells (APC). The second event is a co-stimulatory antigen-independent signal involving B7 molecules. The lack of co-stimulatory signal induces anergy, i.e. the inhibition of T cells proliferation, cytokines secretion and cytotoxic activities. The study of these pathways may provide insight about the triggering of pathologic events, such as autoimmune or lymphoproliferative disorders.

The B7 family is an extended group of costimulatory molecules (Coyle et al., 2001). To the B7 family belong the ligands B7-1 (CD80) and B7-2 (CD86): their receptors are CD28, which leads to T cell activation (Linsley and Ledbetter, 1993, June, et al., 1994, Lenschow et al., 1996), and CTLA-4 (CD152), which competes with CD28 and transduces an inhibitory signal (Waterhouse et al., 1996). The critical role of CD152 as a negative regulator of T cell activation is demonstrated by the occurrence of lymphoproliferative disorders in CTLA-4 deficient mice (Waterhouse et al., 1995). Most data on the inhibitory function exerted by CD152 are gathered from studies of proliferation or cytokine production by naïve T lymphocytes during T cell priming (Linsley et al., 1992, Walunas et al., 1995, Walunas and Bluestone, 1998). In particular, CD152 is expressed following T-lymphocyte activation and inhibits the cytolytic functions of CTL clones obtained following PHA stimulation or Ag selection (Saverino et al., 1998).

B7-H1 (PD-L1, CD274) and B7-DC (PD-L2, CD273), whose receptor is PD-1 (CD279), proved to inhibit T-cell proliferation and cytokine secretion (Freeman et al., 2000, Latchman et al., 2001). Otherwise, different studies showed that PD-L1 and PD-L2 engagement increase T cell proliferation and IL-10 or IFN-γ production (Dong et al., 1999, Freeman et al., 2000, Latchman et al., 2001, Chapoval et al., 2001, Tseng et al., 2001). Other molecules related to the family B7 expressed on the surface of T cells are B7-H2 (ICOS-L), B7-H3, B7-H4 whose roles are not fully understood (Hutloff et al., 1999, Sun et al., 2002).

Henry et al. (1999) found that the region coding for butyrophilin (BT) is located at a telomeric position from the MHC class I region on human chromosome 6. In particular they described two genes Bt2 and Bt3, coding for a new group of co-stimulatory molecules (BT2.1, BT2.2, BT2.3, BT3.1, BT3.2 and BT3.3) belonging to the Ig superfamily (IgSF) (Williams and Barclay, 1988) and related to B7 family by sequence similarity analysis: in particular, it shows similarity with the Ig-V like extracellular domain of CD80 and CD86 (Linsley et al., 1992).

The BT3 family members appear in literature with different names: BT3.1 is also called BTF5 (Rhodes et al., 2001), or BTN3A1 (Ruddy et al., 1997), or more recently CD277 (Bensussan and Olive, 2005); BT3.2 is also called BTF4 (Rhodes et al., 2001), or BTN3A2 (Ruddy et al., 1997); and, finally, BT3.3 appears also as BTF3 (Rhodes et al., 2001) or BTN3A3 (Ruddy et al., 1997). BT3 has two Ig-like extracellular domains that characterize the IgSF.

It has been proposed that b7 genes and MHC class I and II genes may have a common ancestral gene and could encode for proteins involved in similar function, such as T cell activation (Rhodes et al., 2001). BT3 molecules have been found on immune cells, such as T, B and NK cells, monocytes and dendritic cells as well as hematopoietic precursors and some neoplastic cell lines (Compte et al., 2004). As for other co-stimulatory molecules, their structure is characterized by three domains: an extracellular domain to bind the ligand, a transmembrane domain and an intracellular domain termed 830.2 which is presumably involved in the regulation of intracellular superoxide concentrations (Henry et al., 1998). So far, the ligand(s) of CD277 is still unknown.

To date, no satisfactory approach has been proven to induce potent immune responses against vaccines, especially in cancer patients. Methods have yet to be devised to overcome the immunosuppressive mechanisms observed in cancer patients, and during chronic infections. Treatment of autoimmune diseases and prevention of transplantation rejection in graft versus host diseases (GVHD) depends on immunosuppressive agents that have serious side effects, or are not always effective. New immunosuppressive agents are desired.

SUMMARY OF THE INVENTION

The present invention relates to an anti-CD277 antibody, which activates or inhibits the cytolytic function, cytokine production and proliferation of Vγ9/Vδ2 T cells. The present invention also relates to an anti-CD277 antibody, which costimulates T cells together with CD3-TCR, and/or which costimulates T cells in addition to CD28-B7 costimulation.

The present invention also relates to an anti-CD277 antibody, which increases the activity and/or survival of monocytes and dendritic cells.

Preferably, the antibody according to the invention is an anti-CD277 antibody, which:
- activates the cytolytic function of Vγ9/Vδ2 T cells, and
- costimulates T cells together with CD3-TCR, and
- costimulates T cells in addition to CD28-B7 costimulation, and
- increases the activity and/or survival of monocytes and dendritic cells.

Particularly, the present invention relates to an anti-CD277 antibody (chosen from mAbs 20.1, 7.2 and 103.2) which is obtainable from one of the hybridomas accessible under CNCM deposit number I-4401, I-4402 and I-4403.

The invention also relates to an anti-CD277 antibody which comprises the CDRs of mAb 20.1. The invention also relates to an anti-CD277 antibody which comprises the CDRs of mAb 7.2. The invention also relates to an anti-CD277 antibody which comprises the CDRs of mAb 103.2. The invention also relates to an anti-CD277 antibody which comprises the CDRs of mAb 108.5.

The invention also relates to one of the mAbs 20.1, 7.2 and 103.2, or a derivative thereof, for the use in therapy.

The invention relates to one of the mAbs 20.1 and 7.2, or a derivative thereof, for use for the treatment of a cancer or a chronic infection.

The invention relates to a vaccine for the treatment of a cancer or a chronic infection comprising one of the mAbs 20.1 and 7.2, or a derivative thereof. The invention relates to a kit for the treatment of a cancer or a chronic infection comprising:
a) mAb 20.1 or 7.2 or a derivative thereof; and
b) a vaccine for the treatment of a cancer or a chronic infection.

The invention relates to an anti-CD277 antibody as defined above for the use in therapy.

The invention finally relates to an anti-CD277 antibody which inhibits the functions of Vγ9/Vδ2 T cells, particularly for use for the treatment of an autoimmune disease, transplantation rejection or a graft versus host disease.

DETAILED DESCRIPTION OF THE INVENTION

Definitions

According to the present invention, "antibody" or "immunoglobulin" have the same meaning, and will be used equally in the present invention. The term "antibody" as used herein refers to immunoglobulin molecules and immunologically active portions of immunoglobulin molecules, i.e., molecules that contain an antigen binding site that immunospecifically binds an antigen. As such, the term antibody encompasses not only whole antibody molecules, but also antibody fragments or derivatives. Antibody fragments include but are not limited to Fv, Fab, F(ab')2, Fab', dsFv, scFv, Sc(Fv)$_2$ and diabodies.

In natural antibodies, two heavy chains are linked to each other by disulfide bonds and each heavy chain is linked to a light chain by a disulfide bond. There are two types of light chain, lambda (λ) and kappa (K). There are five main heavy chain classes (or isotypes) which determine the functional activity of an antibody molecule: IgM, IgD, IgG, IgA and IgE. Each chain contains distinct sequence domains.

The light chain includes two domains, a variable domain (VL) and a constant domain (CL). The heavy chain includes four domains, a variable domain (VH) and three constant domains (CH1, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, transplacental mobility, complement binding, and binding to Fc receptors (FcR). The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from nonhypervariable or framework regions (FR) influence the overall domain structure and hence the combining site. Complementarity Determining Regions or CDRs refer to amino acid sequences which together define the binding affinity and specificity of the natural Fv region of a native immunoglobulin binding site. The light and heavy chains of an immunoglobulin each have three CDRs, designated L-CDRI, L-CDR2, L-CDR3 and H-CDRI, H-CDR2, H-CDR3, respectively. An antigen-binding site, therefore, includes six CDRs, comprising the CDR set from each of a heavy and a light chain V region. Framework Regions (FRs) refer to amino acid sequences interposed between CDRs.

As used herein, a "monoclonal antibody" in its various grammatical forms refers to a population of antibodies that contains only one species of antibody combining sites capable of immunoreacting with a particular epitope. A monoclonal antibody thus typically displays a single binding affinity for any epitope with which it immunoreacts. A monoclonal antibody may therefore contain an antibody molecule having a plurality of antibody combining sites, each immunospecific for a different epitope, e.g. a bispecific monoclonal antibody. Although historically a monoclonal antibody was produced by immortalization of a clonally pure immunoglobulin secreting cell line, a monoclonally pure population of antibody molecules can also be prepared by the methods of the present invention. Laboratory methods for preparing monoclonal antibodies are well known in the art (see, for example, Harlow et al., 1988). Monoclonal antibodies (mAbs) may be prepared by immunizing purified CD277 into a mammal, e.g. a mouse, rat, human and the like mammals. The antibody-producing cells in the immunized mammal are isolated and fused with myeloma or heteromyeloma cells to produce hybrid cells (hybridoma). The hybridoma cells producing the monoclonal antibodies are utilized as a source of the desired monoclonal antibody. This standard method of hybridoma culture is described in Kohler and Milstein (1975). While mAbs can be produced by hybridoma culture the invention is not to be so limited. Also contemplated is the use of mAbs produced by an expressing nucleic acid cloned from a hybridoma of this invention. That is, the nucleic acid expressing the molecules secreted by a hybridoma of this invention can be transferred into another cell line to produce a transformant. The transformant is genotypically distinct from the original hybridoma but is also capable of producing antibody molecules of this invention, including immunologically active fragments of whole antibody molecules, corresponding to those secreted by the hybridoma. See, for example, U.S. Pat. No. 4,642,334 to Reading; PCT Publication No.; European Patent Publications No. 0239400 to Winter et al. and No. 0125023 to Cabilly et al. Antibody generation techniques not involving immunisation are also contemplated such as for example using phage display technology to examine naive libraries (from non-immunised animals); see Barbas et al. (1992), and Waterhouse et al. (1993).

The terms "chimeric antibody" refer to a genetically engineered fusion of parts of an animal antibody, typically a mouse antibody, with parts of a human antibody. Generally, chimeric antibodies contain approximately 33% mouse protein and 67% human protein. Developed to reduce the Human Anti-animal Antibodies response elicited by animal antibodies, they combine the specificity of the animal antibody with the efficient human immune system interaction of a human antibody.

According to the invention, the term "humanized antibody" refers to an antibody having variable region framework and constant regions from a human antibody but retains the CDRs of the animal antibody.

As used herein, the expression "fragment of an antibody" refers to a portion of said antibody comprising at least the antigen-binding domain. Said fragments are for example Fab, fab', F'ab')2 and Fv.

The term "Fab" denotes an antibody fragment having a molecular weight of about 50,000 and antigen binding activity, in which about a half of the N-terminal side of H chain and the entire L chain, among fragments obtained by treating IgG with a protease, papaine, are bound together through a disulfide bond.

The term "F(ab')$_2$" refers to an antibody fragment having a molecular weight of about 100,000 and antigen binding activity, which is slightly larger than the Fab bound via a disulfide bond of the hinge region, among fragments obtained by treating IgG with a protease, pepsin.

The term "Fab'" refers to an antibody fragment having a molecular weight of about 50,000 and antigen binding activity, which is obtained by cutting a disulfide bond of the hinge region of the F(ab')2.

A single chain Fv ("scFv") polypeptide is a covalently linked VH::VL heterodimer which is usually expressed from a gene fusion including VH and VL encoding genes linked by a peptide-encoding linker.

"dsFv" is a VH::VL heterodimer stabilised by a disulfide bond. Divalent and multivalent antibody fragments can form either spontaneously by association of monovalent scFvs, or can be generated by coupling monovalent scFvs by a peptide linker, such as divalent sc(Fv)$_2$.

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites.

As used herein, the expression "derivative of an antibody" refers to an antibody which comprises the 6 CDRs of said antibody.

The inventors have cloned and sequenced the variable domain (VL) of the light chain, and the variable domain (VH) of the heavy chain of the murine monoclonal antibodies described above. The location of the sequences encoding the complementarity determining regions (CDRs) of said antibody have been determined with reference to other antibody sequences (Kabat E A et al., 1991). This system is set forth in Kabat et al., 1987, in Sequences of Proteins of Immunological Interest, US Department of Health and Human Services, NIH, USA (hereafter "Kabat et al."). This numbering system is used in the present specification. The Kabat residue designations do not always correspond directly with the linear numbering of the amino acid residues in SEQ ID sequences. The actual linear amino acid sequence may contain fewer or additional amino acids than in the strict Kabat numbering corresponding to a shortening of, or insertion into, a structural component, whether framework or complementarity determining region (CDR), of the basic variable domain structure. The correct Kabat numbering of residues may be determined for a given antibody by alignment of residues of homology in the sequence of the antibody with a "standard" Kabat numbered sequence. The CDRs of the heavy chain variable domain are located at residues 31-35B (H-CDR1), residues 50-65 (H-CDR2) and residues 95-102 (H-CDR3) according to the Kabat numbering system. The CDRs of the light chain variable domain are located at residues 24-34 (L-CDR1), residues 50-56 (L-CDR2) and residues 89-97 (L-CDR3) according to the Kabat numbering system.

By "purified" and "isolated" it is meant, when referring to a polypeptide (i.e. an antibody according to the invention) or to a nucleotide sequence, that the indicated molecule is present in the substantial absence of other biological macromolecules of the same type.

The term "purified" as used herein preferably means at least 75% by weight, more preferably at least 85% by weight, more preferably still at least 95% by weight, and most preferably at least 98% by weight, of biological macromolecules of the same type are present.

An "isolated" nucleic acid molecule which encodes a particular polypeptide refers to a nucleic acid molecule which is substantially free of other nucleic acid molecules that do not encode the polypeptide; however, the molecule may include some additional bases or moieties which do not deleteriously affect the basic characteristics of the composition.

In the context of the invention, the term "treating" or "treatment", as used herein, means reversing, alleviating, inhibiting the progress of, or preventing the disorder or condition to which such term applies, or one or more symptoms of such disorder or condition.

A "therapeutically effective amount" is intended for a minimal amount of active agent which is necessary to impart therapeutic benefit to a subject. For example, a "therapeutically effective amount" to a mammal is such an amount which induces, ameliorates or otherwise causes an improvement in the pathological symptoms, disease progression or physiological conditions associated with or resistance to succumbing to a disorder.

As used herein, the term "prevention" refers to preventing the disease or condition from occurring in a subject which has not yet been diagnosed as having it. As used herein, the term "subject" denotes a mammal, such as a rodent, a feline, a canine, and a primate. Preferably a subject according to the invention is a human.

As used herein, the terms "cancer", "hyperproliferative" and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness.

The terms "cancer" or "neoplasms" include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

The inventors have deposited a murine anti-CD277 antibody (mAb 20.1) producing hybridoma at the Collection Nationale de Cultures de Microorganismes (CNCM, Institut Pasteur, 25 rue du Docteur Roux, 75724 Paris Cedex 15, France), in accordance with the terms of Budapest Treaty, on Nov. 24, 2010.

The deposited hybridoma for mAb 20.1 has CNCM deposit number I-4402.

"mAb 20.1" refers to an isolated anti-CD277 antibody which is obtainable from the hybridoma accessible under CNCM deposit number I-4402. The expression "a derivative of mAb 20.1" refers to an anti-CD277 antibody which comprises the 6 CDRs of mAb 20.1.

The 6 CDRs of the mAb 20.1 are as follows:

|  | Aminoacid sequence |
|---|---|
| H-CDR1 | RYYLY (SEQ ID NO: 7) |
| H-CDR2 | EINPNNGGTKFNEKFKS (SEQ ID NO: 8) |
| H-CDR3 | EDDYDGTPDAMDY (SEQ ID NO: 9) |
| L-CDR1 | HASQNINLWLS (SEQ ID NO: 10) |
| L-CDR2 | RASNLHT (SEQ ID NO: 11) |
| L-CDR3 | QQGHSYPYT (SEQ ID NO: 12) |

The inventors have deposited a murine anti-CD277 antibody (mAb 7.2) producing hybridoma at the Collection Nationale de Cultures de Microorganismes (CNCM, Institut Pasteur, 25 rue du Docteur Roux, 75724 Paris Cedex 15, France), in accordance with the terms of Budapest Treaty, on Nov. 24, 2010.

The deposited hybridoma for mAb 7.2 has CNCM deposit number I-4401.

"mAb 7.2" refers to an isolated anti-CD277 antibody which is obtainable from the hybridoma accessible under CNCM deposit number I-4401. The expression "a derivative of mAb 7.2" refers to an anti-CD277 antibody which comprises the 6 CDRs of mAb 7.2.

The 6 CDRs of the mAb 7.2 are as follows:

|  | Aminoacid sequence |
|---|---|
| H-CDR1 | RYYMY (SEQ ID NO: 27) |
| H-CDR2 | EINPNNGGTKFNEKFKN (SEQ ID NO: 28) |
| H-CDR3 | EDDYDGTPFAMDY (SEQ ID NO: 29) |
| L-CDR1 | HASQNINVWLS (SEQ ID NO: 30) |
| L-CDR2 | KASNLHT (SEQ ID NO: 31) |
| L-CDR3 | QQGQTYPYT (SEQ ID NO: 32) |

The inventors have deposited a murine anti-CD277 antibody (mAb 103.2) producing hybridoma at the Collection Nationale de Cultures de Microorganismes (CNCM, Institut Pasteur, 25 rue du Docteur Roux, 75724 Paris Cedex 15, France), in accordance with the terms of Budapest Treaty, on Nov. 24, 2010.

The deposited hybridoma for mAb 103.2 has CNCM deposit number I-4403.

"mAb 103.2" refers to an isolated anti-CD277 antibody which is obtainable from the hybridoma accessible under CNCM deposit number I-4403. The expression "a derivative of 103.2" refers to an anti-CD277 antibody which comprises the 6 CDRs of mAb 103.2.

Antibodies of the Invention and Nucleic Acids Encoding them

The present invention relates to an isolated anti-CD277 antibody, which activates the cytolytic function, cytokine production and proliferation of Vγ9/Vδ2 T cells.

By activating the cytolytic function of Vγ9/Vδ2 T cells, it is meant that a significant increase of the cytotoxicity of Vγ9/Vδ2 T cells, i.e. a significant increase of the specific lysis of the target cells by Vγ9/Vδ2 T cells, is observed.

By increasing the cytokine production by Vγ9/Vδ2 T cells, it is meant that a significant increase of the cytokine production by Vγ9/Vδ2 T cells is observed, as compared to control Vγ9/Vδ2 T cells (i.e. non stimulated and non treated).

By increasing the proliferation of Vγ9/Vδ2 T cells, it is meant that a significant increase of the proliferation of Vγ9/Vδ2 T cells is observed, as compared to control Vγ9/Vδ2 T cells (i.e. non stimulated and non treated).

Typically the activation of the cytolytic function of Vγ9/Vδ2 T cells may be measured according to the method described in example 3 (i.e. "Analysis of Vγ9Vδ2 T cell responses by direct cytotoxicity assay", and for example the results "CD277 potentiate the anti-tumor cytolysis mediated by Vγ9Vδ2 T cells"). Examples of isolated anti-CD277 antibodies, which activate the cytolytic function, cytokine production and proliferation of Vγ9/Vδ2 T cells, are mAbs 20.1 or 7.2, or derivatives thereof.

The present invention also relates to an anti-CD277 antibody, which costimulates T cells together with CD3-TCR. By costimulating T cells together with CD3-TCR, it is meant that the reaction cascade following the binding of CD3 with TCR is activated. Typically the costimulation of T cells together with CD3-TCR may be measured according to the method described in example 2 (particularly "CD277 costimulates CD3 signals"). Examples of isolated anti-CD277 antibodies, which costimulate T cells together with CD3-TCR, are mAbs 20.1 or 7.2, or derivatives thereof.

The present invention also relates to an anti-CD277 antibody, which costimulates T cells in addition to CD28-B7 costimulation. By costimulating T cells together with CD28-B7, it is meant that the reaction cascade following the binding of CD28 with B7 is activated. Typically the costimulation of T cells together with CD28-B7 may be measured according to the method described in example 2 (particularly "CD277 costimulates CD3 signals"). Examples of isolated anti-CD277 antibodies, which costimulate T cells together with CD28-B7, are mAbs 20.1 or 7.2, or derivatives thereof.

The present invention also relates to an anti-CD277 antibody, which increases the activity and/or survival of monocytes and dendritic cells. By increasing the activity of monocytes and dendritic cells, it is meant that said anti-CD277 antibody increases costimulatory molecules expression (like CD86, CD80 and HLA-DR) on the surface of monocytes and dendritic cells, and increases the proinflammatory responses induced by TLR ligands in these cells. Typically the increase of the activity and/or survival of monocytes and dendritic cells may be measured according to the method described in example 1 (particularly "Apoptosis detection" and "Cytokines production"). Examples of isolated anti-CD277 antibodies, which increase the activity and/or survival of monocytes and dendritic cells, are mAb 20.1, or derivatives thereof.

The present invention also relates to an isolated anti-CD277 antibody (mAb 20.1) which is obtainable from the hybridoma accessible under CNCM deposit number I-4402.

The present invention relates to the hybridoma accessible under CNCM deposit number I-4402. The invention relates to an antibody which comprises the 6 CDRs of mAb 20.1.

In another embodiment, the invention relates to a derivative of mAb 20.1 which comprises the VL chains and the VH chains of mAb 20.1.

In another embodiment, the invention relates to a derivative of mAb 20.1 which is a chimeric antibody, which comprises the variable domains of mAb 20.1.

The 6 CDRs of 20.1 mAb are as in Table 1 below:

TABLE 1

| | DNA sequence | Aminoacid sequence |
|---|---|---|
| H-CDR1 | AGGTACTATTTGTAC (SEQ ID NO: 1) | RYYLY (SEQ ID NO: 7) |
| H-CDR2 | GAGATAAATCCTAACAATGGT GGTACTAAGTTCAATGAGAAA GTTCAAGAGC (SEQ ID NO: 2) | EINPNNGGTKFNEKFKS (SEQ ID NO: 8) |
| H-CDR3 | GAGGATGATTACGACGGGAC CCCCGATGCTATGGACTAC (SEQ ID NO: 3) | EDDYDGTPDAMDY (SEQ ID NO: 9) |
| L-CDR1 | CATGCCAGTCAGAACATTAAT CTTTGGTTAAGC (SEQ ID NO: 4) | HASQNINLWLS (SEQ ID NO: 10) |
| L-CDR2 | AGGGCTTCCAACTTGCACAC A (SEQ ID NO: 5) | RASNLHT (SEQ ID NO: 11) |
| L-CDR3 | CAACAGGGTCATAGTTATCC GTACACG (SEQ ID NO: 6) | QQGHSYPYT (SEQ ID NO: 12) |

The complete sequences of the variable regions (VH and VL) of mAb 20.1 are the following:

Heavy chain: DNA sequence (423 bp): Leader sequence-FR1-CDR1-FR2-CDR2-FR3-CDR3-FR4
(SEQ ID NO: 13)
ATGGGATGGAGCTATATCATCCTCTTTTTGGTAACAACAGCAACAGGTGT

CCACTCC*CAGGTCCAACTGCAGCAGTCTGGGGCTGAACTGGTGAAGCCTG*

*GGGCTTCAGTGAAGTTGTCCTGCAAGGCTTCTGGCTACACCTTCACC*AGG

TACTATTTGTAC*TGGGTGAAACAGAGGCCTGGACAAGGCCTTGAGTGGAT*

*TGG*AGAGATAAATCCTAACAATGGTGGTACTAAGTTCAATGAGAAGTTCA

AGAGC*AAGGCCACACTGACTGTAGACAAATCCTCCAGAACAACATACATA*

*CAACTCAGCAGCCTGACATCTGAGGACTCTGCGGTCTATTACTGTTCAAG*

AGAGGATGATTACGACGGGACCCCCGATGCTATGGACTAC*GGGGTCAAG*

*GAACCGCAGTCACCGTCTCCTCA*

Heavy chain: Amino acids sequence (141 AA): Leader sequence-FR/-CDR1-FR2-CDR2-FR3-CDR3-FR4
(SEQ ID NO: 14)
MGWSYIILFLVTTATGVHSQVQLQQSGAELVKPGASVKLSCKASGYTFT<u>R</u>

<u>YYLY</u>WVKQRPGQGLEWIG<u>EINPNNGGTKFNEKFKS</u>KATLTVDKSSRTTYI

QLSSLTSEDSAVYYCSR<u>EDDYDGTPDAMDY</u>WGQGTAVTVSS

Light chain: DNA sequence (381 bp): Leader sequence-FR/-CDR1-FR2-CDR2-FR3-CDR3-FR4
(SEQ ID NO: 15)
ATGAGGGTCCTTGCTGAGCTCCTGGGGCTGCTGCTGTTCTGCTTTTTAGG

TGTGAGATGT*GACATCCAGATGAACCAGTCTCCATCCAGTCTGTCTGCAT*

*CCCTTGGAGACACAATTACCATCACTTGC*CATGCCAGTCAGAACATTAAT

CTTTGGTTAAGC*TGGTACCAGCAGAGACCAGGAAATATTCCTAAACTTCT*

*GATCTAT*AGGGCTTCCAACTTGCACAC*AGGCGTCCCATCAAGGTTTAGTG*

*GCAGTGGATCTGCAACAGGTTTCACATTAACCATCAGCAGCCTGCAGCCT*

*GAAGACATTGCCACTTACTACTGT*CAACAGGGTCATAGTTATCCGTACAC

GTTCGGAGGGGGGACCAAACTGGACATAAAA

Light chain: Amino acids sequence (127 AA): Leader sequence-FR/-CDR1-FR2-CDR2-FR3-CDR3-FR4
(SEQ ID NO: 16)
MRVLAELLGLILFCFLGVRCDIQMNQSPSSLSASLGDTITIT<u>CHASQNIN</u>

<u>LWLS</u>WYQQRPGNIPKLLIY<u>RASNLHT</u>GVPSRFSGSGSATGFTLTISSLQP

EDIATYYC<u>QQGHSYPYT</u>FGGGTKLDIK

The present invention also refers to antibodies comprising SEQ ID NO:18 in their heavy chain and SEQ ID NO:20 in their light chain. It also refers to antibodies encoded by at least nucleotidic sequences SEQ ID NO:17 for the heavy chain and SEQ ID NO:19 for the light chain:

Heavy chain: DNA sequence: FR1-CDR1-FR2-CDR2-FR3-CDR3-FR4
(SEQ ID NO: 17)
CAGGTCCAACTGCAGCAGTCTGGGGCTGAACTGGTGAAGCCTGGGGCTTC AGTGAAGTTGTCCTGCAAGGCTTCTGGCTACACCTTCACC<u>AGGTACTATT</u>

<u>TGTAC</u>TGGGTGAAACAGAGGCCTGGACAAGGCCTTGAGTGGATTGG<u>AGAG</u>

<u>ATAAATCCTAACAATGGTGGTACTAAGTTCAATGAGAAGTTCAAGAGCAA</u>

GGCCACACTGACTGTAGACAAATCCTCCAGAACAACATACATACAACTCA

GCAGCCTGACATCTGAGGACTCTGCGGTCTATTACTGTTCAAG<u>AGAGGAT</u>

<u>GATTACGACGGGACCCCCGATGCTATGGACTAC</u>GGGGTCAAGGAACCGC

AGTCACCGTCTCCTCA

Heavy chain: Amino acids sequence: FR1-CDR1-FR2-CDR2-FR3-CDR3-FR4
(SEQ ID NO: 18)
QVQLQQSGAELVKPGASVKLSCKASGYTFT<u>RYYLY</u>WVKQRPGQGLEWIG<u>E</u>

<u>INPNNGGTKFNEKFKS</u>KATLTVDKSSRTTYIQLSSLTSEDSAVYYCSR<u>ED</u>

<u>DYDGTPDAMDY</u>WGQGTAVTVSS

-continued

Light chain: DNA sequence: FR1-CDR1-FR2-CDR2-FR3-
CDR3-FR4
(SEQ ID NO: 19)
GACATCCAGATGAACCAGTCTCCATCCAGTCTGTCTGCATCCCTTGGAGA

CACAATTACCATCACTTGCCATGCCAGTCAGAACATTAATCTTTGGTTAA

GCTGGTACCAGCAGAGACCAGGAAATATTCCTAAACTTCTGATCTATAGG

GCTTCCAACTTGCACACAGGCGTCCCATCAAGGTTTAGTGGCAGTGGATC

TGCAACAGGTTTCACATTAACCATCAGCAGCCTGCAGCCTGAAGACATTG

CCACTTACTACTGTCAACAGGGTCATAGTTATCCGTACACGTTCGGAGGG

GGGACCAAACTGGACATAAAA

Light chain: Amino acids sequence: FR1-CDR1-FR2-
CDR2-FR3-CDR3-FR4
(SEQ ID NO: 20)
DIQMNQSPSSLSASLGDTITITCHASQNINLWLSWYQQRPGNIPKLLIYR

ASNLHTGVPSRFSGSGSATGFTLTISSLQPEDIATYYCQQGHSYPYTFGG

GTKLDIK

The present invention also relates to an isolated anti-CD277 antibody (mAb 7.2) which is obtainable from the hybridoma accessible under CNCM deposit number I-4401.

The present invention relates to the hybridoma accessible under CNCM deposit number I-4401. The invention relates to an antibody which comprises the 6 CDRs of mAb 7.2.

In another embodiment, the invention relates to a derivative of mAb 7.2 which comprises the VL chains and the VH chains of mAb 7.2.

In another embodiment, the invention relates to a derivative of mAb 7.2 which is a chimeric antibody, which comprises the variable domains of mAb 7.2.

The 6 CDRs of the 7.2 mAb are as in Table 2 below:

TABLE 2

|  | DNA sequence | Aminoacid sequence |
|---|---|---|
| H-CDR1 | AGATACTATATGTAT (SEQ ID NO: 21) | RYYMY (SEQ ID NO: 27) |
| H-CDR2 | GAGATTAATCCTAACAATGG TGGTACTAAGTTCAATGAGA AGTTCAAGAAC (SEQ ID NO: 22) | EINPNNGGTKFNEKFKN (SEQ ID NO: 28) |
| H-CDR3 | GAGGATGATTACGACGGGA CCCCCTTTGCTATGGACTAC (SEQ ID NO: 23) | EDDYDGTPFAMDY (SEQ ID NO: 29) |
| L-CDR1 | CATGCCAGTCAGAACATTAA TGTTTGGTTAAGC (SEQ ID NO: 24) | HASQNINVWLS (SEQ ID NO: 30) |
| L-CDR2 | AAGGCTTCCAACTTGCACAC A (SEQ ID NO: 25) | KASNLHT (SEQ ID NO: 31) |
| L-CDR3 | CAACAGGGTCATAGTTATCC GTACACG (SEQ ID NO: 26) | QQGQTYPYT (SEQ ID NO: 32) |

The complete sequences of the variable regions (VH and VL) of mAb 7.2 are the following:

Heavy chain: DNA sequence (423 bp): Leader
sequence-FR1-CDR1-FR2-CDR2-FR3-CDR3-FR4
(SEQ ID NO: 33)
ATGGGATGGAGCTATATCATCCTCTTTTTGGTAGCAACAGCAACAGGTGT

CCACTCCCAGGTCCAACTGCAGCAGTCTGGGGCTGAACTGGTGAAGCCTG

GGGCTTCAGTGAAGTTGTCCTGCAAGGCTTCTGGCTACATCTTCACCAGA

TACTATATGTATTGGGTGAAGCAGAGGCCTGGACAAGGCCTTGAGTGGAT

TGGAGAGATTAATCCTAACAATGGTGGTACTAAGTTCAATGAGAAGTTCA

AGAACAAGGCCACACTGACTGTAGACAAATTTTCCAGCACAGCATACATG

CAACTCAGGAGCCTGACATCTGAGGACTCTGCGGTCTATTATTGTTCAAG

AGAGGATGATTACGACGGGACCCCCTTTGCTATGGACTACTGGGGTCAAG

GAACCTCAGTCACCGTCTCCTCA

Heavy chain: Amino acids sequence (141 AA): Leader
sequence-FR1-CDR1-FR2-CDR2-FR3-CDR3-FR4
(SEQ ID NO: 34)
MGWSYIILFLVATATGVHSQVQLQQSGAELVKPGASVKLSCKASGYIFTR

YYMYWVKQRPGQGLEWIGEINPNNGGTKFNEKFKNKATLTVDKFSSTAYM

QLRSLTSEDSAVYYCSREDDYDGTPFAMDYWGQGTSVTVSS

Light chain: DNA sequence (381 bp): Leader
sequence-FR1-CDR1-FR2-CDR2-FR3-CDR3-FR4
(SEQ ID NO: 35)
ATGAGGGTCCTTGCTGAGCTCCTGGGGCTGCTGCTGTTCTGCTTTTTAGG

TGTGAGATGTGACATCCAGATGAACCAGTCTCCATCCAGTCTGTCTGCAT

CCCTTGGAGACACAATTACCATCACTTGCCATGCCAGTCAGAACATTAAT

GTTTGGTTAAGCTGGTACCAGCAGAAACCAGGAAATATTCCTAAACTATT

GATCTATAAGGCTTCCAACTTGCACACAGGCGTCCCATCAAGATTTACTG

GCAGTGGATCTGGAACAGGTTTCACATTAACCATCAGCAGCCTGCAGCCT

GAAGACATTGCCACTTACTACTGTCAACAGGGTCAAACTTATCCATACAC

GTTCGGAGGGGGGACCAAGTTGGAAATAAAG

Light chain: Amino acids sequence (127 AA): Leader
sequence-FR1-CDR1-FR2-CDR2-FR3-CDR3-FR4
(SEQ ID NO: 36)
MRVLAELLGLLLFCFLGVRCDIQMNQSPSSLSASLGDTITITCHASQNIN

VWLSWYQQKPGNIPKLLIYKASNLHTGVPSRFTGSGSGTGFTLTISSLQP

EDIATYYCQQGQTYPYTFGGGTKLEIK

The present invention also refers to antibodies comprising SEQ ID NO:38 in their heavy chain and SEQ ID NO:40 in their light chain. It also refers to antibodies encoded by at least nucleotidic sequences SEQ ID NO:37 for the heavy chain and SEQ ID NO:39 for the light chain:

Heavy chain: DNA sequence: FR1 -CDR1-FR2-CDR2-FR3-
CDR3-FR4
(SEQ ID NO: 37)
CAGGTCCAACTGCAGCAGTCTGGGGCTGAACTGGTGAAGCCTGGGGCTTC

AGTGAAGTTGTCCTGCAAGGCTTCTGGCTACATCTTCACCAGATACTATA

TGTATTGGGTGAAGCAGAGGCCTGGACAAGGCCTTGAGTGGATTGGAGAG

ATTAATCCTAACAATGGTGGTACTAAGTTCAATGAGAAGTTCAAGAACAA

-continued

```
GGCCACACTGACTGTAGACAAATTTTCCAGCACAGCATACATGCAACTCA

GGAGCCTGACATCTGAGGACTCTGCGGTCTATTATTGTTCAAGAGAGGAT

GATTACGACGGGACCCCCTTTGCTATGGACTACTGGGGTCAAGGAACCTC

AGTCACCGTCTCCTCA
```

Heavy chain: Amino acids sequence: FR1-CDR1-FR2-
CDR2-FR3-CDR3-FR4
(SEQ ID NO: 38)
QVQLQQSGAELVKPGASVKLSCKASGYIFT<u>RYYMY</u>WVKQRPGQGLEWIG<u>E</u>

<u>INPNNGGTKFNEKFKN</u>KATLTVDKFSSTAYMQLRSLTSEDSAVYYCS<u>RED</u>

<u>DYDGTPFAMDY</u>WGQGTSVTVSS

Light chain: DNA sequence: FR1-CDR1-FR2-CDR2-FR3-
CDR3-FR4
(SEQ ID NO: 39)
```
GACATCCAGATGAACCAGTCTCCATCCAGTCTGTCTGCATCCCTTGGAGA

CACAATTACCATCACTTGCCATGCCAGTCAGAACATTAATGTTTGGTTAA

GCTGGTACCAGCAGAAACCAGGAAATATTCCTAAACTATTGATCTATAAG

GCTTCCAACTTGCACACAGGCGTCCCATCAAGATTTACTGGCAGTGGATC

TGGAACAGGTTTCACATTAACCATCAGCAGCCTGCAGCCTGAAGACATTG

CCACTTACTACTGTCAACAGGGTCAAACTTATCCATACACGTTCGGAGGG

GGGACCAAGTTGGAAATAAAG
```

Light chain: Amino acids sequence: FR1-CDR1-FR2-
CDR2-FR3-CDR3-FR4
(SEQ ID NO: 40)
DIQMNQSPSSLSASLGDTITIT<u>CHASQNINVWLS</u>WYQQKPGNIPKLLIY<u>K</u>

<u>ASNLHT</u>GVPSRFTGSGSGTGFTLTISSLQPEDIATYYC<u>QQGQTYPYT</u>FGG

GTKLEIK

In a particular embodiment of the invention, the antibodies of the invention are chosen from 20.1 mAb, 7.2 mAb, their fragments and derivatives.

The present invention relates to an isolated anti-CD277 antibody, which inhibits the cytolytic function, cytokine production and proliferation of Vγ9/Vδ2 T cells.

By inhibiting the cytolytic function of Vγ9/Vδ2 T cells, it is meant that a significant decrease of the cytotoxicity of Vγ9/Vδ2 T cells, i.e. a significant decrease of the specific lysis of the target cells by Vγ9/Vδ2 T cells, is observed, as compared to control Vγ9/Vδ2 T cells (i.e. non stimulated and non treated).

By inhibiting the cytokine production by Vγ9/Vδ2 T cells, it is meant that a significant decrease of the cytokine production by Vγ9/Vδ2 T cells is observed, as compared to control Vγ9/Vδ2 T cells (i.e. non stimulated and non treated).

By inhibiting the proliferation of Vγ9/Vδ2 T cells, it is meant that a significant decrease of the proliferation of Vγ9/Vδ2 T cells is observed, as compared to control Vγ9/Vδ2 T cells (i.e. non stimulated and non treated).

Typically the inhibition of the cytolytic function of Vγ9/Vδ2 T cells may be measured according to the method described in example 3 (i.e. "Analysis of Vγ9Vδ2 T cell responses by direct cytotoxicity assay"). An example of an isolated anti-CD277 antibody, which inhibits the cytolytic function, cytokine production and proliferation of Vγ9/Vδ2 T cells, is mAbs 103.2, or derivatives thereof.

The present invention also relates to an isolated anti-CD277 antibody (mAb 103.2) which is obtainable from the hybridoma accessible under CNCM deposit number I-4403.

The present invention relates to the hybridoma accessible under CNCM deposit number I-4403. The invention relates to an antibody which comprises the 6 CDRs of mAb 103.2.

In another embodiment, the invention relates to a derivative of mAb 103.2 which comprises the VL chains and the VH chains of mAb 103.2.

In another embodiment, the invention relates to a derivative of mAb 103.2 which is a chimeric antibody, which comprises the variable domains of mAb 103.2.

The present invention also relates to an isolated anti-CD277 antibody (mAb 108.5) or an antibody which comprises the 6 CDRs of mAb 108.5.

In another embodiment, the invention relates to a derivative of mAb 108.5 which comprises the VL chains and the VH chains of mAb 108.5.

In another embodiment, the invention relates to a derivative of mAb 108.5 which is a chimeric antibody, which comprises the variable domains of mAb 108.5.

The 6 CDRs of the 108.5 mAb are as in Table 3 below:

TABLE 2

| | DNA sequence | Aminoacid sequence |
|---|---|---|
| H-CDR1 | GGCTTCGCCATTAAC (SEQ ID NO: 41) | GFAIN (SEQ ID NO: 47) |
| H-CDR2 | CTTATTTATCCTTACAATGGT GGTACTACCTACAGCCAGA GGTTCAAGGGC (SEQ ID NO: 42) | LIYPYNGGTTYSQRFKG (SEQ ID NO: 48) |
| H-CDR3 | CGGCGGGATGGTTACTCCT GGTTTGCTTAC (SEQ ID NO: 43) | RRDGYSWFAY (SEQ ID NO: 49) |
| L-CDR1 | AGAGCCAGCGAAAGTGTTG AGAATTATGGCATTATTTTA TGAAC (SEQ ID NO: 44) | RASESVENYGIIFMN (SEQ ID NO: 50) |
| L-CDR2 | TCTGCATCCAACCAAGGATC C (SEQ ID NO: 45) | SASNQGS (SEQ ID NO: 51) |
| L-CDR3 | CAGCAAAGTAAGGAGGCTC CGTTCACG (SEQ ID NO: 46) | QQSKEAPFT (SEQ ID NO: 52) |

The complete sequences of the variable regions (VH and VL) of mAb 108.5 are the following:

Heavy chain: DNA sequence (bp): Leader sequence-
FR1-CDR1-FR2-CDR2-FR3-CDR3-FR4
(SEQ ID NO: 53)
ATGGGATGGAGCTGGATCTTTCTCTTCCTCCTGTCAGGAACTGCAGGTGT

CCACTCTGAGGTCCAGTTGCAACAGTCTGGACCTGAGCTGGTGAAGCCTG

GAGCTTCAATGAAGATATCCTGCAAGGCTTCTGGTTACTCATTCACT<u>GGC</u>

<u>TTCGCCATTAAC</u>TGGGTGAAACAGAGCCATGGACAGAACCTTGAGTGGAT

TGGG<u>CTTATTTATCCTTACAATGGTGGTACTACCTACAGCCAGAGGTTCA</u>

<u>AGGGC</u>AAGGCCACATTAACTGTAGACAAGTCATCCACCACAGCCTACATG

GAGCTCCTCAGTCTGACATCTGAAGACTCTGCAGTCTATTACTGTGCAAG

ACGGCGGGATGGTTACTCCTGGTTTGCTTACTGGGGCCAAGGGACTCTGG

TCACTGTCTCTGCA

Heavy chain: Amino acids sequence (AA): Leader sequence-FR1-CDR1- FR2-CDR2-FR3-CDR3-FR4

(SEQ ID NO: 54)
MGWSWIFLFLLSGTAGVHSEVQLQQSGPELVKPGASMKISCKASGYSFT<u>G</u>

<u>FAIN</u>WVKQSHGQNLEWIG<u>LIYPYNGGTTYSQRFKG</u>KATLTVDKSSTTAYM

ELLSLTSEDSAVYYCARR<u>RDGYSWFAY</u>WGQGTLVTVSA

Light chain: DNA sequence (bp): Leader sequence-FR1-CDR1-FR2-CDR2-FR3-CDR3-FR4

(SEQ ID NO: 55)
ATGGAGAAAGACACACTCCTGCTATGGGGCCTGCTTCTCTGGGTTCCAGC

TTCCACAGGTGACATTGTGCTGACCCAATCTCCAGCTTCTTTGGCTGTGT

CTCTAGGGCAGAGGGCCACCATCTCCTGC<u>AGAGCCAGCGAAAGTGTTGAG</u>

<u>AATTATGGCATTATTTTTATGAAC</u>TGGTTCCAACAGAAACCAGGACAGCC

ACCCAAACTCCTCATCTTT<u>CTGCATCCAACCAAGGATCC</u>GGGGTCCCTG

CCAGGTTTAATGGCAGTGGGTCTGGGACAGACTTCAGCCTCAACATCCAT

CCTATGGAGGAGGATGATACTGCAATGTATTTCTGT<u>CAGCAAAGTAAGGA</u>

<u>GGCTCCGTTCACG</u>TTCGGAGGGGGGACCAAGCTGGAAATAAAA

Light chain: Amino acids sequence (AA): Leader sequence-FR1-CDR1-FR2-CDR2-FR3-CDR3-FR4

(SEQ ID NO: 56)
MEKDTLLLWGLLLWVPASTGDIVLTQSPASLAVSLGQRATISC<u>RASESVE</u>

<u>NYGIIFMN</u>WFQQKPGQPPKLLIF<u>SASNQGS</u>GVPARFNGSGSGTDFSLNIH

PMEEDDTAMYFC<u>QQSKEAPFT</u>FGGGTKLEIK

The present invention also refers to antibodies comprising SEQ ID NO:58 in their heavy chain and SEQ ID NO:60 in their light chain. It also refers to antibodies encoded by at least nucleotidic sequences SEQ ID NO:57 for the heavy chain and SEQ ID NO:59 for the light chain:

Heavy chain: DNA sequence: FR1-CDR1-FR2-CDR2-FR3-CDR3-FR4

(SEQ ID NO: 57)
GAGGTCCAGTTGCAACAGTCTGGACCTGAGCTGGTGAAGCCTGGAGCTTC

AATGAAGATATCCTGCAAGGCTTCTGGTTACTCATTCACT<u>GGCTTCGCCA</u>

<u>TTAAC</u>TGGGTGAAACAGAGCCATGGACAGAACCTTGAGTGGATTGGG<u>CTT</u>

<u>ATTTATCCTTACAATGGTGGTACTACCTACAGCCAGAGGTTCAAGGGC</u>AA

GGCCACATTAACTGTAGACAAGTCATCCACCACAGCCTACATGGAGCTCC

TCAGTCTGACATCTGAAGACTCTGCAGTCTATTACTGTGCAAGA<u>CGGCGG</u>

<u>GATGGTTACTCCTGGTTTGCTTAC</u>TGGGGCCAAGGGACTCTGGTCACTGT

CTCTGCA

Heavy chain: Amino acids sequence: FR1-CDR1-FR2-CDR2-FR3-CDR3-FR4

(SEQ ID NO: 58)
EVQLQQSGPELVKPGASMKISCKASGYSFT<u>GFAIN</u>WVKQSHGQNLEWIG<u>L</u>

<u>IYPYNGGTTYSQRFKG</u>KATLTVDKSSTTAYMELLSLTSEDSAVYYCARR<u>R</u>

<u>DGYSWFAY</u>WGQGTLVTVSA

Light chain: DNA sequence: FR1-CDR1-FR2-CDR2-FR3-CDR3-FR4

(SEQ ID NO: 59)
GACATTGTGCTGACCCAATCTCCAGCTTCTTTGGCTGTGTCTCTAGGGCA

GAGGGCCACCATCTCCTGC<u>AGAGCCAGCGAAAGTGTTGAGAATTATGGCA</u>

<u>TTATTTTTATGAAC</u>TGGTTCCAACAGAAACCAGGACAGCCACCCAAACTC

CTCATCTTT<u>TCTGCATCCAACCAAGGATCC</u>GGGGTCCCTGCCAGGTTTAA

TGGCAGTGGGTCTGGGACAGACTTCAGCCTCAACATCCATCCTATGGAGG

AGGATGATACTGCAATGTATTTCTGT<u>CAGCAAAGTAAGGAGGCTCCGTTC</u>

<u>ACG</u>TTCGGAGGGGGGACCAAGCTGGAAATAAAA

Light chain: Amino acids sequence: FR1-CDR1-FR2-CDR2-FR3-CDR3-FR4

(SEQ ID NO: 60)
DIVLTQSPASLAVSLGQRATISC<u>RASESVENYGIIFMN</u>WFQQKPGQPPKL

LIF<u>SASNQGS</u>GVPARFNGSGSGTDFSLNIHPMEEDDTAMYFC<u>QQSKEAPF</u>

<u>T</u>FGGGTKLEIK

In a particular embodiment of the invention, the antibody of the invention is chosen from 108.5, its fragments and derivatives.

In an embodiment, an antibody of the invention is a monoclonal antibody.

In an embodiment, an antibody of the invention is a chimeric antibody.

In an embodiment, an antibody of the invention is a humanized antibody.

A further embodiment of the invention relates to a nucleic acid sequence encoding an antibody of the invention.

In a particular embodiment, the invention relates to a nucleic acid sequence encoding the VH domain or the VL domain of an antibody of the invention. Typically, said nucleic acid is a DNA or RNA molecule, which may be included in any suitable vector, such as a plasmid, cosmid, episome, artificial chromosome, phage or a viral vector.

The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence. So, a further object of the invention relates to a vector comprising a nucleic acid of the invention.

Such vectors may comprise regulatory elements, such as a promoter, enhancer, terminator and the like, to cause or direct expression of said antibody upon administration to a subject. Examples of promoters and enhancers used in the expression vector for animal cell include early promoter and enhancer of SV40, LTR promoter and enhancer of Moloney mouse leukemia virus, promoter and enhancer of immunoglobulin H chain and the like.

Any expression vector for animal cell can be used, so long as a gene encoding the human antibody C region can be inserted and expressed. Examples of suitable vectors include pAGE107, pAGE103, pHSG274, pKCR, pSGI beta d2-4- and the like.

Other examples of plasmids include replicating plasmids comprising an origin of replication, or integrative plasmids, such as for instance pUC, pcDNA, pBR, and the like. Other examples of viral vector include adenoviral, retroviral, herpes virus and AAV vectors. Such recombinant viruses may be produced by techniques known in the art, such as by transfecting packaging cells or by transient transfection with helper plasmids or viruses. Typical examples of virus packaging cells include PA317 cells, PsiCRIP cells, GPenv+ cells, 293 cells, etc. Detailed protocols for producing such replication-defective recombinant viruses may be found for instance in WO 95/14785, WO 96/22378, U.S. Pat. Nos. 5,882,877, 6,013,516, 4,861,719, 5,278,056 and WO 94/19478.

A further object of the present invention relates to a cell which has been transfected, infected or transformed by a nucleic acid and/or a vector according to the invention. The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA has been "transformed". The nucleic acids of the invention may be used to produce an antibody of the invention in a suitable expression system. The term "expression system" means a host cell and compatible vector under suitable conditions, e.g. for the expression of a protein coded for by foreign DNA carried by the vector and introduced to the host cell.

Common expression systems include *E. coli* host cells and plasmid vectors, insect host cells and Baculovirus vectors, and mammalian host cells and vectors. Other examples of host cells include, without limitation, prokaryotic cells (such as bacteria) and eukaryotic cells (such as yeast cells, mammalian cells, insect cells, plant cells, etc.). Specific examples include *E. coli, Kluyveromyces* or *Saccharomyces* yeasts, mammalian cell lines (e.g., Vero cells, CHO cells, 3T3 cells, COS cells, etc.) as well as primary or established mammalian cell cultures (e.g., produced from lymphoblasts, fibroblasts, embryonic cells, epithelial cells, nervous cells, adipocytes, etc.). Examples also include mouse SP2/0-Agl4 cell (ATCC CRL1581), mouse P3X63-Ag8.653 cell (ATCC CRL1580), CHO cell in which a dihydrofolate reductase gene (hereinafter referred to as "DHFR gene") is defective, rat YB2/3HL.P2.G11.16Ag.20 cell (ATCC CRL1662, hereinafter referred to as "YB2/0 cell"), and the like.

The present invention also relates to a method of producing a recombinant host cell expressing an antibody according to the invention, said method comprising the steps of:
(i) introducing in vitro or ex vivo a recombinant nucleic acid or a vector as described above into a competent host cell,
(ii) culturing in vitro or ex vivo the recombinant host cell obtained, and
(iii) optionally, selecting the cells which express and/or secrete said antibody. Such recombinant host cells can be used for the production of antibodies of the invention.

Methods of Producing Antibodies of the Invention

Antibodies of the invention may be produced by any technique known in the art, such as, without limitation, any chemical, biological, genetic or enzymatic technique, either alone or in combination.

Knowing the amino acid sequence of the desired sequence, one skilled in the art can readily produce said antibodies, by standard techniques for production of polypeptides. For instance, they can be synthesized using well-known solid phase method, preferably using a commercially available peptide synthesis apparatus (such as that made by Applied Biosystems, Foster City, Calif.) and following the manufacturer's instructions. Alternatively, antibodies of the invention can be synthesized by recombinant DNA techniques well-known in the art. For example, antibodies can be obtained as DNA expression products after incorporation of DNA sequences encoding the antibodies into expression vectors and introduction of such vectors into suitable eukaryotic or prokaryotic hosts that will express the desired antibodies, from which they can be later isolated using well-known techniques.

In particular, the invention further relates to a method of producing an antibody of the invention, which method comprises the steps consisting of:
(i) culturing a transformed host cell according to the invention under conditions suitable to allow expression of said antibody; and
(ii) recovering the expressed antibody.

In another particular embodiment, the method comprises the steps of:
(i) culturing the hybridoma deposited as CNCM I-4401, CNCM I-4402 or CNCM I-4403 under conditions suitable to allow expression of the antibody; and
(ii) recovering the expressed antibody.

Antibodies of the invention are suitably separated from the culture medium by conventional immunoglobulin purification procedures such as, for example, protein A-Sepharose, hydroxylapatite chromatography, gel electrophoresis, dialysis, or affinity chromatography.

In a particular embodiment, the human chimeric antibody of the present invention can be produced by obtaining nucleic sequences encoding VL and VH domains as previously described, constructing a human chimeric antibody expression vector by inserting them into an expression vector for animal cell having genes encoding human antibody CH and human antibody CL, and expressing the coding sequence by introducing the expression vector into an animal cell. As the CH domain of a human chimeric antibody, it may be any region which belongs to human immunoglobulin, but those of IgG class are suitable and any one of subclasses belonging to IgG class, such as IgGl, IgG2, IgG3 and IgG4, can also be used. Also, as the CL of a human chimeric antibody, it may be any region which belongs to Ig, and those of kappa class or lambda class can be used. Methods for producing chimeric antibodies involve conventional recombinant DNA and gene transfection techniques are well known in the art (See patent documents U.S. Pat. Nos. 5,202,238; and 5,204,244).

The humanized antibody of the present invention may be produced by obtaining nucleic acid sequences encoding CDR domains, as previously described, constructing a humanized antibody expression vector by inserting them into an expression vector for animal cell having genes encoding (i) a heavy chain constant region identical to that of a human antibody and (ii) a light chain constant region identical to that of a human antibody, and expressing the genes by introducing the expression vector into an animal cell.

The humanized antibody expression vector may be either of a type in which a gene encoding an antibody heavy chain and a gene encoding an antibody light chain exists on separate vectors or of a type in which both genes exist on the same vector (tandem type). In respect of easiness of construction of a humanized antibody expression vector, easiness of introduction into animal cells, and balance between the expression levels of antibody H and L chains in animal cells, humanized antibody expression vector of the tandem type is preferred. Examples of tandem type humanized antibody expression vector include pKANTEX93 (WO 97/10354), pEE18 and the like.

Methods for producing humanized antibodies based on conventional recombinant DNA and gene transfection techniques are well known in the art. Antibodies can be humanized using a variety of techniques known in the art including, for example, CDR-grafting (EP 239,400; PCT publication WO91/09967; U.S. Pat. Nos. 5,225,539; 5,530,101; and 5,585,089), veneering or resurfacing (EP 592,106; EP 519, 596), and chain shuffling (U.S. Pat. No. 5,565,332). The general recombinant DNA technology for preparation of such antibodies is also known (see European Patent Application EP 125023 and International Patent Application WO 96/02576).

The Fab of the present invention can be obtained by treating an antibody which specifically reacts with CD277 with a protease, papaine. Also, the Fab can be produced by inserting DNA encoding Fab of the antibody into a vector for prokaryotic expression system, or for eukaryotic expression system, and introducing the vector into a procaryote or eucaryote (as appropriate) to express the Fab.

The F(ab')2 of the present invention can be obtained treating an antibody which specifically reacts with CD277 with a protease, pepsin.

Also, the F(ab')2 can be produced by binding Fab' described below via a thioether bond or a disulfide bond.

The Fab' of the present invention can be obtained by treating F(ab')2 which specifically reacts with human CD277 with a reducing agent, dithiothreitol. Also, the Fab' can be produced by inserting DNA encoding Fab' fragment of the antibody into an expression vector for prokaryote, or an expression vector for eukaryote, and introducing the vector into a prokaryote or eukaryote (as appropriate) to perform its expression.

The scFv of the present invention can be produced by obtaining cDNA encoding the VH and VL domains as previously described, constructing DNA encoding scFv, inserting the DNA into an expression vector for prokaryote, or an expression vector for eukaryote, and then introducing the expression vector into a prokaryote or eukaryote (as appropriate) to express the scFv. To generate a humanized scFv fragment, a well known technology called CDR grafting may be used, which involves selecting the complementary determining regions (CDRs) from a donor scFv fragment, and grafting them onto a human scFv fragment framework of known three dimensional structure (see, e.g., WO98/45322; WO 87/02671; U.S. Pat. Nos. 5,859,205; 5,585,089; 4,816,567; EP0173494).

Amino acid sequence modification(s) of the antibodies described herein are contemplated. For example, it may be desirable to improve the binding affinity and/or other biological properties of the antibody. It is known that when a humanized antibody is produced by simply grafting only CDRs in VH and VL of an antibody derived from a non-human animal in FRs of the VH and VL of a human antibody, the antigen binding activity is reduced in comparison with that of the original antibody derived from a non-human animal. It is considered that several amino acid residues of the VH and VL of the non-human antibody, not only in CDRs but also in FRs, are directly or indirectly associated with the antigen binding activity. Hence, substitution of these amino acid residues with different amino acid residues derived from FRs of the VH and VL of the human antibody would reduce of the binding activity.

In order to resolve the problem, in antibodies grafted with human CDR, attempts have to be made to identify, among amino acid sequences of the FR of the VH and VL of human antibodies, an amino acid residue which is directly associated with binding to the antibody, or which interacts with an amino acid residue of CDR, or which maintains the three-dimensional structure of the antibody and which is directly associated with binding to the antigen. The reduced antigen binding activity could be increased by replacing the identified amino acids with amino acid residues of the original antibody derived from a non-human animal.

Modifications and changes may be made in the structure of the antibodies of the present invention, and in the DNA sequences encoding them, and still obtain a functional molecule that encodes an antibody with desirable characteristics. In making the changes in the amino sequences, the hydropathic index of amino acids may be considered. The importance of the hydropathic amino acid index in conferring interactive biologic function on a protein is generally understood in the art. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophane (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

A further embodiment of the present invention also encompasses function-conservative variants of the antibodies of the present invention.

"Function-conservative variants" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like).

Amino acids other than those indicated as conserved may differ in a protein so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm.

A "function-conservative variant" also includes a polypeptide which has at least 60% amino acid identity as determined by BLAST or FASTA algorithms, preferably at least 75%, more preferably at least 85%, still preferably at least 90%, and even more preferably at least 95%, and which has the same or substantially similar properties or functions as the native or parent protein to which it is compared. Two amino acid sequences are "substantially homologous" or "substantially similar" when greater than 80%, preferably greater than 85%, preferably greater than 90% of the amino acids are identical, or greater than about 90%, preferably grater than 95%, are similar (functionally identical) over the whole length of the shorter sequence. Preferably, the similar or homologous sequences are identified by alignment using, for example, the GCG (Genetics Computer Group, Program Manual for the GCG Package, Version 7, Madison, Wis.) pileup program, or any of sequence comparison algorithms such as BLAST, FASTA, etc.

For example, certain amino acids may be substituted by other amino acids in a protein structure without appreciable loss of activity. Since the interactive capacity and nature of a protein define the protein's biological functional activity, certain amino acid substitutions can be made in a protein sequence, and, of course, in its DNA encoding sequence, while nevertheless obtaining a protein with like properties.

It is thus contemplated that various changes may be made in the antibodies sequences of the invention, or corresponding DNA sequences which encode said antibodies, without appreciable loss of their biological activity.

It is known in the art that certain amino acids may be substituted by other amino acids having a similar hydropathic index or score and still result in a protein with similar biological activity, i.e. still obtain a biological functionally equivalent protein. As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine. Another type of amino acid modification of the antibody of the invention may be useful for altering the original glycosylation pattern of the antibody.

By "altering" is meant deleting one or more carbohydrate moieties found in the antibody, and/or adding one or more glycosylation sites that are not present in the antibody.

Glycosylation of antibodies is typically N-linked. "N-linked" refers to the attachment of the carbohydrate moiety to the side chain of an asparagine residue. The tripeptide sequences asparagine-X-serine and asparagines-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. Addition of glycosylation sites to the antibody is conveniently accomplished by altering the amino acid sequence such that it contains one or more of the above-described tripeptide sequences (for N-linked glycosylation sites). Another type of covalent modification involves chemically or enzymatically coupling glycosides to the antibody. These procedures are advantageous in that they do not require production of the antibody in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, orhydroxyproline, (e) aromatic residues such as those of phenylalanine, tyrosine, or tryptophan, or (f) the amide group of glutamine. For example, such methods are described in WO87/05330.

Removal of any carbohydrate moieties present on the antibody may be accomplished chemically or enzymatically. Chemical deglycosylation requires exposure of the antibody to the compound trifluoromethanesulfonic acid, or an equivalent compound. This treatment results in the cleavage of most or all sugars except the linking sugar (N-acetylglucosamine or N-acetylgalactosamine), while leaving the antibody intact.

Enzymatic cleavage of carbohydrate moieties on antibodies can be achieved by the use of a variety of endo- and exo-glycosidases.

Another type of covalent modification of the antibody comprises linking the antibody to one of a variety of non proteinaceous polymers, eg., polyethylene glycol, polypropylene glycol, or polyoxyalkylenes, in the manner set forth in U.S. Pat. Nos. 4,640,835; 4,496,689; 4,301,144; 4,670, 417; 4,791,192 or 4,179,337. It may be also desirable to modify the antibody of the invention with respect to effector function, e.g. so as to enhance antigen-dependent cell-mediated cytotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing inter-chain disulfide bond formation in this region. The homodimeric antibody thus generated may have improved internalization capability and/or increased complement-mediated cell killing and/or antibody-dependent cellular cytotoxicity (ADCC) (Caron P C. et al. J Exp Med. 1992 Oct. 1; 176(4):1191-5 and Shopes B. J Immunol. 1992 May I; 148(9):2918-22).

Therapeutic Uses of the Antibodies of the Invention

The inventors have demonstrated that some antibodies, like mAbs 20.1 and 7.2, activate the cytolytic function, cytokine production and proliferation of Vγ9/Vδ2 T cells, and thereby may be used to overcome the immunosuppressive mechanisms observed in cancer patients and during chronic infections. Some antibodies costimulate T cells together with CD3-TCR, or costimulate T cells in addition to CD28-B7 costimulation; said antibodies may be used in the same therapeutic applications. Some antibodies increase the survival of monocytes and dendritic cells; said antibodies may be used in the same therapeutic applications.

The invention relates to mAbs 20.1 or 7.2 or a derivative thereof for the use in therapy. The invention relates to mAbs 20.1 or 7.2 or a derivative thereof for use for treating a cancer or a chronic infection.

The invention also relates to a method for treating a cancer or a chronic infection, wherein said method comprises the step of administering to a subject in need thereof a therapeutically effective amount of mAbs 20.1 or 7.2 or of a derivative thereof.

Examples of cancers include, but are not limited to, hematological malignancies such as B-cell lymphoid neoplasm, T-cell lymphoid neoplasm, non-Hodgkin lymphoma (NHL), B-NHL, T-NHL, chronic lymphocytic leukemia (CLL), small lymphocytic lymphoma (SLL), mantle cell lymphoma (MCL), NK-cell lymphoid neoplasm and myeloid cell lineage neoplasm. In a particular embodiment, said hematological malignancy is acute myeloid leukemia (AML).

Examples of non-hematological cancers include, but are not limited to, colon cancer, breast cancer, lung cancer, brain cancer, prostate cancer, head and neck cancer, pancreatic cancer, bladder cancer, colorectal cancer, bone cancer, cervical cancer, liver cancer, oral cancer, esophageal cancer, thyroid cancer, kidney cancer, stomach cancer, testicular cancer and skin cancer.

Examples of chronic infections include, but are not limited to, viral, bacterial, parasitic or fungal infections such as chronic hepatitis, lung infections, lower respiratory tract infections, bronchitis, influenza, pneumoniae and sexually transmitted diseases.

Examples of viral infections include, but are not limited to, hepatitis (HAV, HBV, HCV), herpes simplex (HSV), herpes zoster, HPV, influenza (Flu), AIDS and AIDS related complex, chickenpox (varicella), common cold, cytomegalovirus (CMV) infection, smallpox (variola), Colorado tick fever, dengue fever, ebola hemorrhagic fever, foot and mouth disease, lassa fever, measles, marburg hemorrhagic fever, infectious mononucleosis, mumps, norovirus, poliomyelitis, progressive multifocal leukencephalopathy (PML), rabies, rubella, SARS, viral encephalitis, viral gastroenteritis, viral meningitis, viral pneumonia, West Nile disease and yellow fever.

Examples of bacterial infections include include, but are not limited to, pneumonia, bacterial meningitis, cholera, diphtheria, tuberculosis, anthrax, botulism, brucellosis, campylobacteriosis, typhus, gonorrhea, listeriosis, lyme disease, rheumatic fever, pertussis (Whooping Cough), plague, salmonellosis, scarlet fever, shigellosis, syphilis, tetanus, trachoma, tularemia, typhoid fever, and urinary tract infections.

Examples of parasitic infections include include, but are not limited to, malaria, leishmaniasis, trypanosomiasis, chagas disease, cryptosporidiosis, fascioliasis, filariasis, amebic infections, giardiasis, pinworm infection, schistosomiasis, taeniasis, toxoplasmosis, trichinellosis, and trypanosomiasis. Examples of fungal infections include, but are not limited to, candidiasis, aspergillosis, coccidioidomycosis, cryptococcosis, histoplasmosis and tinea pedis.

mAbs 20.1 or 7.2 or a derivative thereof may be used as a vaccine adjuvant for the treatment of a cancer or a chronic infection.

The invention relates to a vaccine for the treatment of a cancer or a chronic infection comprising mAbs 20.1 or 7.2 or a derivative thereof.

The invention relates to a kit for the treatment of a cancer or a chronic infection comprising:
a) mAbs 20.1 or 7.2 or a derivative thereof; and
b) a vaccine for the treatment of a cancer or a chronic infection.

The two elements of the kit may be administered concomitantly or sequentially over time.

Examples of vaccine for the treatment of a cancer or a chronic infection include, but are not limited to vaccines against viral, bacterial, parasitic or fungal infections such as HIV and HBV and vaccines against viral associated cancers (for instance HPV or HBV) or anti cancer vaccines for instance used to treat patients with melanoma, leukemia, breast cancers, lung cancers.

In a particular embodiment of the invention, the mAbs 20.1 or 7.2 or derivatives thereof can be used in combination with phosphoantigens. Indeed, phosphoantigens have been shown to activate the cytolytic function, the cytokine production and the proliferation of Vγ9/Vδ2 T cells. Without wishing to be bound by theory, it is believed that the use of mAbs 20.1 or 7.2 in combination with phosphoantigens can have a synergistic effect. Phosphoantigens have described in the art. Typically, phosphoantigens include, but are not limited to, the compounds described in international patent applications WO2007057440 and WO2008059052.

Furthermore, the inventors have generated anti-CD277 antibodies, which inhibit the cytolytic function, the cytokine production and the proliferation of Vγ9/Vδ2 T cells. These anti-CD277 antibodies may be used as immunosuppressive agents.

In a further embodiment, the invention relates to an anti-CD277 antibody, which inhibits the cytolytic function, the cytokine production and the proliferation of Vγ9/Vδ2 T cells, for the use in therapy. In particular, the invention relates to an anti-CD277 antibody, the cytolytic function, the cytokine production and the proliferation of Vγ9/Vδ2 T cells, for the treatment of an autoimmune disease, transplantation rejection or a graft versus host disease.

The invention also relates to a method for treating an autoimmune disease, transplantation rejection or a graft versus host disease, wherein said method comprises the step of administering to a subject in need thereof a therapeutically effective amount of anti-CD277 antibody, which inhibits the cytolytic function, the cytokine production and the proliferation of Vγ9/Vδ2 T cells.

Typically the anti-CD277 antibodies, which inhibit the cytolytic function, the cytokine production and the proliferation of Vγ9/Vδ2 T cells, may be mAb 103.2 or a derivative thereof.

Examples of autoimmune diseases which may be treated include but are not limited to rheumatoid arthritis (RA), insulin dependent diabetes mellitus (Type 1 diabetes), multiple sclerosis (MS), Crohn's disease, systemic lupus erythematosus (SLE), scleroderma, Sjogren's syndrome, pemphigus vulgaris, pemphigoid, addison's disease, ankylosing spondylitis, aplastic anemia, autoimmune hemolytic anemia, autoimmune hepatitis, coeliac disease, dermatomyositis, Goodpasture's syndrome, Graves' disease, Guillain-Barre syndrome, Hashimoto's disease, idiopathic leucopenia, idiopathic thrombocytopenic purpura, male infertility, mixed connective tissue disease, myasthenia gravis, pernicious anemia, phacogenic uveitis, primary biliary cirrhosis, primary myxoedema, Reiter's syndrome, stiff man syndrome, thyrotoxicosis, ulceritive colitis, and Wegener's granulomatosis.

Typically an anti-CD277 antibody, which inhibits the cytolytic function, the cytokine production and the proliferation of Vγ9/Vδ2 T cells, may be used in combination with other immunosuppressive and chemotherapeutic agents such as, but not limited to, prednisone, azathioprine, cyclosporin, methotrexate, and cyclophosphamide.

The invention also relates to pharmaceutical composition comprising an antibody of the invention.

Therefore, an antibody of the invention may be combined with pharmaceutically acceptable excipients, and optionally sustained-release matrices, such as biodegradable polymers, to form therapeutic compositions.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

The form of the pharmaceutical compositions, the route of administration, the dosage and the regimen naturally depend upon the condition to be treated, the severity of the illness, the age, weight, and sex of the patient, etc.

The pharmaceutical compositions of the invention can be formulated for a topical, oral, parenteral, intranasal, intravenous, intramuscular, subcutaneous or intraocular administration and the like.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The doses used for the administration can be adapted as a function of various parameters, and in particular as a function of the mode of administration used, of the relevant pathology, or alternatively of the desired duration of treatment. To prepare pharmaceutical compositions, an effective amount of the antibody may be dissolved or dispersed in a pharmaceutically acceptable carrier or aqueous medium. The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

An antibody of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants.

The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride.

Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly concentrated solutions for direct injection is also contemplated, where the use of DMSO as solvent is envisioned to result in extremely rapid penetration, delivering high concentrations of the active agents to a small tumor area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose.

These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

The antibodies of the invention may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered. In addition to the compounds formulated for parenteral administration, such as intravenous or intramuscular injection, other pharmaceutically acceptable forms include, e.g. tablets or other solids for oral administration; time release capsules; and any other form currently used.

In certain embodiments, the use of liposomes and/or nanoparticles is contemplated for the introduction of antibodies into host cells. The formation and use of liposomes and/or nanoparticles are known to those of skill in the art.

Nanocapsules can generally entrap compounds in a stable and reproducible way. To avoid side effects due to intracellular polymeric overloading, such ultrafine particles (sized around 0.1 µm) are generally designed using polymers able to be degraded in vivo. Biodegradable polyalkyl-cyanoacrylate nanoparticles that meet these requirements are contemplated for use in the present invention, and such particles may be are easily made.

Liposomes are formed from phospholipids that are dispersed in an aqueous medium and spontaneously form multilamellar concentric bilayer vesicles (also termed multilamellar vesicles (MLVs)). MLVs generally have diameters of from 25 nm to 4 µm. Sonication of MLVs results in the formation of small unilamellar vesicles (SUVs) with diameters in the range of 200 to 500 A, containing an aqueous solution in the core. The physical characteristics of liposomes depend on pH, ionic strength and the presence of divalent cations.

The invention will further be illustrated in view of the following figures and example.

FIGURES

Figure 1B:
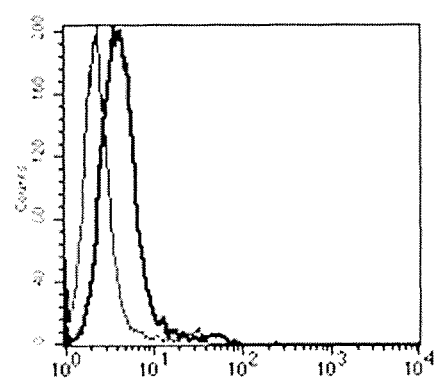
Figure 1C:
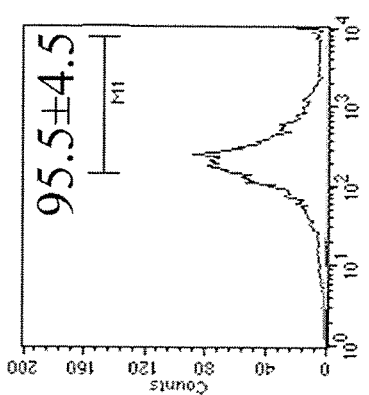
Figure 1D:
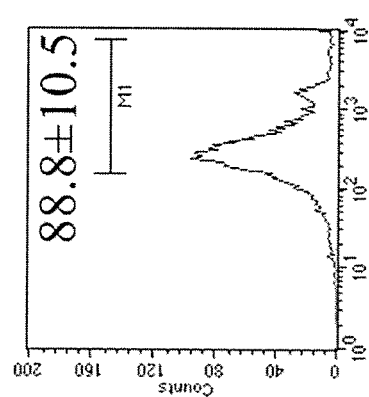
Figure 1E:
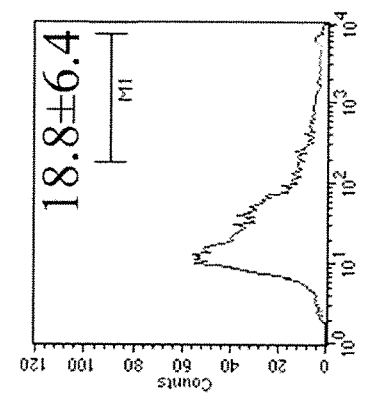
Figure 1F:
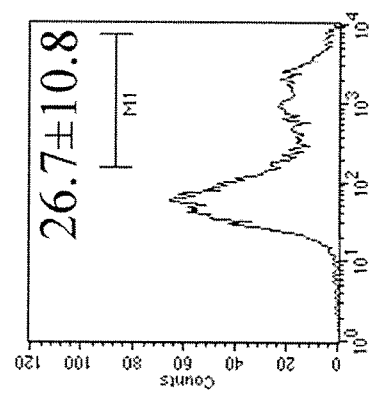
Figure 1G:
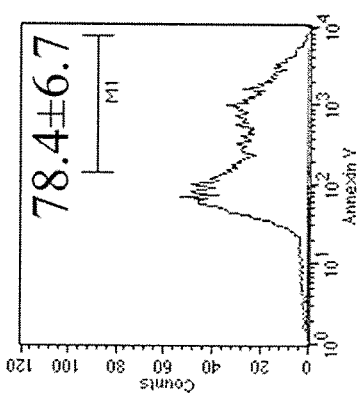
Figure 1H:
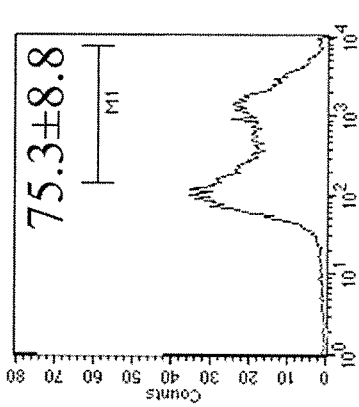
Figure 1I:
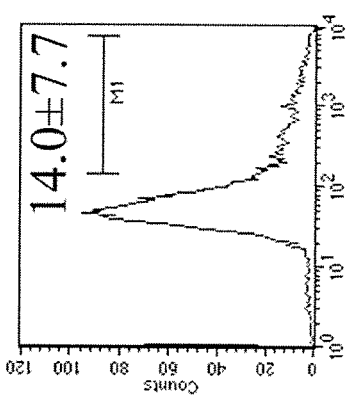
Figure 1J:
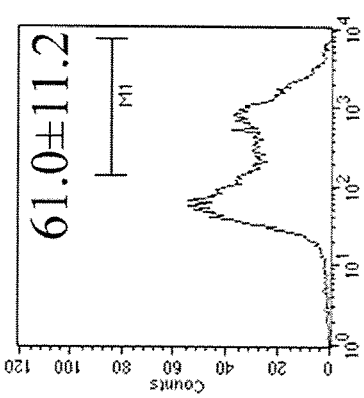

FIGS. 1A and 1B: BT3 receptors are constitutively expressed on the surface of monocytes and iDCs.

The expression on freshly isolated monocytes and iDC using both clone 20.1 anti-BT3 mAb are shown. The experiment shown is representative of five donors studied (the intensity of fluorescence variation among the five experiments was <2%).

FIGS. 1C-1J: BT3 ligation provides a survival signal for monocytes and iDC.

Freshly isolated monocytes (upper row; FIGS. 1C-1F) and iDC (lower row; FIGS. 1G-1J) were stimulated with plastic-coated mAb (anti-CD19, and anti-BT3) or 20 ng/ml GM-CSF as indicated. After stimulation for 72 hours, cells were harvested and analyzed for Annexin V binding, as a marker of apoptotic cells. Numbers in the corners correspond to the percentage of positive cells for Annexin V. Data shown are representative of five independent experiments.

FIGS. 1K-1Z: BT3 engagement increases costimulatory molecules expression on the surface of monocytes.

FIGS. 1AA-1AP: BT3 engagement increases costimulatory molecules expression on the surface of iDC.

Figure 2:
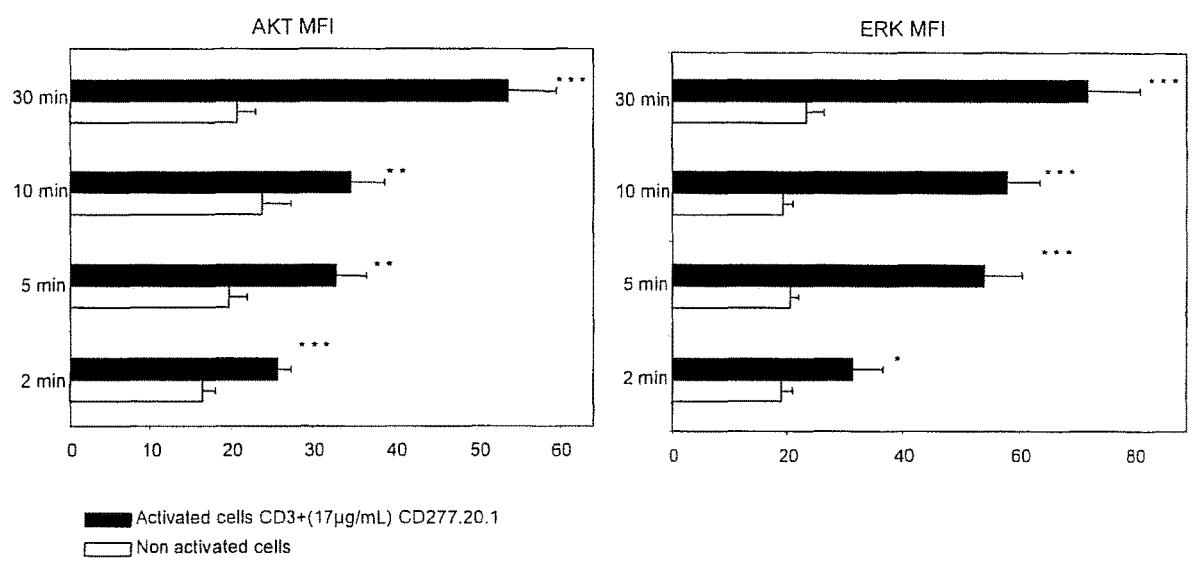

FIG. 2: Regulation of AKT phosphorylation and ERK phosphorylation on CD277 activated CD4+ T cells.

Purified CD4+ T cells from thawed PBMCs from 4 healthy donors stimulated or not with antibody-coated Epoxy dynabeads (1 µg/ml of anti-CD3 plus various concentrations of anti-CD277.20.1 clone or IgG1 (isotype control). Every 2, 5, 10 and 30 minutes, the intracellular phosphorylation of AKT and B, ERK on CD4+ T cells are measured by flow cytometry. Data are representative of four independent studies.

Results are represented as MFI (mean fluorescence intensity expression) on CD4+ T cells at different time points after treatments for 2-30 minutes.

Figure 3:
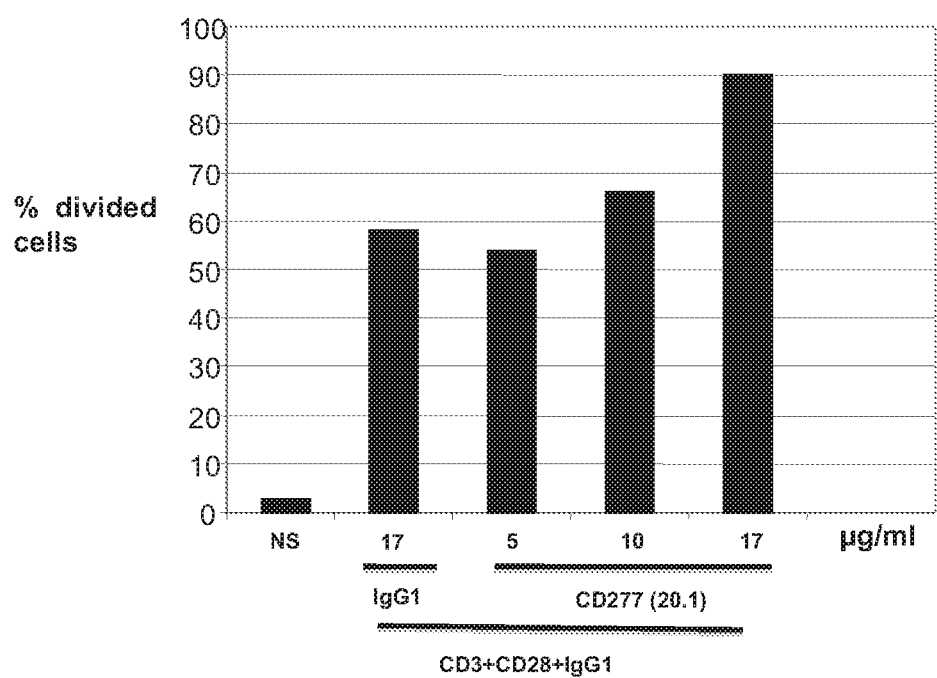

FIG. 3: CD277 is a costimulatory molecule of CD4+ T cells

CD4+ T cells were purified from PBMCs from 4 healthy donors. Purified CD4+ T cells were stimulated with antibody-coated Epoxy dynabeads (1 µg/ml of anti-CD3 and 2 µg/ml of anti-CD28 plus various concentrations of anti-CD277 (20.1) or IgG1 (isotype control) Supernatants were collected on day 2 of culture for cytokine assay by ELISA. INFg, IL-2 and IL-10 production assay.

Figure 4:
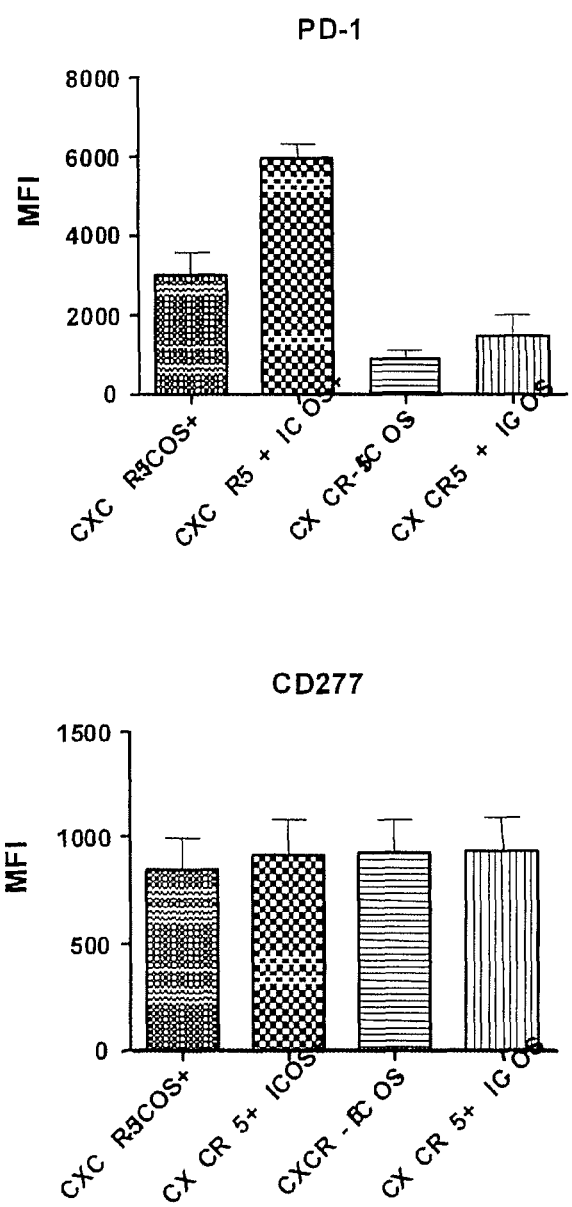

FIG. 4: Expression of CD277 in lymph nodes

Expression profiles of CD277 and PD1 in lymphoid organs. Living T cells from lymphoid tissue are distinguished by staining anti-CD14 (CD14 negative cells) and vivid. T follicular Helper cells were further gated using staining with mAbs CD4, ICOS and CXCR5. Results are presented by MFI (mean fluorescence intensity). Data are representative of 7 independent studies. The p values were calculated using the Mann-Witney paired test to compare differences between CD277 or PD1 expressions on T cells subsets.

*$p<0.05$; $0.001<p<0.01$; *$p<0.001$. $p>0.05$ is not shown.

Figure 5:
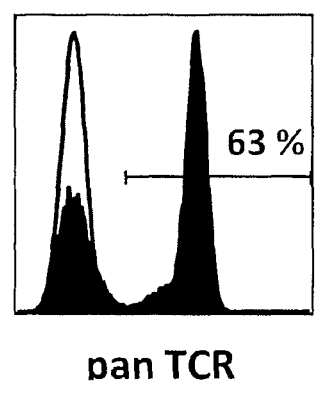
Figure 5:
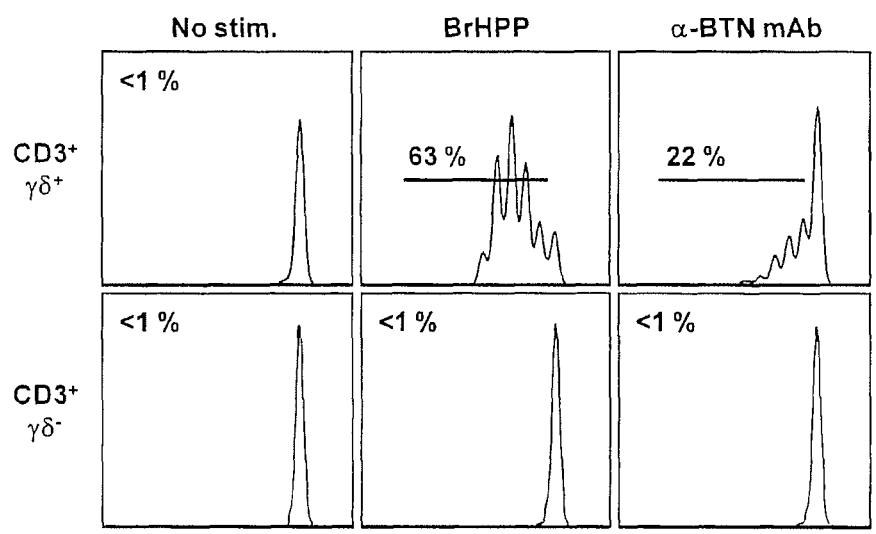

FIG. 5: Anti-CD277 mAb 20.1 stimulates the expansion of Vγ9Vδ2 T cells A: ex vivo expansion (15 days+IL-2): PBMC were stimulated by 20.1 mAb abd IL-2 and Vγ9Vδ2 T cells were monitored by staining with Vγ9Vδ2 T cells specific mAb.

B: CFSE assay (4 days+IL-2): PBMC were stimulated by 20.1 mAb abd IL-2 and Vγ9Vδ2 T cells proliferation was monitored CFSE analysis.

Figure 6:
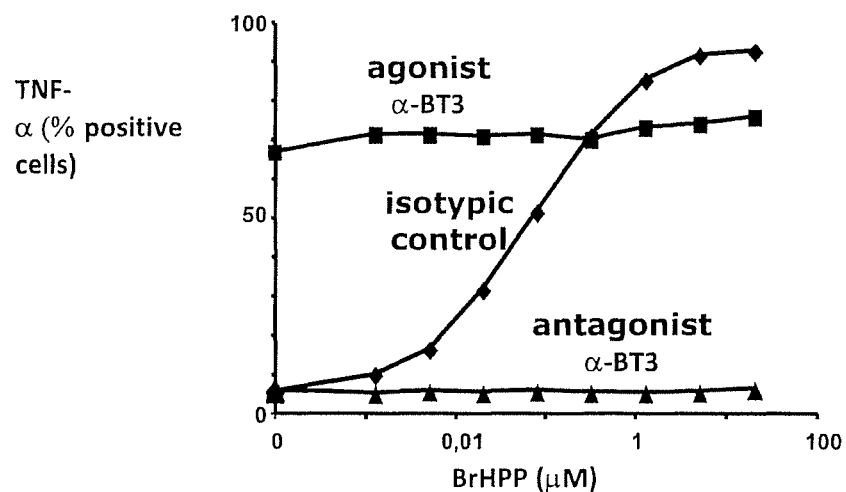
Figure 6:
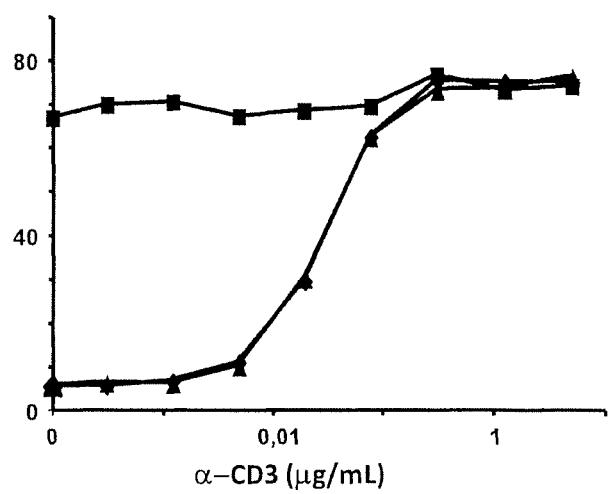
Figure 6:
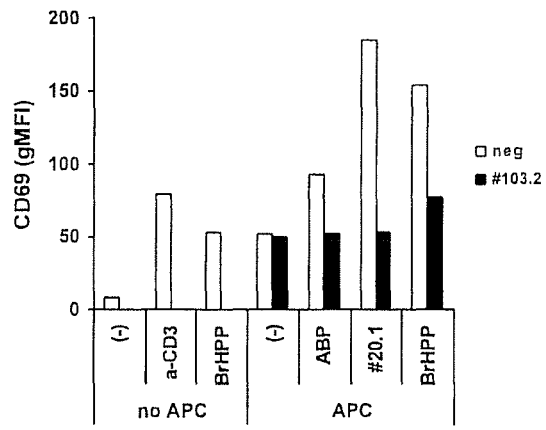

FIG. 6: Activating (20.1) and inhibitory (103.2) CD277 mAbs regulating Vγ9Vδ2 T cells were monitored by staining with Vγ9Vδ2 cells specific mAb.

A: Antagonist CD77 mAb 103.2 inhibits the phosphoantigen mediated activation of Vγ9Vδ2

B: Antagonist CD77 mAb 103.2 does not inhibit the CD3 mediated activation of Vγ9Vδ2

C: 103.2 BTN3 mAb inhibits phosphoantigen-induced activation of Jurkat TCR Vγ9/Vδ2 T cells as determined by CD69 expression.

Figure 7:
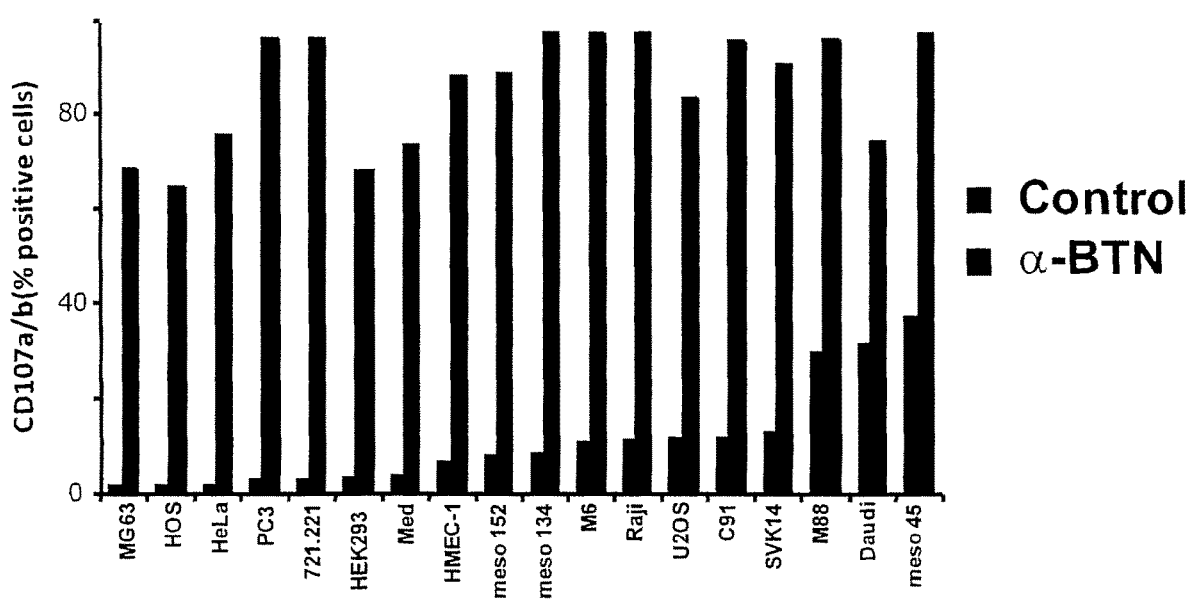

FIG. 7: CD277 potentiate the anti-tumor cytolysis mediated by Vγ9Vδ2 T cells Tumor cell lines were incubated with Vγ9Vδ2 with or without 20.1 agonist mAb. The activation of Vγ9Vδ2 was evaluated by CD107a/b degranulation.

Figure 8:
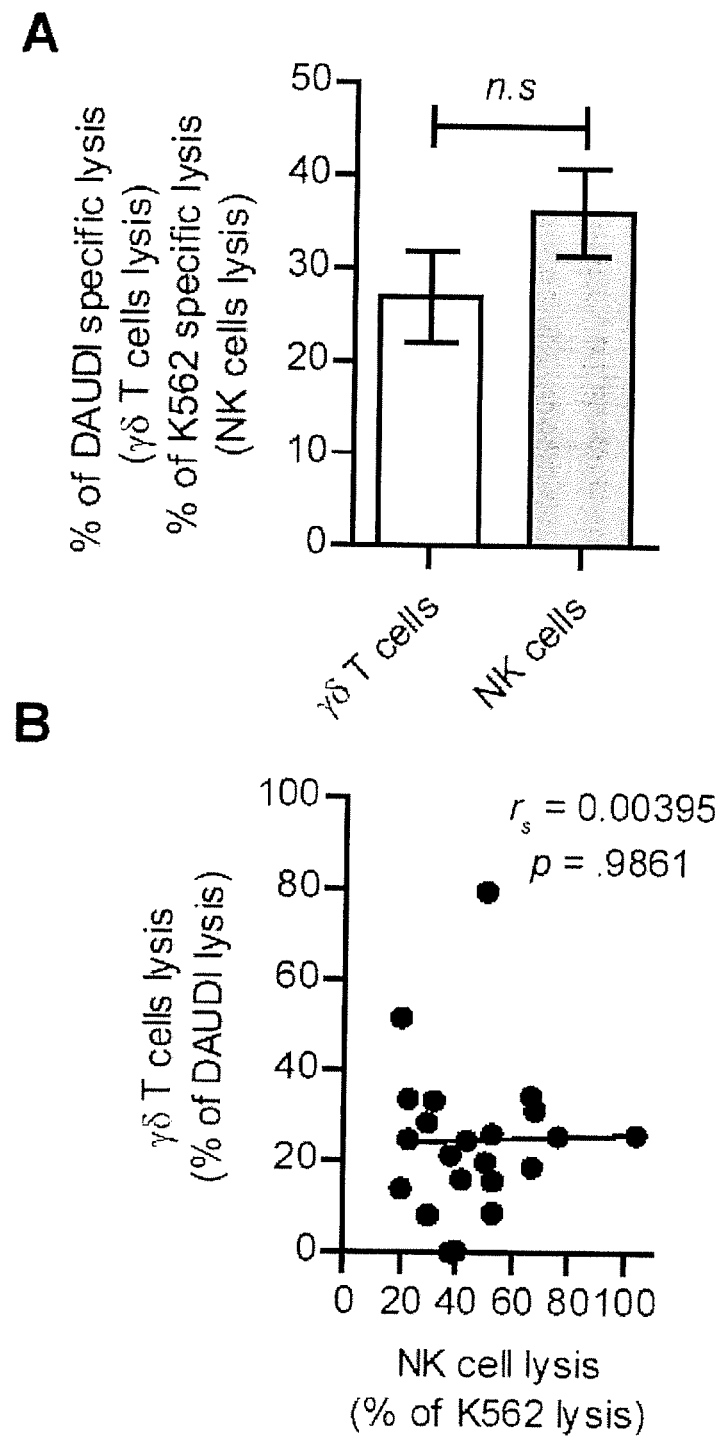

FIG. 8: Comparison of NK cells and VI/9M T cells cytotoxicity against primary AML blasts (A) Comparison of the cytotoxic activity of expanded Vγ9Vδ2 T cells from allogeneic HV (n=3-5) and sorted NK cells from allogeneic HV (n=8) against primary AML blasts (n=6) in a standard [$^{51}$Cr]-release assay. Data are shown for E:T 10:1. The lysis is normalized to the percentage of DAUDI and K562 cell lines specific lysis respectively for γδ T cells and NK cells. Results were expressed as percentage±SEM. Statistical significance was established using Mann Whitney test. $p>0.05$=n.s=non significant. (B) Linear regression of the level of specific lysis of primary AML blasts (n=22) by expanded Vγ9Vδ2 T cells from allogeneic HV (n=3-8) and IL2-plus-IL15-activated NK cells from allogeneic HV (n=3-8) in a standard [$^{51}$Cr]-release assay. Data are shown for E:T 30:1 for Vγ9Vδ2 T cells and 15:1 for NK cells. The lysis is expressed as the mean percentage of specific lysis of DAUDI and K562 cell lines and correlation was established using the nonparametric Spearman correlation coefficient ($r_s$). $p>0.05$=n.s=non significant.

Figure 9:
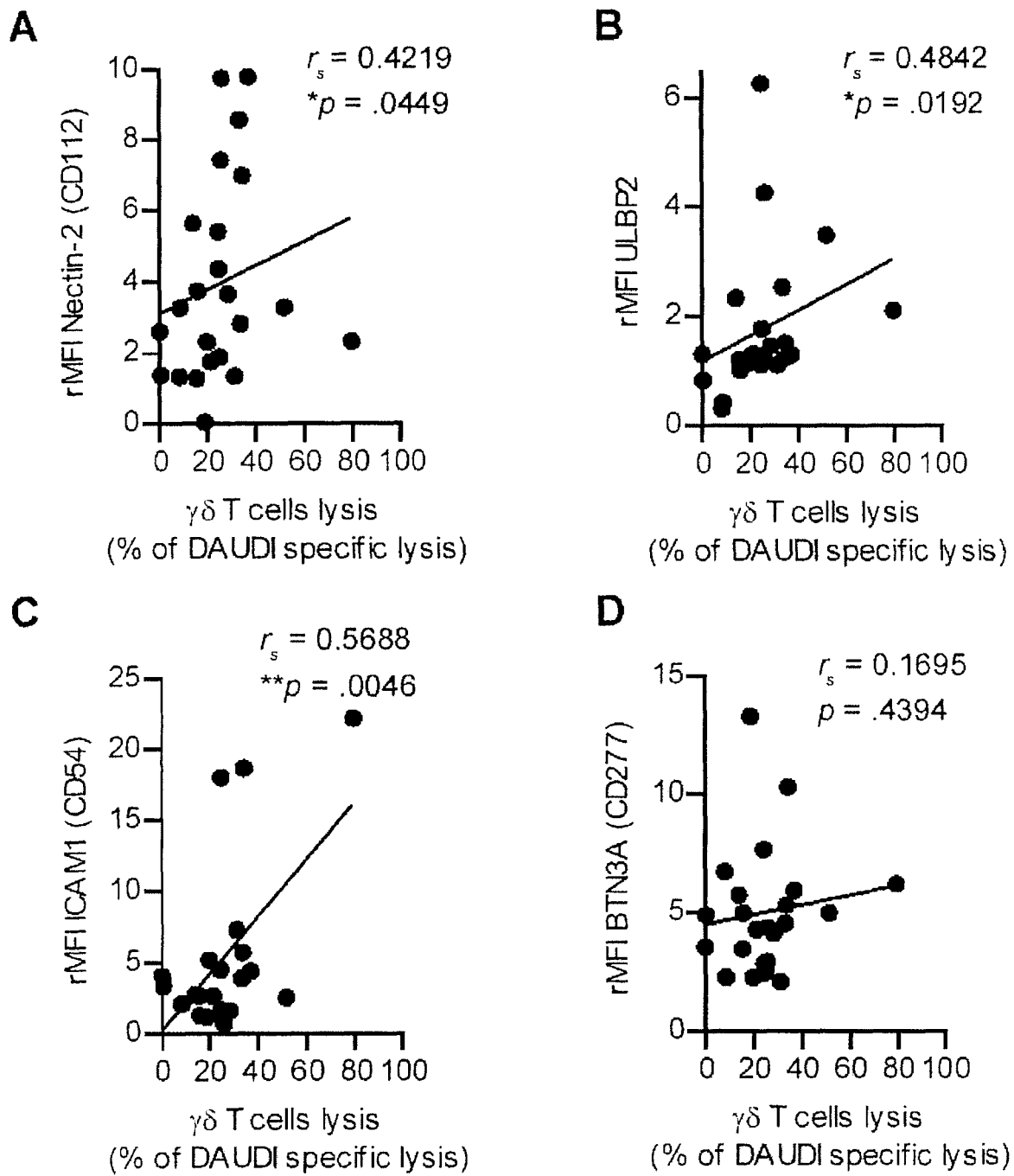

FIG. 9: Correlation between expression of activating molecules on primary AML blasts and their lysis by Vγ9Vδ2 T cells. Linear regression of normalized AML blasts lysis (n=23) by Vγ9Vδ2 T cells compared to the level of expression of (A) Nectin-2, (B) ULBP2 (C) ICAM1 and (D) BTN3A. The surface expression was assessed by Flow Cytometry analysis. The results are expressed as Median Fluorescence Intensity ratio (rMFI) compared to Isotype control. The lysis is expressed as the mean percentage of specific lysis of DAUDI and K562 cell lines. Correlations were established using the nonparametric Spearman correlation coefficient ($r_s$). $p>0.05$=ns=non significant, *$p<0.05$; **$0.001<p<0.01$.

Figure 10:
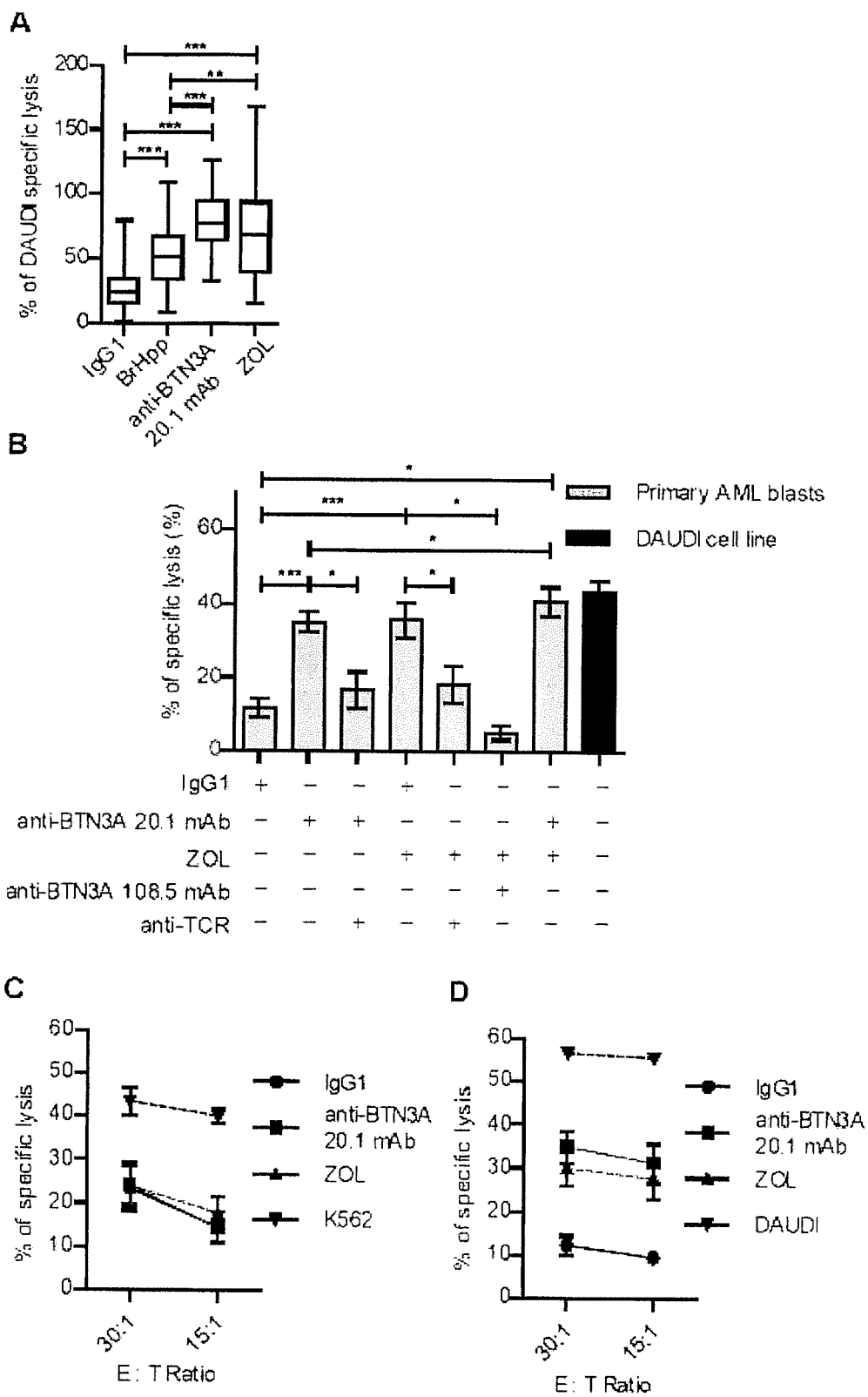

FIG. 10: Specific BTN3A-mediated enhancement of Vγ9Vδ2 T cells lysis of primary AML blasts by TCR agonists. AML blasts were pre-incubated for 1 hour with Control Isotype, BrHpp (2 µM) anti-BTN3A agonist 20.1 mAb (10 µg/ml) or O/N with ZOL (45 µM), before addition of Vγ9Vδ2 T cells (A) Comparison of TCR agonists. Specific lysis of primary AML blasts (n=25) by expanded Vγ9Vδ2 T cells from HV (n=3-9) after treatment with BrHpp, ZOL, or anti-BTN3 mAb (20.1). Data are shown for E:T 30:1. The lysis is expressed as percentage of specific lysis of DAUDI cell line. (B) Effect of TCR and BTN3A blocking. Primary AML blasts lysis (n=11) by expanded Vγ9Vδ2 T cells from HV (n=3-9). Vγ9Vδ2 T cells (n=1-6) were pre-incubated for 30 min with anti-TCR mAb. The blasts were treated with ZOL, agonist (20.1) or antagonist (108.5) anti-BTN3A mAb or combination. Data are shown for E:T 30:1. The lysis is expressed as percentage of specific lysis and compared to DAUDI specific lysis. (C, D) Effect of anti-BTN3A mAb and ZOL on NK cells lysis compared to Vγ9Vδ2 T cells Representative data from 2 independent experiment. Primary AML blasts lysis (n=3) by (C) NK cells from HD (n=3) isolated and treated O/N with IL2; (D) Expanded Vγ9Vδ2 T cells from HD (n=3). K562 and DAUDI were used as positive controls respectively for NK cells and Vγ9Vδ2 T cells lysis. The lysis is expressed as percentage of specific lysis. Results were expressed as mean±SEM and statistical significance was established using the non-parametric paired Wilcoxon U-test. *$p<0.05$; $0.001<p<0.01$; *$p<0.001$.

Figure 11:
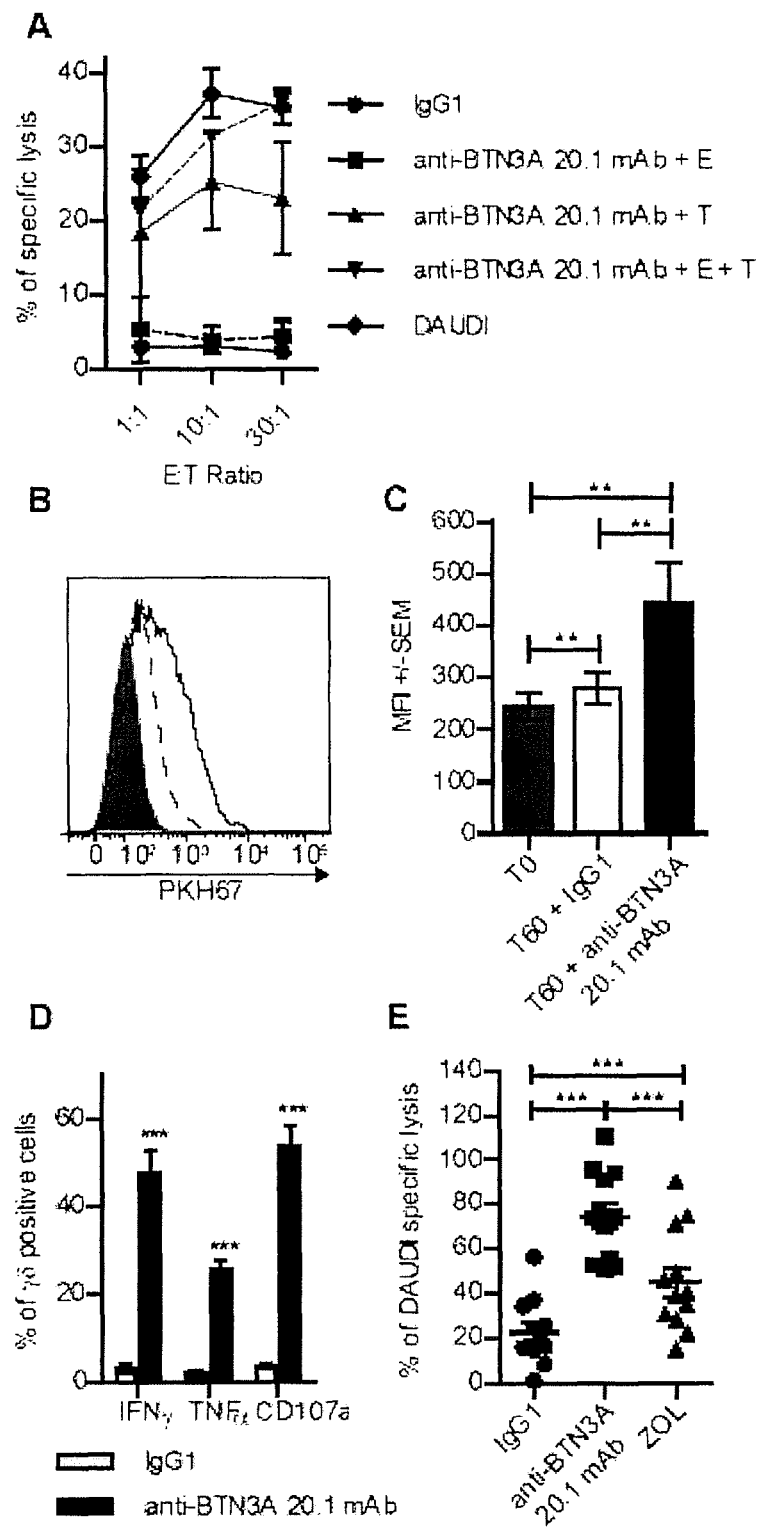

FIG. 11: Triggering of BTN3A on primary AML blasts with mAb enhances their recognition by Vγ9Vδ2 T cells and bypasses N-BP-resistance. (A) Primary AML blasts, target (T) lysis (n=2) by Effector (E) Vγ9Vδ2 T cells from HV (n=2) with IgG1 (full black line) or i) after T pre-incubation with anti-BTN3A 20.1 mAb (anti-BTN3A+T) (full grey line) or ii) after simultaneous incubation of E, T and anti-BTN3A 20.1 mAb (anti-BTN3A+E+T) (dashed grey line), or iii) after E pre-incubation with anti-BTN3A 20.1 mAb (anti-BTN3A+E) (dashed black line). T or E cells were preincubated for 90 minutes with anti-BTN3A 20.1 mAb (10 µg/ml), and then extensively washed before E+T co-culture. Representative data from 2 independent experiments. Data are shown for E: T 1:1, 10:1, 30:1. The lysis is expressed as a mean percentage of specific lysis±SEM and compared to DAUDI lysis. (B) Representative experiment showing trogocytosis of AML blasts from patient UPN01 by Vγ9Vδ2 T cells from HV (full grey histogram) and after 1 hour in co-culture with IgG1 (dashed line) or anti BTN3A 20.1 mAb (full line). (C) Vγ9Vδ2 T cells trogocytosis (PKH67 MFI±SEM) of AML blasts (n=10). Cumulative data at 0 and 60 min from 3 different experiments. (D) CD107a expression, TNF☐ and IFN☐ production by Vγ9Vδ2 T cells from HV after a 4-hour co-culture with AML blasts (n=6). (E) Specific lysis of N-BP-poorly sensitized AML blasts (n=13) by Vγ9Vδ2 T cells from HV (n=3-9) after treatment with IgG1, ZOL (O/N, 45 µM), or anti-BTN3A 20.1 mAb. Data are shown for E:T 30:1. The lysis is expressed as percentage of DAUDI specific lysis. Results were expressed as mean±SEM and statistical significance was established using the non-parametric paired Wilcoxon U-test. *p<0.05; 0.001<p<0.01; *p<0.001.

Figure 12:
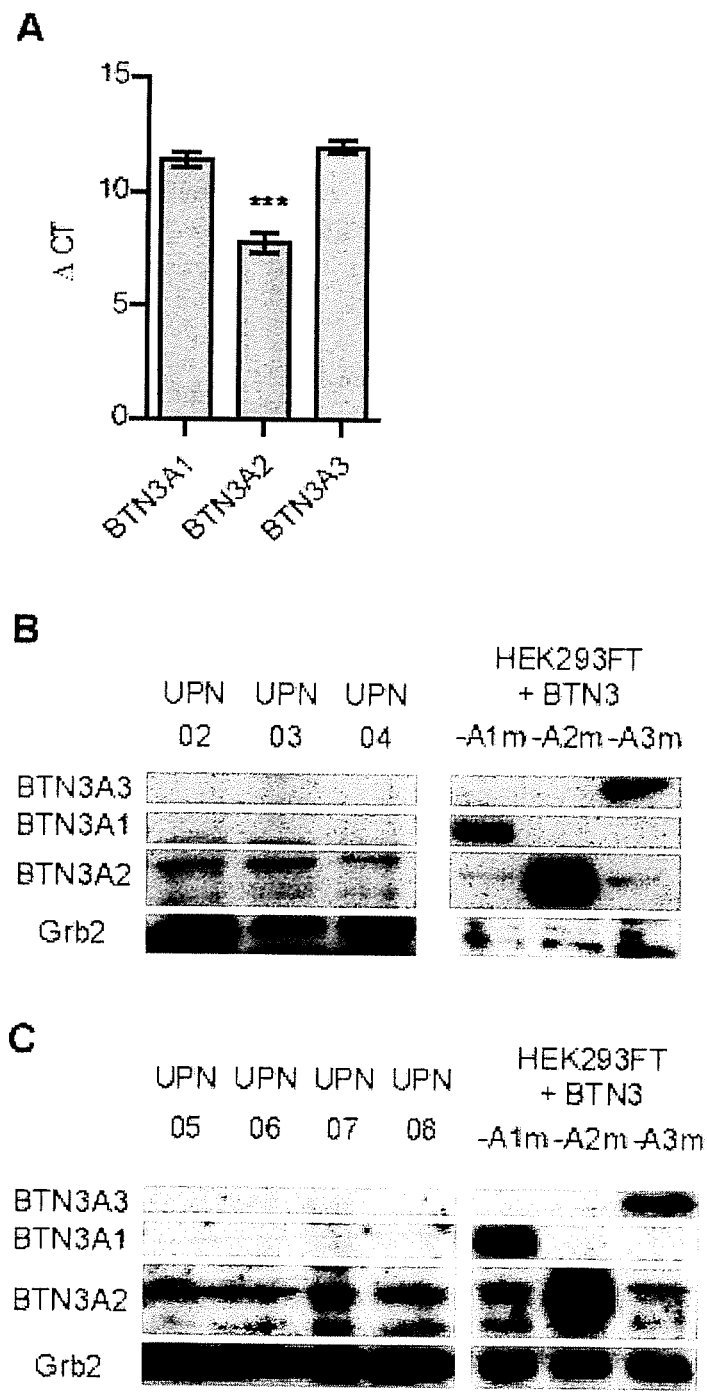

FIG. 12: Primary AML blasts mainly express BTN3A2 isoform irrespectively of their sensitivity to N-BP. (A) qRT PCR analysis of total RNA isolated from primary AML blasts (n=20). Datas were normalized using GAPDH as endogenous control ($\Delta Ct = Ct_{target\ gene} - Ct_{GAPDH}$). Statistical significance was established using the non-parametric paired Wilcoxon U-test. ***p<0.001 (B) (C) Western-blot analysis of total protein extracts from primary AML blasts poorly (B) or well sensitized by ZOL (C). BTN3A knock-down HEK293FT (sh #284; clone #30) transiently transfected with BTN3A1m, BTN3A2m, BTN3A3m are used as size controls. Extracts were loaded in 10% SDS PAGE gel and membranes were hybridized with anti-BTN3A 20.1 mAb and anti-Grb2 as a loading control.

Figure 13:
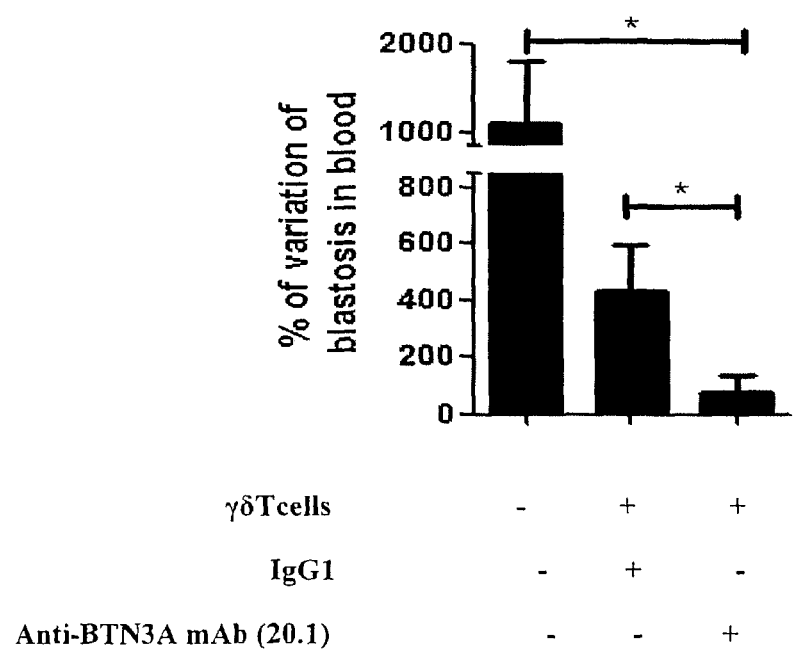

FIG. 13: Evaluation of anti-BTN3A agonist 20.1 mAb anti-leukemic activity in vivo in an AML xenograft model. NSG mice (n=23) were intravenously injected with primary AML blasts. Since the Week 8 post-graft, they were treated twice a week during two weeks with injections of 15×10$^6$ Vγ9Vδ2 T cells and either anti-BTN3A mAb (n=8) or IgG1 (n=8). Control mice were injected with PBS (n=7). Mice were sacrificed at the Week 11 post-graft. Percentage of variation of the absolute number of blasts in blood quantified by Glow Cytometry before and 4 days after the end of treatment. Representative and cumulative data from 2 independent experiments. Mean Whtney test was used to compare differences between treatments. *p>0.05

EXAMPLE 1

Materials and Methods
Cell Cultures

Blood samples were obtained from 5 healthy volunteers enrolled among the staff members, after informed consent. Monocytes were separated from peripheral blood mononuclear cells, and isolated using the MACS CD14 isolation kit (Miltenyi Biotech, Auburn, Calif. USA). Monocytes were cultured for 5 days with 200 ng/ml of recombinant human GM-CSF and 10 ng/ml recombinant human IL-4 (Schering-Plough Research Institute). These cells were termed immature dendritic cells (iDC). To achieve the stimulation, monocytes and iDC were cultured with 10 ng/ml of LPS, ligand for TLR4, 30 µg/ml of 8848 (Sigma-Aldrich, Milano, Italy), ligand for TLR7/8 and with 2.5 mg/ml of poly (I:C) (Sigma-Aldrich), ligand for TLR3, and were harvested after 48 h. The cells were cultured in RPMI 1640 supplemented with 10% heat-inactivated FCS, 5 mM L-glutamine and 50 IU/ml penicillin-streptomycin (from here on referred to as complete medium).

Flow Cytometry and Antibodies

Monocytes and iDCs before and after stimulation were analysed by immunofluorescence flow cytometry (FAC-Scalibur Becton Dickinson, Milano, Italy) to verify their activation state. To this end, mAb specific for CD80, CD86, HLA-DR, CD1a, CD14 (BD Becton Dickinson), BT3 (clone 20.1, IgG1) and BT3 Fab$_2$ were previously selected, purified and characterised (Bensussan and Olive, 2005, Compte et al., 2004) or irrelevant molecules (anti-CD19, Becton Dickinson, and anti-CD31, clone Moon-1, provided by F. Malavasi, both IgG1) were used. All the available anti-BT3 mAbs are unable to discriminate among the three members of this family (BT3.1, BT3.2, or BT3.3), probably due to their high sequence homology (Compte et al., 2004, Bensussan and Olive, 2005). As further control, to block the possible effect of trace amounts of endotoxin, polymyxin B (10 µg/ml, Sigma-Aldrich) was added to the anti-BT3 mAb 20.1 before adding the cells.

As loading control for Western blot analyses, anti-tubulin mAb (clone: 6-11B-1, IgG1, Invitrogen, Milano, Italy) was used.

Apoptosis Detection

Monocytes and iDC were cultured on plastic coated with anti-BT3 mAb (clone 20.1) or with isotype-matched irrelevant mAb. As control, the cells were stimulated with 20 ng/ml recombinant human GM-CSF (Schering-Plough Research Institute). After three days, cells were harvested, stained with Annexin V-FITC (Bender MedSystems, Wien, Austria) and analysed by flow cytometry.

Quantitative RT-PCR qRT-PCR analysis was performed with the Applied Biosystems 7900HT Fast Real-Time PCR system using Taqman detection. Briefly, total RNA was isolated from THP-1 cells using the standard TRIzol reagent protocol (Invitrogen Life Technologies). 2 µg of the obtained RNA was reverse transcribed using oligo(dT). Each PCR assay was performed in a 25 µl reaction containing 2× TaqMan universal Mix (Applied Biosystems) reagent, 20× primers and 2 µl cDNA (equivalent to 40 ng of total RNA). Thermal cycle conditions were 95° C. for 15 s and 60° C. for 60 s (40 cycles). Capture of fluorescence was recorded on the ABI Prism 7900HT scanner and the Ct (threshold cycle) was calculated for each assay (Sequence Detection System Software 2.3, Applied Biosystems). Data are normalized using GAPDH as endogenous control ($\Delta Ct = Ct_{target\ gene} - Ct_{GAPDH}$). A higher $\Delta Ct$ correspond to a lower expression of the analysed gene. BT3.1, BT3.2, BT3.3 and GAPDH TaqMan Gene Expression assays were purchased from Applied Biosystems.

Statistical Analyses

Statistical analysis was performed by GraphPad Prism4 software 4.0 (GraphPad Software Inc., CA, USA) using the Student's t test. For the evaluation of cytokine production, data were analyzed with one-way analysis of variance (ANOVA). For the evaluation of apoptosis induction, data were analyzed with a non-parametric test. The significance level was set at P<0.05.

Results

BT3 Receptors are Constitutively Expressed on the Surface of Monocytes and iDCs.

In order to investigate the expression of BT3, we chose a panel of healthy donors to obtain monocytes and iDC. BT3 expression was evaluated on freshly isolated monocytes and iDC using clone 20.1 anti-BT3 mAb (FIGS. 1A and 1B). FIGS. 1A and 1B shows BT3 expression on freshly isolated monocytes and iDC using clone 20.1 anti-BT3 mAb. The differentiation of monocytes in DC was verified by expression of cell surface markers: CD14 was down-regulated and remained low in both immature and mature DC, whereas CD1a and HLA-DR was up-regulated (data not shown). The experiment shown is representative of five on different donors. The level of expression of BT3 was slightly higher on monocytes. In addition, we analysed the expression of BT3 following stimulation of these cells with LPS, poly (I:C) and R848, ligands for TLR4, TLR3 and TLR7/8, respectively. The activation via TLR (Toll Like Receptors) did not significantly alter the cell surface expression of BT3 (data not shown). We can derive that BT3 receptors are constitutively expressed on the surface of monocytes and iDC, independently on their activation state.

Finally, the qRT-PCR analysis confirmed the immunophenotypic results showing that all the three receptors of the BT3 family are expressed by THP-1 cells. In detail, we found BT3.2 as the most represented one (ten times more BT3.2 than BT3.1 and BT3.3) (data not shown).

BT3 Ligation Provides a Survival Signal for Monocytes and iDC in Culture.

As BT3 is a stably expressed receptor family, we investigated the ability of BT3 engagement to modify the life span of ex vivo monocytes and iDC cultured in the absence of survival factors (i.e. completed medium with serum) for 72 hours. Cell stimulation by plastic-coated mAb was used to engage BT3 on the surface of monocytes and iDC. Approximately 77.98% of monocytes treated with the mAb specific for BT3 survived in the absence of endogenous survival factors for 3 days (range 51.13-77.98%, p=0.0040) (FIGS. 1C-1F, upper row, shows a representative experiment of five). This effect was slightly lower than that obtained by GM-CSF treatment (81.22%, range 60.41-83%, p=0.0278). In control cultures, i.e. in the presence of plastic-coated irrelevant mAb (anti-CD19 mAb), the survival effect was minimal and a very high proportion of apoptotic monocytes (Annexin-V-positive cells) was observed (about 95.48% of apoptotic cells was measured in medium alone and about 88.79% in plastic-coated irrelevant mAb condition, survival range 0.8-11.74% and 1.08-11.21% respectively, p N.S.). Similar results were obtained by analysing the effect on iDC survival (FIGS. 1G-1J, lower row, shows a representative experiment of five). Activation of iDC via BT3 was able to partially inhibit iDC apoptosis during a 72-h culture period (56.75% of healthy-vital cells versus 85.97% in the survival GM-CSF treatment, range 53.13-60.71%, p=0.00044, and 71.01-85.97%, p=0.0040 respectively). Irrelevant isotype-matched mAb did not alter the naturally occurring apoptosis of DC (if we compare medium alone and anti-CD19 mAb condition of a representative experiment of five, range 0.8-24.12% and 0.9-26.97% of surviving cells respectively, p=0.3452). Altogether, these results suggest that BT3 receptors are able to promote monocytes and iDC survival and to extend the duration of cells responses by attenuating apoptosis. For both cell types, the survival differences following anti-BT3 versus control isotype-matched mAb was statistically significant (as for GM-CSF treatment). In addition, a dose response effect of anti-BT3 mAb on survival of both monocytes and iDC is apparent (data not shown). The lowest anti-BT3 mAb dilution able to promote a good survival capability was 10 µg/ml.

BT3 Engagement Increases Costimulatory Molecules Expression on the Surface of Monocytes and iDC.

To investigate the role of BT3 in primary inflammatory responses, freshly isolated blood monocytes and monocyte-derived dendritic cells were stimulated by mAb, coated on tissue culture plates, or by TLR ligands known to stimulate monocytes and dendritic cells (LPS). After 24 h stimulation, coated anti-BT3 mAb was able to trigger the activation of monocytes, as shown by up-regulation of the cell surface costimulatory molecule CD86 (FIGS. 1K-1Z). The isotype-matched control mAb (whose antigen is not expressed on these cells), had no significant effect. Thus, the activation observed using anti-BT3.1 mAb was specific and not due to the engagement of FcR. Cross-linking was required for cellular activation, because no effect was observed with non-coated (soluble) anti-BT3 mAb (data not shown). In addition, the activating effect of anti-BT3 mAb was maintained in the presence of polymyxin B, thus excluding the role of trace levels of endotoxins.

Interestingly, CD86 up-regulation upon BT3 stimulation was similar to that observed with TLR ligand LPS. BT3 stimulation also triggered up-regulation at the monocyte surface of CD80 and HLA-DR molecules (FIGS. 1K-1Z). Consistently, we found increased expression of CD80, CD86 and HLA-DR on iDC (FIGS. 1AA-1AP). In addition, similar results were obtained using anti-BT3 Fab mAb (as can be depicted from FIGS. 1K-1Z and 1AA-1AP on monocytes and DC respectively). These results allow us to rule out that a signal through FcRs cannot be responsible of cells activation. The irrelevant mAb (anti-CD19) was a negative control, whereas stimulation via TLR4 ligand for LPS was a positive control.

EXAMPLE 2

Materials and Methods

Cell Preparation

Peripheral blood mononuclear cells (PBMCs) were obtained from healthy volunteer donors provided by the "Etablissement Français du Sang" (EFS-Marseille-France) and isolated by fractionation over a density gradient of Lymphoprep© (Abcys). Human $CD4^+$ T cells were negatively selected from isolated PBMCs by depletion of non-$CD4^+$ T cells with magnetic beads using the T cell isolation kit II from Miltenyi Biotec®. Isolated CD4 cells were used for further experiments when purity was superior to 90%.

Generation of Monoclonal Antibodies (mAbs)

The mouse anti-human programmed death-1 (PD-1) mAB and three different clones of mouse anti-human CD277 were purified from ascites in our laboratory: Anti-PD-1 (clone PD1 3.1 with an IgG1 isotype) (ghiotto et al. Int Immunol., 2010), Anti-CD277 (clone 103.2 with an IgG2a isotype, clones 20.1 and 7.2 both with an IgG1 isotype) (compte et al.). The anti-CD277 (clone 20.1) mAb was labelled with Alexa Fluor 647 using a commercial kit (Invitrogen, Eugene, Oreg.).

Expression Profile of CD277 on T Cells Subpopulations

Thawed human PBMCs from four healthy donors were stained with 5 µl of the following mouse anti-human monoclonal antibodies per million of cells: ECD-conjugated anti-CD3, PC5-conjugated anti-CD14, PC5-conjugated anti- CD19 (to select CD3⁺CD14⁻CD19⁻ cells) (all from Beckman Coulter, Marseilles, France), Pacific Blue-conjugated anti-CD4, Alexa700-conjugated anti-CD8 (all from BD Pharmingen (San Diego, USA)), APC-Alexa750-conjugated anti-CD27 (from Caltag, Invitrogen, USA), PC7-conjugated anti-CD45RA (from BD Biosciences), Alexa647-conjugated anti-CD277 (clone 20.1, homemade). APC-conjugated IgG1 (Beckman Coulter) was used as control and LIVE/DEAD Fixable Dead Cell Stain Kit was used for viability. Cells were incubated 20 minutes at 4° C. then washed twice in phosphate-buffered saline (PBS, Lonza) fixed with 2% paraformaldehyde, and analyzed on a FACSAria flow cytometer (BD Biosciences). Data were analyzed using FlowJo Software (TreeStar, Ashland, Oreg.).

Kinetic of CD277's Expression Profile on Naive CD4⁺ T Cells

Purified CD4⁺ T cells (200×10³ cells/well) from thawed human PBMCs were cultured during 96 h in RPMI 1640 10% FBS in flat bottom 96-well plates (Microtest™ 96, Becton Dickinson) with previously plate-immobilized mouse anti-human CD3/CD28 or not (unstimulated). Anti-CD3 (clone OKT3) and anti-CD28 (clone CD28.2, homemade) were used at 0.3 µg/ml and 10 µg/ml respectively. Cells were placed into an atmosphere of 5% $CO_2$ at 37° C. in a humidified incubator. Every 24 h cells were transferred in a conic bottom 96-well plate (Nunc™, Denmark) and stained with the following mAbs 30 minutes at 4° C.: 3 µl of purified anti-PD-1 (clone PD-1 3.1, home-made) (giotto et al, int immunol. 2010), washed 3 times in PBS-FBS 0.2%-azide 0.02%, then stained with PE-conjugated goat anti-mouse (1/80, Beckman Coulter), washed and stained with 3 µl of each following mAbs 30 minutes at 4° C.: PC7-conjugated anti-CD4, FITC-conjugated anti-CD3 (all from BD Biosciences) Alexa647-conjugated anti-CD277 and 6 µl of 7-AAD (BD Biosciences) for viability. Purified IgG1 or APC-conjugated IgG1 were used as controls. Immunostained cell samples fixed with 2% paraformaldehyde were analyzed on a BD FACS Canto (BD Bioscience). Data were analyzed using FlowJo Software (TreeStar, Ashland, Oreg.).

Expression of CD277 in Lymph Nodes

Cells teased from lymph nodes were collected from 7 patients who had given informed consent. Mononuclear cells were obtained by crushing fresh tissue samples in RPMI 1640 10% FBS. Detection of Folliculat T Helper cells ($TF_H$) cells was performed by incubation for 20 minutes at 4° C. with PE-conjugated anti-ICOS, biotinylated anti-CXCR5 (all from BD Biosciences), PC5-conjugated anti-CD14, Pacific blue-conjugated anti-CD4 (all from Beckman Coulter) and LIVE/DEAD Fixable Dead Cell Stain Kit©. Cells were then washed in PBS and incubated with anti-biotin-allophycocyanin-Alexa Fluor 750 (Invitrogen, Carlsbad, Calif.) for 20 minutes at 4° C. After staining, each cell preparation was washed twice in PBS, fixed with 2% paraformaldehyde, and analyzed on a FACSAria flow cytometer (BD Biosciences). Data were analyzed using FlowJo Software (TreeStar, Ashland, Oreg.).

Expression Profile of CD277 on NK Cells

Thawed alive NK cells (Live Dead© negative cells) were selected based on the expression of CD56+CD3− from healthy human PBMCs after 20 minutes incubation at 4° C. with the anti-CD277-Alexa647 (clone 20.1). Cells were further washed twice in PBS (PBS, Lonza), then fixed with 2% formaldehyde and analyzed on a FACSAria© flow cytometer (BD Biosciences). Data were analyzed using FlowJo Software (TreeStar, Ashland).

Functional Assays on CD4+ T Cells Using Plate-Immobilized mAbs

Purified CD4⁺ T cells (200×10³ cells/well) from thawed human PBMCs were cultured in RPMI 1640 10% FBS in flat bottom 96-well plates (Microtest™ 96, BD) with previously plate-immobilized mouse anti-human CD3 (clone OKT3)/CD28 (clone CD28.2) or anti-CD3/anti-CD277 (clone 20.1) or anti-CD3/isotypic control (IgG1). Purified anti-CD3 was used at 0, 3 µg/ml. Anti-CD28, anti-CD277 and isotypic control were used at 10 µg/ml. Cells were placed into an atmosphere of 5% $CO_2$ at 37° C. in a humidified incubator. After 2 days of culture, cytokines production (Interleukine-2, IL-2 and Interferon gamma, IFN-γ) was measured by ELISA assay according to the manufacturer's protocol (OptEIA, human IFN-γ or IL-2 Set, BD Pharmingen). After 5 days, cells were stained with 3 µl of PE-conjugated anti-CD25 (BD Biosciences), and 5 µl of 7-AAD for 30 minutes at 4° C. then washed twice in PBS, fixed with 2% paraformaldehyde and analyzed on a BD FACS Canto (BD Bioscience). Data were analyzed using FlowJo Software (TreeStar, Ashland, Oreg.).

Functional Assay on CD4+ T Cells with aAPC and Carboxyfluorescein Diacetate Succinimidyl Diester (CFSE) Labeling Human CD4⁺ T cells were purified by negative selection from PBMCs using magnetic beads (Miltenyi Biotec) according to the manufacturer's protocol. CD4+ T cells were routinely more than 97% pure.

CD4⁺ T cells were labelled with 0.5 µM CFSE (Invitrogen) for 10 min at 37° C., washed and stimulated (1.5×10⁵ cells/well) with aAPC at a ratio of 1:1 (cells to beads) comprised of magnetic beads in triplicate in 96-well round-bottom plates (Falcon; BD Biosciences). Cultures were incubated at 37° C., 5% CO2 for 5 days and then proliferation of CFSE labelled CD4⁺ T cells were measured by flow cytometry (FACS Canto, Beckman Coulter).

Functional Assay on NK Cells, Cytolytic Activity.

Fresh NK cells were sorted with Easy Sep® negative selection kit and incubated over night in medium completed with sub-optimal concentrations of IL-2 (100 U/ml) and IL-15 (10 ng/ml). NK cell receptors functions were tested in re-directed cytolytic experiments against the FcγR positive P815 mastocytoma murine cell line. Briefly, effector cells were incubated with P815 cells pre-coated for 30 minutes with the mAb of interest (irrelevant mouse IgG1: 11 µg/ml, anti-NKp46: 1 µg/ml, anti-DNAM: 5 µg/ml, anti-CD277 20.1: 10 µg/ml) according to a 1:1 Effector:Target (E/T) ratio. Cytotoxic tests were performed in 4-hours assays in the presence of GolgiStop® and soluble CD107 (a&b)-FITC (both from BD Biosciences), afterward cells were stained for surface markers (CD56-PeCy7 (Beckman Coulter, Immunotech), fixed and permeabilized (Cytofix/Cytoperm®) then stained with intracellular mAb (IFN-γ (Beckman Coulter, Immunotech)). Cells were finally re-suspended in PBS 2% para-formaldehyde and extemporaneously analyzed on a BD FACS Canto® (BD Biosciences, San Jose, Calif.). The degree of activation of NK cells was measured based on the percentage of cells positive for CD107a and CD107b (degranulation) and/or the production of inflammatory cytokine (IFN-γ).

Artificial APC (aAPC)

Magnetic beads (Dynabeads M-450 Epoxy, Dynal Biotech) were coated with the following mAbs as described in Serriari et al. (serriari, ji 2010): anti-CD3 (OKT3), anti-human CD28 (CD28.2), and/or various concentrations of anti-human CD277 (CD277, 20.1) or IgG1 or anti-MHC class I (MHC I) (YJ4) or IgG1. These aAPCs were coated with suboptimal anti-CD3 Ab (5%), suboptimal levels of anti-CD28 Ab (10%), and either IgG1 Ab (CD3/CD28/IgG1), anti-CD277 Ab (CD3/CD28/CD277+IgG1) or anti-MHC class I (CD3/28/anti-MHC class I+IgG1), constituting the remaining 85% of protein added to the bead. The amount of protein was kept constant at 20 mg/ml by the addition of control IgG1.

ELISA for Cytokine Analysis

To determine the production of cytokines, cell-free supernatants were collected at 48 h and assayed for IL-2, IL-10 and IFN-γ by ELISA using OptEIA kits (BD Pharmingen) according to the manufacturer's instructions.

Immunohistochemistry

CD277 immunostainings were performed on total frozen sections of reactive lymph nodes as previously described (25). The final dilution for CD277.20.1 mAbs was 1/800. Negative control samples were prepared by omitting the primary mAb.

Screening of the Different bnt3a Isoforms Transcripts in PBMC from Healthy Subjects Public and personal Affymetrix U133+2 data sets of purified CD8, CD4, GD et NK cells were collected. CD8 and CD4 data were retrieved from the public GEO datasets (Sharp et al.) (ncbi.nlm.nih.gov/gds), while NK and gamma delta sets were personal. We used Robust Multichip Average (RMA) with the non-parametric quantile algorithm as normalization parameter. RMA was applied to the raw data collected from the various series. Quantile normalization and Loess' correction were done in R using Bioconductor and associated packages. The probe set corresponding to the three isoforms of BTN3A were retrieved from the normalized data sets and the corresponding log values were linearized for graphical representation. We used the respective Affymetrix probesets corresponding to BTN3A1, BTN3A2 and BTN3A3 isoforms: 201623_s_at, 213282_at, 204171_at Stimulation, Phosphoflow and FACS Staining Human CD4$^+$ T cells were purified by negative selection from PBMCs using magnetic beads (Miltenyi Biotec) according to the manufacturer's protocol. CD4 T cells were routinely more than 97% pure. Cells were incubated 24 hours in RPMI 1640 10% FBS at 37° C.

CD4$^+$ T cells were washed and stimulated at different times (2, 5, 10 and 30 minutes) with aAPC at a ratio of 1:3 (cells to beads) comprised of magnetic beads (Dynabeads M-450 Epoxy, Dynal Biotech) were coated with the following mAbs: anti-CD3 (OKT3), anti-human CD28 (CD28.2), and/or various concentrations of anti-human CD277 (CD277. 20.1 clone) or isotype control IgG1. These aAPCs were coated with suboptimal anti-CD3 Ab (5%), suboptimal levels of anti-CD28 Ab (10%), and either IgG1 Ab (CD3/CD28/IgG1), anti-CD277.20.1 Ab (CD3/CD28/CD277.20.1+IgG1), constituting the remaining 85% of protein added to the bead. The amount of protein was kept constant at 20 mg/ml by the addition of control IgG1. We examined the effect of mAbs CD277 clones engagement on AKT and ERK phosphorylation in CD4+ T cells by phosphoflow proteomic method [27], which uses state-specific antibodies to detect target phosphoproteins by fluorescence-activated cell sorting (FACS). We assessed the activity of the signalling pathways after exposure of the cells to beads stimulations. We apply a sandwich-labeling method, which involves the application of a biotin-conjugated secondary antibody followed by detection with fluorescently conjugated streptavidin. We demonstrated the activity of the PI3K-pathway by measuring the phosphorylation of AKT at SER 473 and ERK at p44/42 MAPK T (202/y204) after stimulation with beads with different doses of the CD277 mAb and at four different times (2, 5, 10 and 30 minutes). Cells were permeabilized, fixed and analyzed after intracellular staining of the target phosphproteins (AKT and ERK) by the use of cytofix/cytoperm KIT and perm/wash buffer (BD Biosciences).

FACS data were acquired on a FACSCanto flow cytometer (BD Biosciences) using Diva software. FACS data were analyzed using Flowjo software (TreeStar, Ashland, Oreg.).

Statistical Analysis

All data were analyzed using GraphPad Prism version 5.00 for (GraphPad, San Diego, Calif.) and microsoft excel (microsoft office). The Mann-Whitney test matched non-parametric test was used to examine: the variations of CD277 and PD-1 expression from lymphoid tissue on living T lymphocyte subsets (in FIG. 3), the variation of AKT and ERK phosphorylation on CD277 stimulated T lymphocyte cells (in FIGS. 4-5), and the difference of secretion of cytokines on T cells (in FIG. 6). The Comparisons were made between different conditions of stimulation. The Wilcoxon paired test was used to compare between different conditions of stimulation on NK cells (in FIG. 7). Differences were considered as statistically significant when p<0.05.

Results

Expression Profile of CD277 on T Cells Subpopulations and NK Cells

We had previously reported that CD277 was expressed on T and NK cells (compte et al). We decided to investigate its expression on known sub-populations of peripheral lymphocytes from healthy donors (n=4). Using multi-parametric flow cytometry, we thus analysed the CD3$^+$CD4$^+$ and the CD3$^+$CD8$^+$ subpopulations (data not shown). The staining with the monoclonal anti-CD277 (data not shown) revealed a strong expression of CD277 on both CD4$^+$ helper T cells and cytotoxic CD8$^+$ T cells (data not shown). We also looked at the expression of CD277 on memory and naïve populations of T lymphocytes based on the differential expression of CD27 and CD45RA expression (data not shown). Here again, we did not detect any significant difference between the subsets (data not shown).

In parallel, we monitored CD277 expression on another population of lymphocytes belonging to the innate immune system, the NK (data not shown). We found that 100% of NK cells also expressed high level of CD277, independently of their CD56$^{bright}$ (helper) or CD56$^{Dim}$ (cytotoxic) phenotype, showing that molecules related to the B7/CD28 family are similarly found on the two major subsets of NK cells.

Modulation of CD277 on Activated T Cells and NK Cells

As some T cells co-signaling molecules expression could be regulated after T Cell Receptor (TCR) activation, like the induction of PD1, a co-regulatory molecule, we were wondering whether CD277 could also be modulated under activation. To test this hypothesis, we compared the expression profile of CD277 and PD1 under CD3/CD28 activation of CD4$^+$ T cells.

Purified CD4$^+$ T cells from four healthy donors were thus incubated from 24 to 96 hours with monoclonal antibodies directed against CD3 and CD28 or with the respective control isotypes. As expected, the CD3/CD28 treatment results in a seven-fold increase of PD1 expression after 72 hours of culture, whereas CD277 expression was not modified at any time point (data not shown). Similar results were obtained with CD8 T cells (data not shown).

In parallel we were wondering whether CD277 expression could be modulated on NK cells. We thus stimulated NK cells with usual NK cells stimulating cytokines (IL-2 and IL-15). We compared the expression profile of CD277 and HVEM. HVEM is highly expressed on NK cells and decreased upon NK cells stimulation. Our result showed that CD277 expression was not modulated after NK cells activation, contrary to our positive control HVEM (data not shown). Altogether, these results demonstrated that T cells and NK cells constitutively express CD277, but its expression is not modulated in vitro after T or NK cells co-stimulation.

Expression Profile of CD277 on CD4 $T_FH$ Cells in Lymph Nodes

Multiple immune T cell populations are found in lymphoid organs were they play specialized functions. Among them, Follicular T helper cells ($T_FH$) are present in the germinal centers were they play an important role in B cell differentiation. These cells express the chemokine receptor CXCR5 and high levels of the cosignaling molecules ICSO but also PD-1 and BTLA. CD277 expression could be differentially regulated in lymph nodes. (FIG. 4)

Total frozen sections of reactive lymph nodes were also immuno stained for CD277. The results of immunohistochemical analysis showed a strong positivity on both interfollicular T-cells area and mantle zone B-cells indicating that they were positive on T cells as well as B cells.

Surprisingly, the pattern of staining was totally different in the germinal center. Most of the GC were negative indicating that B cells lost the expression of CD277 during the differentiation process. However, few scattered cells were staining resembling the $T_FH$ staining. We confirmed this after performing a flow cytometry analysis. The $T_FH$ cells (CXCR5+ICOS+PD-1+) were positive for CD277. In addition CD277 was equally present on the CXCR5-conventional T cells, whereas there is no significant staining in Germinal Center (GC) B-cells or cells (data not shown).

The conclusion of this first part of the study is that CD277 is expressed on all subtypes of T lymphocytes in the peripheral blood as well as in lymph nodes and NK cells, but its expression is not modulated under stimulation as it is often the case for the molecules of the B7/CD28 family, or any other molecules involved in lymphocytes regulation.

AKT and ERK Phosphorylation is Augmented after CD277 Engagement on CD4+ T Cells

To investigate the co-stimulatory role of CD277 on lymphocytes function, we searched whether CD277 triggering was able to induce the phosphorylation of the two most important kinases of the lymphocyte signaling pathway: ERK from the mitogen-activated protein kinase and the serine threonine kinase AKT. It is known that Akt and ERK signaling plays a central role in T cell functions including proliferation, protein synthesis and regulation of apoptosis.

First, we showed that the triggering of CD277 20.1 induced the phosphorylation of AKT and ERK (FIG. 2), demonstrating that CD277 stimulation is involved in the regulation of T cell activation (purified CD4+ T cells were stimulated with antibody-coated Epoxy dynabeads with mAb anti-CD3 plus mAb anti-CD277.20.1)

Second, in order to clarify the implication of CD277 as a co-modulator of the TCR signaling pathway, we stimulated purified CD4+ T cells with various concentrations of mAb to CD277.20.1 clone or isotype control IgG1, together with anti-CD3 plus anti-CD28 at different times (2, 5, 10 and 30 minutes). We observed that the cross-linking of CD277 with mAb CD277.20.1 clone strongly up regulated the phosphorylation of AKT and ERK induced by CD3+CD28 stimulation. This effect was dose and time dependent (data not shown).

In this part of the paper, we thus demonstrated that CD277 triggering potentializes the TCR signal. We next decided to investigate the functional consequences of the activation of this signaling pathway.

CD277 Costimulates CD3 Signals

We next investigated the effect of CD277 engagement on cytokine production and activation markers regulation mediated by CD3 mediated signals. Purified CD4+ T cells from at least 4 healthy donors were cultured during 24 to 72 hours with anti-CD3/anti-CD28 or anti-CD3/anti-CD277 (clone 20.1) or anti-CD3/IgG1 (control condition). After 24 hours of culture, IL-2 and IFN-γ production by CD4+ T cells were measured by ELISA. As expected, these two cytokines were produced in large amount after CD3/CD28 stimulation by comparison with the control condition (p=0.0079, p=0.0317, data not shown). Although IL-2 level produced by CD3/CD277 co-activated CD4+ T cells was lower than the one obtained with CD3/CD28 co-stimulation, the amount of IL-2 induced by CD3/CD277 co-activation was nonetheless significantly highest than the one with the IgG control (p=0.0159, data not shown). Moreover, IFN-γ secretion was strongly enhanced by CD3/CD277 co-activation compared to the control situation, and surprisingly, the production was even greater than the one obtained after CD3/CD28 co-activation (data not shown). Furthermore, after 3 days of culture, a similar effect was obtained regarding the expression profile of the activation marker CD25 after CD3/CD277 co-stimulation. This CD4+ T cells co-stimulation induced a significant increase to 45% of CD25 activated positive cells, whereas CD3/CD28 co-activation only induced an increase to 25% of activated CD25 positive cells compared with the controlled condition (data not shown).

Altogether, these results strongly suggest that CD277 is a co-stimulatory molecule of T lymphocytes activation signal.

CD277 Further Enhances CD3-CD28 Costimulation and can Act as a Third Signal to Enhance T Cell Proliferation and Cytokine Production Then, we investigated the consequences of CD277 cosignals on T cell proliferation and cytokine production induced by CD3+CD28 signals. We stimulated purified CD4+ T cells with with various concentrations of mAb to CD277, together with anti-CD3 plus anti-CD28. We kept the amount of antibody on the beads constant by adding isotype control IgG1 and anti-MHC class I (MHC I). We demonstrated that the cross-linking of CD277 on CD4+ T cells strongly activated CD4+ T cell proliferation mediated by anti-CD3 plus anti-CD28 in a dose-dependent way. Indeed, we measured the proliferation of CD4 cells by measuring the dilution of cytosolic dye CFSE (data not shown). We found that 60% of cells stimulated with anti-CD3 plus anti-CD28 and IgG1 entered division by day 5. The cross-linking of CD277 (at 17 µg/ml) strongly enhanced CD4+ T cells division already induced by anti-CD3 plus anti-CD28 in a dose dependent way, such as 90% of cells entered division (data not shown).

In parallel, our results also showed that the engagement of CD277 increased the proliferation (data not shown) and the secretion of cytokines induced by anti-CD3 and anti-CD28 stimulation in a dose-dependent way (FIG. 3).

Altogether, these data support a role of costimulatory molecule for CD277 even after optimal costimulation provided by CD28.

Is CD277 Also a Co-Stimulatory Molecule of NK Cells?

In parallel, we investigated whether a similar co-stimulatory effect was obtained in NK cells. We thus stimulated two of the most important receptors of NK cells (anti-NKp46 or anti-CD16), in presence of isotypic control or CD277 monoclonal antibody (20.1) or anti-DNAM (positive control of co-stimulation of the activation receptors) or anti-NKG2A (positive control of co-inhibition of the activation receptors). First, CD277 alone did not have any effect on NK cell stimulation. Second, the monoclonal mAb 20.1 directed against the CD277 molecules failed to potentialize any effects on NK cells activation as DNAM or NKG2A did. Both cytotoxicity (data not shown) and IFN-γ secretion (data not shown) were not affected, whether the primo-stimulation was performed with NKp46 or CD16. This result was quite surprising, but obviously CD277 is not involved in the regulation of NK cells activation, contrary to what was observed with T cells.

Btna Isoforms Expressed by Lymphocytes

Considering that CD277 has three isoforms btn3a1, btn3a2 and btn3a3, with (btn3a1 and btn3a3), or without (btn3a2) the B30.2 domain, we decided to look at the mRNA expression of each isoforms on T lymphocytes to determine whether each isoform has an equimolar expression pattern. Using available data from GEO omnibus that we further confirmed by Q-PCR, we found that btn3a1 is the main form expressed by T lymphocytes whereas the decoy form (btn3a2) is mostly expressed on NK cells (data not shown). This result was validated by quantitative PCR on 4 healthy donors. We thus emitted the hypothesis that the absence of co-stimulation in response to CD277 stimulation of NK cells might be attributed to this form of BTN3A.

EXAMPLE 3

Materials and Methods
Antibodies and Fab Fragmentation

Anti-CD277: anti-BT3-20.1 and 103.2 mAb were generated and validated as previously described [10]. Fab fragments of anti-BT3-20.1 were generated and purified with the Immunopure Fab Preparation Kit following the manufacturer's recommendation (Pierce). Protein purity was assessed by nonreducing SDS-PAGE.

Construction of Phylogenetic Trees

Phylogenetic analyses were performed using the automated genomic annotation platform FIGENIX (FIGENIX Annotation Platform: [figenix2.up.univmrs.fr/Figenix/index.jsp]) to retrieve sequences and alignments and perform phylogenetic reconstruction. The pipeline used applied three different methods of phylogenetic tree reconstruction, i.e. Maximum Parsimony [38], Maximum likelihood [39] and Neighbour Joining [40], and a midpoint rooted consensus tree was built. Bootstrapping was carried out with 1000 replications. Bootstrap values are reported for each method (for a detailed description of the pipelines and models used, see [41].

Cell Lines and Expansion of γδ T Cells P815 (mouse mastocytoma cell line), K562 (chronic myeloid leukaemia cell line), Raji and Daudi (Burkitt lymphoma cell lines) were cultured in RPMI 1640 medium (Invitrogen) and 10% foetal calf serum (FCS) (Eurobio). The PBMC from healthy donors were distributed at 106/ml in 24-well culture plates at 37° C. in 5% CO2 in RPMI 1640 medium and 10% FCS. Polyclonal Vγ9Vδ2 T cells were specifically expanded with 3 μmol/l of Phosphostim (BrHPP molecule, Innate Pharma, Marseille, France) and 100 U/ml IL-2 (Chiron, Basel, Switzerland) for 12 days. Phosphostim was added once at the onset of the culture. Every 2 days, one-half of the culture medium volume was replaced with fresh medium containing 100 U/ml IL-2.

The last day, the percentage of γδ T cells was evaluated using anti Vd2 FITC and anti-CD3-Cy7. Only cells cultures that reached more than 90% of γδ T Cells, were selected to be used in functional tests.

Flow Cytometry

We used for γδ T cells labelling in purity test after expansion, anti-CD3 PE-Cy7 and anti-Vδ2 FITC mAb (BD Pharmingen). For CD277 characterisation in different subsets PBMC were incubated with the following antibodies and molecules: anti-CD3 PE-Cy5 (BD Pharmingen), anti-CD4 PB (BD Pharmingen), anti-CD8 PB (BD Pharmingen), anti-Vδ2 FITC (BD Pharmingen), anti-CD27 APC-Alexa Fluor 750 (CALTAG Laboratory), anti-CCR7 PECy7 (BD Pharmingen), anti-CD28 PE (Beckman Coulter), anti-CD45RA ECD (Beckman Coulter), LIVE/DEAD® Fixable Dead Cell Stain Kit (L34957, Invitrogen) and anti-CD277 labelled with Alexa Fluor 647 (Protein labelling Kit Alexa Fluor 647, Molecular Probes, Invitrogen). For analysis of CD107a and CD107b expression, γδ T cells and target cells were co-incubated at 37° C. with anti-CD107a FITC and anti-CD107b FITC in presence of monensin (10 μM, GoligiStop, BD Bioscience). Cells were collected and washed with PBS, 4 hours after incubation. γδ T cells were labelled with anti-pan γδ TCR PE and anti-CD3 PECy7 mAbs (BD Pharmingen). All samples were measured on FACSCanto or FACSAria flow cytometers (BD Biosciences) using FACSDiva software. Analyses were performed with FlowJo software (Tree Star).

Supplementary Material:

Intracellular staining was performed according to the recommended by BD Pharmingen Fix and Perm Kit (BD Biosciences). 100 μl of γδ T cells at 2.106 cells/ml were plated on 96-well plates. They were incubated in presence or not of BrHPP at 3 μM and with anti-CD277 or control isotypes at 10 μg/ml, for 30 min at 4° C. Cells were stimulated at different times at 37° C. Stimulation were stopped adding 100 μl Cytofix/Cytoper solution at 37° C. for 10 min. Intracellular phosphorylated proteins were stained with purified monoclonal rabbit antibodies: anti-pZap 70, anti-pAKT and anti-pErk from Cell Signaling Technology (Danvers, USA); labelled with Biotin-SP-conjugated F(ab')2 Donkey anti-Rabbit (Jackson); and revealed with streptavidin-PE (Beckman Coulter).

Stimulation and Expansion Assay

PBMC were plated and stimulated as described in the paragraph: cell lines and expansion of γδ T cells, except cells were stimulated with anti-CD277 mAbs (10 μg/ml); or control isotypes (10 μg/ml); and with or without BrHPP at different concentrations. Cultures were stopped 9 days after. Percentages of Vγ9Vδ2 were measured the first day and the last day of culture as described above. Expanded γδ T cells effectors were stimulated with or without different doses of BrHPP added in anti-CD277 mAbs at 10 μg/ml; or with OKT3 (4 ng/ml) associated with anti-BT3 19.5 mAb in different concentrations. Activation of degranulation was measured by CD107 labelling assay as described above.

Redirected Activation Assay $2.10^5$ P815 mastocytoma mouse cells were incubated 30 min, with mouse controls isotypes or anti-CD277 mAbs (10 μg/ml) or/and with anti-CD3 (OKT3, 4 ng/ml). After washing, P815 were incubated 4 h at 37° C., with expanded Vγ9Vδ2 T effectors cells at the same concentration. A Flow-based CD107a degranulation assay was performed as described above.

ELISA

Supernatants from redirected activation essay were collected after 4 h co-culture. IFNγ, TNFα and IL-17 release was tested by ELISA Kits (OptEIA kits from BD Pharmingen for IFNγ and TNFα. Cytokines were detected with plate reader Multiskan RC (Labsystems). Cytokines concentrations were determined from standard curves established with recombinant standards.

Analysis of Vγ9Vδ2 T Cell Responses by Direct Cytotoxicity Assay:

Target cells were labelled with 20 µCi of 51Cr (PerkinElmer) for 1 h at 37° C. After washing target cells were incubated with effectors Vγ9Vδ2 T cells for 4 h at 37° C. in different ratio. Incubations were performed in presence of specific or isotype control mAbs or Fab fragments. The radioactivity released by target cells was measured, 4 h later, on beta plate counter. The percentage of specific 51Cr lysis was calculated using the following equation:

percent specific lysis=100×[(test release)−(spontaneous release)]/[(maximal release)−(spontaneous release)].

Statistical Analysis:

StatXact software (version 8 PC) produced by the Cytel, was used for all statistical analyses. Significance values for comparisons between groups were determined by the nonparametric Mann and Whitney analysis. Assuming an unequal variance with 95% confidence levels, and p values<0.05 were considered significant.

Skint-1 and CD277 Belong to the Same Super Family as B7

Using Skint-1 IgV protein domain sequence in NCBI pBlast, we searched similarity between Skint-1 and other human proteins in databases. The sequence alignments obtained show that Skint-1 is relatively similar to CD277 with 38% of identity (data not shown). To clarify the relationships between this Skint and Btn families, we performed phylogenetic analysis based on their IgV sequences, using the Figenix automated genomic annotation platform.

The phylogeny shows that Skint-1 and CD277 form a monophylogenetic group with genes or genes family implied in immune response regulation: BTN 1 to 3, BTNL2 ERMAP; B-G and MOG (data not shown). This group also includes CD80 and CD86 from to B7 family, equally known for its involvement in immune response regulation. Every group forms a subfamily.

When we focused on the Skint subfamily (data not shown), phylogenetic analysis based on Skint-1 full sequence evidences at least eight paralog genes in rodents including five in mice in sharp contrast with primates where there is only one copy. This result suggests an important role of the skint family in rodents. We performed the same analysis using CD277 sequence (data not shown). We show that CD277 and his second isoform: BTN3-A3, have a common ancestor in embranchment between horse and primates. Interestingly, these two isoforms are present in primates but are absent in rodents.

Human Skint-1 gene is a likely pseudogene since two stop codons are present within its sequence. The first stop codon is located immediately downstream to the signal peptide, at the beginning of the IgV sequence and the second downstream of the first transmembrane domain [7]. It is unlikely to be due to sequencing errors because we find the very same mutations in Pongo abelii DNA sequence. These data indicated that Skint genes were not necessary for primate species and suggested that their function could be performed by other genes.

In a reciprocal way, CD277 gene was absent in *Ratus norvegicus* and in *Mus musculus* DNA sequence using NCBI ntBlast. Indeed, within the BTN families only BTN2 sequence was present in these two species. These results indicated that CD277 really disappeared in rodents and consequently were not necessary for survival of these species. This suggests that CD277 function has been assumed by other gene(s).

Both functional redundancies in rodents and primates common ancestors could be on one hand at the origin of disappearance of CD277 in rodents and on the other hand of Skint-1 in primates.

To summarize, both molecules have similarities in their extracellular region within both IgV and IgC domains, but differ by the number of transmembrane domains and above all by their intracytoplasmic region (data not shown). Indeed, CD277 has only one transmembrane domain instead of three for Skint-1. Furthermore, in their intracytoplasmic region, CD277 has a 830.2 domain. This domain is absent in Skint-1.

CD277 is Expressed in Vγ9Vδ2 T Cells and not Modulated by their Differentiation

We had previously shown that CD277 was expressed on conventional T lymphocytes suggesting a role of CD277 in the regulation of T cell response.

We tested CD277 expression on γδ T cells as well as their described subpopulations corresponding to their different stages of differentiation starting from the naïve compartment. Hence using 8 colour flow cytometry, we determined 4 major subpopulations: Naives cells (CD45RA+/CD27+); Central Memory cells (CD45RA−/CD27+); Effectors Memory (CD45RA−/CD27−/CCR7−) and Effectors Memory RA+(CD45RA+/CD27−/CCR7−). We also evaluated CD28 that discriminated two subsets among N, CM, EM as well as EMRA+ gd T cells. Its function is not clear although in αβ T cells it is associated to CTL functions. 95% of Vγ9Vδ2 T cells express CD277 with higher mean fluorescence intensity than αβ T cells suggesting an important role in homeostasis of γδ T cells. Interestingly in all of Vγ9Vδ2 subpopulation, every cells express CD277. Its level of expression is approximately the same in the analysed γδ T cell subpopulations. The only slight increase was found in the naive CD45RA+/CD27+/CD28+/CCR7+, but this variation was not significant in the series if healthy volunteers tested.

Theses results indicate that CD277 is not modulated in Vγ9Vδ2 T cells differentiation and suggest a putative role at the different stages of Vγ9Vδ2 T cells activation.

Anti-CD277 mAb 20.1 Induces Proliferation of Vγ9Vδ2 T Cells Whereas 103.2 Inhibits the Stimulation Mediated by Optimal TCR Stimulation by Phosphoantigens.

To investigate the function of CD277 in γδ T cells we used mAbs directed against CD277. In a first setting we tested whether CD277 triggering might affect the stimulation of γδ T cells by optimal doses of the phosphoantigen BrHPP. We cultured PBMC with IL-2 (100 U/ml) and BrHPP (3000 nM).

After 15 days of culture Vγ9Vδ2 T cells were expanded (FIG. 5A) upon anti-CD277 mAb 20.1 addition. This effect was associated with the proliferation of the Vγ9Vδ2 cells as demonstrated by the analysis of CFSE labeled cells (FIG. 5B).

This result suggests a stimulatory function of CD277 20.1 on Vγ9Vδ2 T cells activation.

We then tested the function of CD277 mAb 103.2 on the phosphoantigen mediated activation of Vγ9Vδ2 cells. 103. mAb inhibited completely the Vγ9Vδ2 T cell activation mediated by phosphoantigens but CD3mAbs (FIGS. 6A and 6B). Similar effects were demonstrated in Jurkat cells expressing Vγ9Vδ2TcR CD277 Modulate the Degranulation in Vγ9Vδ2 T Cells Mediated by the TcR Complex These data prompted us to test whether the function of CD277 could be detected in another functions of γδ T cells such as cytokine production, cytotoxicity and degranulation.

We stimulated γδ T cells by phosphoantigens and tested the expanded cells for their effector functions. We first used the modulation of CD107 expression as an indicator of degranulation. This test corresponds in part to the ability of cells to elicit their cytolytic function. In this experiment, we measured the effect of the CD277 engagement with either suboptimal (0.06 nM) or optimal (4000 nM) doses of the phosphoantigen BrHPP.

Increasing doses of BrHPP induces increasing CD107 expression up to 40%. Using a low dose of BrHPP unable to induce CD107 expression, addition of anti-CD277 increased CD107 expression up to (20%). However, with high dose of BrHPP, anti-CD277 inhibited CD107 expression induced by BrHPP which decreased from 40% to 20%. We tested another system of γδ T cell stimulation using anti-CD3 and anti-CD277 immobilised mAbs. CD277 stimulation alone induced CD107 expression (30%). CD3 mAb induced a dose dependent CD107 expression that reached plateau at 50 ng/ml in this setting.

We next tested CD107 expression using a steady dose of CD277 mAb with increasing concentration of CD3 mAb. CD107 expression was increased when combining CD277 with increasing doses of anti-CD3 up to 10 ng/ml. However, at higher doses of CD3 mAb CD107 expression decreased in a dose dependent manner.

Altogether these data demonstrate that CD277 modulates the ability of γδ T cells to express CD107 and hence to degranulate following phosphoantigen or anti-CD3 stimulation. CD277 effect is biphasic: enhancing at low stimulation levels and decreasing at higher levels of TCR crosslinking the γδ T cell degranulation activity.

Crosslinking of CD277 Triggers Degranulation Together with INFγ and TNFα Release.

We next performed redirected stimulation of expanded Vγ9Vδ2 T cells using CD277 mAb. The anti-CD277 alone induces CD107 expression after 4 hours of stimulation in a dose dependent manner (10%<30%). The optimal activation is obtained with 10 μg/ml dose of anti-CD277 whereas the ID50 of the mAb for its target is 3 ug/ml (data not shown).

Moreover, CD227 engagement induced the robust release of IFNγ and TNFα that was detected early as soon as 4 hours stimulation. So the degranulation induced by CD277 comes along with Th1 cytokines. This degranulation and cytokines release induction results of CD277 stimulation by anti-CD277 crosslinking without the need for TCR engagement.

CD277 Potentiate the Anti-Tumor Cytolysis Mediated by Vγ9Vδ2 T Cells.

Finally, we tested whether CD277 could be involved in the anti-tumor function of Vγ9Vδ2 T cells activation. To verify this hypothesis, we used anti-CD277 mAb and anti-CD277 Fab fragments in cytotoxicity assay against various tumor cell lines including Daudi, K562 or Raji cells lines. 20.1 Mab potentiated or revealed the function Vγ9Vδ2 T cells against the targets as determined by the CD107a/b degranulation assay (FIG. 7). In contrast 103.2 mAb prevented the activation of Vγ9Vδ2 T cells in the same experimental setting (data not shown).

These results show that CD277 mAbs potentiate or inhibit the anti-tumor cytolysis mediated by responding Vγ9Vδ2 T cells.

EXAMPLE 4: THE ACTIVATING ANTIBODIES OF THE INVENTION CAN BE USED TO TREAT CANCER, PARTICULARLY ACUTE MYELOID LEUKEMIA

Material and Methods
Patients

Written informed consent was obtained from the twenty-five AML patients included in this study, in accordance with the Declaration of Helsinki. Clinical data are detailed in the following Table.

| Patients | Sex | Age (years) | Clinical condition | WHO Classification | FAB Classification | % of circulating blasts |
|---|---|---|---|---|---|---|
| UPN01 | H | 40 | Diagnosis | 1a | 4 | 80 |
| UPN02 | H | 47 | Diagnosis | 4 | 1 | 93 |
| UPN03 | F | 62 | Relapse | 4 | 2 | 98 |
| UPN04 | F | 59 | Diagnosis | 4 | 5a | 94 |
| UPN05 | H | 57 | Progression | 1a | 4 | 95 |
| UPN06 | H | 81 | Diagnosis | 4 | 0 | 98 |
| UPN07 | F | 66 | Diagnosis | 4 | 5a | 92 |
| UPN08 | H | 71 | Diagnosis | 4 | 4 | 97 |
| UPN09 | H | 54 | Diagnosis | 1a | 5a | 89 |

The study was approved by the local institutional review boards of the Institut Paoli Calmettes. Peripheral Blood Mononuclear Cells (PBMCs) from twenty HV were provided by the local Blood Bank (EFS). PBMCs from AML patients and HV were isolated by density gradient centrifugation (Lymphoprep, Abcys) and viably frozen until use. Samples with more than 80% of blasts were selected for the study.

Reagents and Antibodies

BrHpp was from Innate Pharma (Marseilles, France). Zoledronate (ZOL) was from Novartis (United Kingdom). Recombinant human (Rh) IL2 and rhIL-15 were from BD Biosciences (San Jose, Calif., USA). The mAbs used for functional experiments and cytometry are listed in the following Table:

| m Ab/reactive | Isotype | Use |
|---|---|---|
| Control isotype Functional grade | Ig G1 | eBioscience | in vitro and in vivo |
| Anti-BTN3A clone 20.1 | Ig | Home Made | Functional tests |
| Anti-BTN3A clone 108.5 | Ig | Beckman Coulter | In vitro |
| Anti-TCRVγ9 (IMMU510) | Ig | | Functional tests |
| Human CD45-Fitc | Ig | | Flow cytometry |
| Human CD45-APC | Ig | | |
| CD112-PE | Ig | | |
| CD155-PE | Ig | | |
| CD54-Fitc | Ig | | |
| TCR Pan γδ-PE | Ig | | |
| TCR Vδ2-Fitc | Ig | | |
| CD33-PE | Ig | BD Biosciences | |
| CD107a/b-Fitc | Ig | | |
| IFNg-APC | IgG | | |
| MICA/B-PE | IgG | | |
| 7-AAD PE-Cy5 | — | | |
| CD3-AF700 | IgG1 | eBioscience | |
| Murine CD45-APC eFluor78 | | | |
| Human CD45-V450 | Ig | BioLegend | |
| TNFa-eFluorV450 | Ig | | |
| CD56-PE-Vio770 | Ig | Miltenyi Biotech | |
| ULBP1-PE | IgG | R & D | |
| ULBP2-APC | IgG | | |
| ULBP3-PE | IgG2a | | |
| Live dead-Amcyan | — | Life technologies | |
| Live dead-Far Red | — | | |

| m Ab/reactive | Isotype | Use |
|---|---|---|
| Count Bright Absolute Counting Beads | — | Quantification of blastic cells |

Generation of Anti-Human BTN3A mAbs

Anti-BTN3A mAbs (clone 20.1 and 108.5) were generated as previously described[19] and labeled for cytometry using Alexa Fluor® 647 Protein Labeling Kit (Life Technologies).

Cell Culture

Effector γδ T cells were established and maintained as previously described[28]. PBMC from HV were stimulated with ZOL (1 µM) and rhiL-2 (2001 U/ml) at Day 0. From Day 5, rhiL-2 was renewed every two days and cells were kept at $1.5 \times 10^6$/ml for 15 days. NK cells were isolated using EasySep Human NK cell enrichment kit (StemCell Technologies). The purity of γδ T cells and NK cells was determined by flow cytometry and respectively greater than 80% and 98%. The Burkitt lymphoma cell line, DAUDI, the human AML cell line, 0937, and the erythroleukemic cell line, K562, were obtained from the American Type Culture Collection and cultured ($0.5 \times 10^6$/ml) in RPMI 1640 medium with 10% FCS. BTN3A Knock-down HEK293FT cells (sh #284; clone #30) were provided by E. Scotet (Inserm U892, Nantes), cultured and transfected with BTN3A1, BTN3A2, BTN3A3 mutated cDNA-containing plasmids, as described[23].

Flow Cytometry $2 \times 10^5$ PBMC were washed in PBS (Cambrex Bio Science) and incubated at 4° C. for 20 min with specified mAb. Following incubation and washing, samples were analyzed on LSRFortessa or FACS Canto II (Becton Dickinson) using DIVA software (BD bioscience, Mountain View, Calif.). For analysis of CD107 expression, γδ T cells were incubated at 37° C. in the presence of anti-CD107a and Golgi stop with or without anti-BTN3A 20.1 mAb. After 4 hours, cells were collected, washed in PBS and analyzed by flow cytometry. To study cytokine production, cells were further permeabilized with Permwash (BD bioscience) to allow intracellular staining with labeled antibodies. Trogocytosis of PKH67 (Sigma Aldrich) labeled blasts by γδ T cells was quantified as previously described[29].

Chromium Release Assay $0.5 \times 10^6$ target cells were incubated with 50 µCi of $^{51}$Cr (Perkin-Elmer) for AML blasts and 10 µCi for DAUDI and K562 cells for 90 minutes and mixed with effector cells in a Effector:Target (E:T) ratio of 30:1±15:1±10:1±1:1. After 4 hours of incubation at 37° C., 50 µl supernatant of each sample was transferred in LUMA plates and radioactivity was determined by a gamma counter. The percentage of specific lysis was calculated using the formula [(experimental−spontaneous release/total−spontaneous release)×100] and expressed as the mean of triplicate.

Determination of BTN3A Isoforms Expression by Quantitative RT-PCR (qRT-PCR)

Total RNA from AML blasts was performed with TRIzol (Life Technologies). The RNA was reverse-transcribed using oligo(dT) and M-MLV Reverse Transcriptase Protocol (Life Technologies). qRT-PCR was performed and analyzed with the Applied Bio-systems 7900HT Fast Real-Time PCR system. The Ct (threshold cycle) was calculated for each assay (Sequence Detection System Software 2.3, Applied Biosystems). Data were normalized using GAPDH as endogenous control ($\Delta Ct = Ct_{target\ gene} - Ct_{GAPDH}$). Higher ΔCt means lower expressions of analyzed genes. Probes were BTN3A1 (Hs01063368_m1), BTN3A2 (Hs00389328_m1), BTN3A3 (Hs00757230_m1) and GAPDH (Hs99999905_m1) Taqman gene expression Assays (Applied Biosystems).

Western Blot 5 to $20 \times 10^6$ AML blasts were washed in cold PBS, and lysed in 110 µl of ice-cold TIT buffer (50 mM Tris pH 7.4, 200 µM NaF, 2.5 mM EDTA pH 7.4, 150 mM NaCl, 1% Triton X-100, 1% Nonidet-P40 and 5% glycerol) containing protease inhibitors (Roche Applied Science) and 1 mM Na3VO4. Proteins in all cell lysates were quantified according to the manufacturer's instructions (Pierce™ BCA Protein Assay Kit). Proteins were resolved by SDS-PAGE 10%, followed by western blotting with primary antibodies anti-BTN3A 20.1 and anti-GrB2 (SantaCruz technology). They were detected with peroxidase-conjugated anti-mouse IgG1 and anti-rabbit IgG antibodies (Jackson Laboratory). Immunoreactive bands were detected using enhanced chemoluminescent reagents (Pierce).

NSG Mouse/Human AML Model

NOD-SCID common γ-chain knockout mice (NSG) were purchased from Charles River France or bred in-house and maintained under specific pathogen-free conditions. All animal procedures were in accordance with protocols approved by the local Committee for Animal Experiments. Healthy 6- to 8-weeks-old female mice (n=15) received an injection of $0.2 \times 10^6$ luciferase transduced-U937 cells on Day 0, as described[13], and were then randomly assigned in 5 groups to receive intravenous injections of post-expansion-purified Vγ9Vδ2 T cells on Day 1 ($30 \times 10^6$, 98.8% CD3+TCRVδ2+; Unité de Thérapie Cellulaire et Génique de Nantes) alone or combined to anti-BTN3A 20.1 mAb (250 µg) on Day 2 and 6. Controls comprised NSG mice infused with PBS, or anti-BTN3A 20.1 mAb alone. Mice were imaged with a Photon Imager (Biospace Lab, Paris, France) at different days. For the Primary AML blasts model, NSG mice received sublethal irradiation (2 Gy). On the day after, they received $1 \times 10^6$ of CD3-depleted blasts (CD3 depletion Kit, Miltenyi Biotec) isolated from UPN09. Treatments comprising intravenous infusions of expanded Vγ9Vδ2 T cells ($15 \times 10^6$, 90% CD3+TCRVδ2+) and either anti-BTN3A 20.1 mAb (250n) or IgG1 (250 µg), were administered twice a week, from 8 to 10 weeks post-graft. The peripheral blood number of blasts was quantified during engraftment, before and after treatment by Flow Cytometry (supplementary data 1B). Mice were sacrificed at week 11th post-graft and the number of blasts was quantified in their Bone Marrow (BM).

Statistics

Results are expressed as median±SEM. Statistical analysis was performed using Spearman correlation, Wilcoxon test and Mann-Whitney t test. P values<0.05 were considered significant. Analyses were performed using GraphPad Prism program.

Results

Primary AML Blasts are Killed by Both Allogeneic NK Cells and Expanded Vγ9Vδ2 T Cells but have Differential Sensitivity to these Effectors Here, expanded Vγ9Vδ2 T cells and sorted NK cells obtained from HV were compared for their cytotoxic activity against primary AML blasts. For these studies, cytotoxicity measured by $^{51}$Cr release assay was normalized to cytotoxicity measured against the respective preferential targets, K562 and DAUDI cell lines. We found no statistical difference (p=0.2008) between the overall level of cytotoxicity exhibited by Vγ9Vδ2 T cells (26.9±4.9%) and NK cells (36.1±4.7%) (FIG. 8A). No correlation was found between the specific cytotoxicity of sorted NK cells and expanded Vγ9Vδ2 T cells against AML blasts (FIG. 8B).

The Expression of Vγ9Vδ2 T Cells Activating Molecules on Primary AML Blasts Correlates with their Sensitivity to Vγ9Vδ2 T Cells-Mediated Killing The lack of correlation between NK cells and Vγ9Vδ2 T cells specific lysis of AML blasts prompted us to investigate molecules known to activate both effectors, namely DNAM1 ligands, Nectin-2 and PVR, NKG2D ligands, MICA/B and ULBP1/2/3 and LFA1 ligand, ICAM1. Nectin-2 ($r_s$=0.4; p=0.0449), ULBP2 ($r_s$=0.45; p=0.0192) and ICAM1 expression ($r_s$=0.57; p=0.0046) on primary AML blasts positively correlated with their sensitivity to Vγ9Vδ2 T cells-mediated lysis. (FIGS. 9A, 9B and 9C). No significant correlations were found for PVR, ULBP1/3, MICA/B expressions on blasts and Vγ9Vδ2 T cells lysis (data not shown). In parallel, we investigated BTN3A. All the primary AML blasts expressed BTN3A. BTN3A surface expression, assessed with the anti-BTN3A 20.1 mAb did not correlate with Vγ9Vδ2 T cells cytotoxicity ($r_s$=0.1695; p=0.4394).

TCR Agonists Specifically Enhance Vγ9Vδ2 T Cells Lysis of Primary AML Blasts Through BTN3A Triggering BTN3A1 is a key player in Vγ9Vδ2 TCR activation[23]. The lysis of AML blasts is mainly TCR-mediated. However, we still do not know whether BTN3A is acting in primary tumors. Hence, we decided to assess whether anti-BTN3A 20.1 mAb acted on primary AML blasts. We first compared the effect of TCR agonists to anti-BTN3A agonist 20.1 mAb. We observed that ZOL and anti-BTN3A 20.1 mAb were significantly more efficient (p=0.0098 and p<0.0001 respectively) than BrHpp to enhance Vγ9Vδ2 T cells lysis of AML blasts (FIG. 10A).

To dissect the role of BTN3A in Vγ9Vδ2 T cells lysis of AML blasts, we performed cytotoxicity assays, combining TCR Vγ9 blocking mAb, ZOL and anti-BTN3A mAbs with agonist (20.1 mAb) or antagonist (108.5 mAb) functions. The TCR blockade resulted in significant decreases of ZOL-(p=0.0156) and anti-BTN3A 20.1-induced lysis of AML blasts (p=0.0156) (FIG. 10B). The addition of anti-BTN3A 20.1 mAb to ZOL resulted in a poor but significant (p=0.0420) enhancement of AML blasts lysis by Vγ9Vδ2 T cells. Conversely, antagonist anti-BTN3A 108.5 mAb could significantly and drastically abrogate ZOL-induced lysis (p=0.0156) (FIG. 3B). Finally, in order to confirm that anti-BTN3A 20.1 mAb and ZOL effects were specifically confined to Vγ9Vδ2 TCR, we assessed their effects on NK cells-mediated AML blasts lysis. Unlike Vγ9Vδ2 T cells, anti-BTN3A 20.1 mAb and ZOL had no effect upon NK cells-mediated AML blasts lysis. Collectively, these data confirmed that BTN3A specifically allows the sensitization of NBP-treated primary AML blasts to Vγ9Vδ2 TCR-mediated lysis and can be triggered with agonist mAb.

Triggering BTN3A on the Surface of AML Blasts with Agonist 20.1 mAb can Overcome their Poor Sensitization by N-BP Treatment Anti-BTN3A agonist mAb has been shown to sensitize tumor cell lines to killing by Vγ9Vδ2 T cells[23]. We next asked whether agonist anti-BTN3A 20.1 mAb could similarly sensitize primary tumors such as AML blasts to killing by Vγ9Vδ2 T cells. In addition, we examined whether sensitization to killing occurred through the interaction of anti-BTN3A 20.1 mAb with AML blasts themselves, or rather as a consequence of anti-BTN3A 20.1 mAb exerting its effects upon Vγ9Vδ2 T cells. In a cytotoxicity assay, we compared the lysis of AML blasts either i) after blasts pre-incubation with anti-BTN3A 20.1 mAb (washed before co-incubation with Vγ9Vδ2 T cells), or ii) after simultaneous incubation of blasts, anti-BTN3A 20.1 mAb and Vγ9Vδ2 T cells, or iii) after Vγ9Vδ2 T cells were previously incubated with anti-BTN3A 20.1 mAb (then washed before co-incubation with AML blasts). The lysis achieved with Vγ9Vδ2 T cells pre-incubated with anti-BTN3A 20.1 mAb was comparable to basal lysis (4.36±2.11%). The lysis was enhanced when blasts were pre-incubated with anti-BTN3A 20.1 mAb (22.92±7.64%) and further enhanced by simultaneous incubation of effector cells, target cells and mAb (35.95±1.16%) (FIG. 11A). Those results show that anti-BTN3 20.1 mAb acts upon AML blasts rather than upon Vγ9Vδ2 T cells and that the anti-BTN3A 20.1 mAb agonist effect was most pronounced when effectors, targets and mAb were simultaneously present.

Treatment with BrHpp has been shown to enhance the contact-dependent capture of AML cell membrane via trogocytosis[13] leading us to hypothesize that the anti-BTN3A 20.1 agonist mAb might induce a similar effect. As shown in FIGS. 11B and 11C, treatment with anti-BTN3A 20.1 mAb significantly enhanced the trogocytosis of AML blasts by Vγ9Vδ2 T cells (p=0.0039). Finally, we observed that when Vγ9Vδ2 T cells were co-cultured with AML blasts in the presence of anti-BTN3A 20.1 agonist mAb, they showed greater cytokine production of TNFα (p=0.0313) and IFNγ (p=0.0313) and also showed a greater ability to degranulate as assessed by the expression of CD107a (p=0.0313) (FIG. 11D). Collectively, these data demonstrated a potent role of anti-BTN3A 20.1 mAb to restore lysis of resistant AML.

Finally, AML blasts are not equally sensitized to Vγ9Vδ2 T cells lysis by N—BP[18]. We thus determined the extent to which AML blasts that were either resistant or poorly responsive to N-BP sensitization could be sensitized by anti-BTN3A 20.1 mAb. As shown in FIG. 4E, Vγ9Vδ2 T cell lysis of ZOL-resistant or ZOL-poorly responsive AML blasts was significantly enhanced by the treatment with anti-BTN3A mAb (p=0.0005).

Altogether, these data converge to show that BTN3A triggering on AML blasts with the agonist 20.1 mAb can significantly enhance their recognition and subsequent lysis by Vγ9Vδ2 T cells, thus overcoming their resistance to N-BP treatment.

Primary AML Blasts Mainly Express BTN3A2 Irrespective of their Sensitivity to N-BP-Induced-Vγ9Vδ2 T Cells Lysis We assessed the level of expression of each BTN3A isoform at the transcriptional level by qRT-PCR and protein level by Western Blot (based on their differences in size). Compared to BTN3A1 (Mean ΔCT=11.43±0.35) and BTN3A3 (Mean ΔCT=11.99±0.29), BTN3A2 was the most abundant isoform both at transcriptional (Mean ΔCT=7.767±0.43; p<0.0001) (FIG. 12A) and protein levels in all primary AML blasts (FIGS. 12B and 12C). BTN3A1 and BTN3A3 were expressed at the transcriptional level but barely detected at the protein level. We found no differences regarding the expression of the three isoforms between N-BP-poorly sensitive (FIG. 12B) and N-BP-sensitive AML blasts (FIG. 12C).

Altogether, these data show that despite its weak expression, BTN3A1 can be triggered by N-BP. It nonetheless remains possible that BTN3A2, expressed at the highest level, might be triggered by the agonist 20.1 mAb, this leading to enhanced Vγ9Vδ2 T cell-mediated lysis through as-yet unknown mechanisms.

Anti-BTN3A mAb Combined with γδ T Cells Infusion Decreases Leukemic Burden in AML Xenografted Mice Models We next asked whether the in vitro potentiating effects of anti-BTN3A 20.1 mAb against leukemia cells could be reproduced in vivo, in a xenotransplantation model using primary AML blasts[30]. Blasts from UPN09 were poorly sensitive to Vγ9Vδ2 T cells lysis but highly sensitized after treatment with anti-BTN3A 20.1 mAb in vitro (data not shown). Blasts from UPN09 highly engrafted in BM and blood of NSG mice, thus recapitulating human disease. We asked whether anti-BTN3A 20.1 mAb and Vγ9Vδ2 T cells-immunotherapy could decrease the disease progression in this model. We showed a significant decrease of circulating blasts in the anti-BTN3A 20.1 mAb treated group (37.38±39.89) compared to IgG1 (388.1±212.3; p=0.0379) and untreated group (1208±817; p=0.0022) (FIG. 13). These data highlight the potent anti-leukemic effect exerted by anti-BTN3A 20.1 mAb combined to Vγ9Vδ2 T cells immunotherapy in vivo.

REFERENCES

Throughout this application, various references describe the state of the art to which this invention pertains. The disclosures of these references are hereby incorporated by reference into the present disclosure.

Arnett, H. A., Escobar, S. S., Gonzalez-Suarez, E., Budelsky, A. L., Steffen, L. A., Boiani, N., Zhang, M., Siu, G., Brewer, A. W., and Viney, J. L. 2007. BTNL2, a butyrophilin/B7-like molecule, is a negative costimulatory molecule modulated in intestinal inflammation. J. Immunol. 178: 1523-1533.

Bensussan, A., Olive, D. 2005. T-cell: section report. Cellular Immunol. 236: 3-5.

Carreno, B. M., and Collins, M. 2002. The B7 family of ligands and its receptors: new pathways for costimulation and inhibition of immune responses. Annu. Rev. Immunol. 20:29-53.

Chambers, C. A., Kuhns, M. S., Egen, J. G., and Allison, J. P. 2001. CTLA-4-mediated inhibition in regulation of T cells responses: mechanisms and manipulation in tumor immunotherapy. Annu. Rev. Immunol. 19:565-594.

Chapoval, A. I., Ni, J., Lau, J. S., Wilcox, R. A., Flies, D. B., Liu, D., Dong, H., Sica, G. L., Zhu, G., Tamada, K., and Chen, L. 2001. B7-H3: a costimulatory molecule for T cell activation and IFN-gamma production. Nat. Immunol. 2:269-274.

Compte, E., Pontarotti, P., Collette, Y., Lopez, M., and Olive, D. 2004. Characterization of BT3 molecules belong to the B7 family expressed on immune cells. Eur. J. Immunol. 34:2089-2099.

Coyle, A. J., and Gutierrez-Ramos, J. C. 2001. The expanding B7 superfamily: increasing complexity in costimulatory signals regulating T cell function. Nat. Immunol. 2:203-209.

Dong, H., Zhu, G., Tamada, K., and Chen, L. 1999. B7-H1, a third member of B7 family, costimulates T cell proliferation and interleukin-10 secretion. Nat. Med. 5:1365-1369.

Durum, S. K., Schmidt, J. A., and Oppenheim, J. J. 1985. Inteleukin 1: an immunological Perspective. Annu. Rev. Immunol. 3:263-287.

Eisenberg, S. P., Evans, R. J., Arend, W. P., Verderber, E., Brewer, M. T., Hannun, C. H., Thompson, R. C. 1990. Primary structure and functional expression from complementary DNA of a human interleukin-1 receptor antagonist. Nature. 343:341-346.

Freeman, G. J., Long, A. J., Iwai, Y., Bourque, K., Chernova, T., Nishimura, H., Fitz, L. J., Malenkovich, N., Okazaki, T., Byrne M. C., Horton, H. F., Fouser, L., Carter, L., Ling, V., Bowman, M. R., Carreno, B. M., Collins, M., Wood, C. R., and Honjo, T. 2000. Engagement of the PD-1 immunoinhibitory receptor by a novel B7 family member leads to negative regulation of lymphocyte activation. J. Exp. Med. 192:1027-1034.

Fulton, S. A., Johnsen, J. M., Wolf, S. F., Sieburth, D. S., and Boom, W. H. 1996. Interleukin-12 production by human monocytes infected with *Mycobacterium tuberculosis*: role of phagocytosis. Infect. Immun. 64:2523-2531.

Grob, P. M., David, E., Warren, T. C., De Leon, R. P., Farina, P. R., and Homon, C. A. 1990. Characterization of a receptor for human monocyte-derived neutrophil chemotactic factor/interleukin-8. J. Biol. Chem. 265:8311-8316.

Henry, J., Mather, I. H., McDermott, M. F., and Pontarotti, P. 1998. B30.2-like domain proteins: update and new insights into a rapidly expanding family of proteins. Mol. Biol. Evol. 15:1696-1705.

Henry, J., Miller, M., and Pontarotti, P. 1999. Structure and evolution of the extended B7 family. Immunol. Today. 20:285-288.

Hutloff, A., Dittrich, A. M., Beier, K. C., Eljaschewitsch, B., Kraft, R., Anagnostopoulos, I., and Kroczek, R. A. 1999. ICOS is an inducible T cell co-stimulator structurally and functionally related to CD28. Nature. 397: 263-266.

June, C. H., Bluestone, J. A., Nadler, L. M., and Thompson, C. B. 1994. The B7 and CD28 receptor families. Immunol. Today. 15:321-331.

Kaufman, J., and Salomonsen, J. 1992. B-G: we know what it is, but what does it do? Immunol. Today. 13: 1-3.

Latchman, Y., Wood, C. R., Chernova, T., Chaudhary, D., Borde, M., Chernova, I., lwai, Y., Long, A. J., Brown, J. A., Nunes R., Greenfield, E. A., Bourque, K., Boussiotis, V. A., Carter, L. L., Carreno, B. M., Malenkovich, N., Nishimura, H., Okazaki, T., Honjo, T., Sharpe, A. H., and Freeman, G. J. 2001. PD-L2 is a second ligand for PD-1 and inhibits T cell activation. Nat. Immunol. 2:261-274.

Ledbetter, J. A., Imboden, J. B., Schieven, G. L., Grosmaire, L. S., Rabinovitch, P. S., Lindsten, T., Thompson, C. B., and June, C. H. 1990. CD28 ligation in T-cell activation: evidence for two signal transduction pathways. Blood. 75:1531-1539.

Lenschow, D. J., Walunas, T. L., and Bluestone, J. A. 1996. CD28/B7 of T cell co-stimulation. Annu. Rev. Immnuol. 14:233-258.

Linsley, P. S., Greene, J. L., Tane, P., Bradshaw, J., Ledbetter, J. A., Anasetti, C., and Damle, N. K. 1992. Coexpression and functional cooperation of CTLA-4 and CD28 on activated T lymphocytes. J. Exp. Med. 176:1595-15604.

Linsley, P. S., and Ledbetter, J. A. 1993. The role of the CD 28 receptor during T cell responses to antigen. Annu. Rev. Immunol. 11:191-212.

Liu, Y., and Linsley, P. S. 1992. Costimulation of T-cell growth. Curr. Opin. Immunol. 4:265-270.

Ma, X., Chow, J. M., Gri, G., Carra, G., Gerosa, F., Wolf, S. F., Dzialo, R., and Trinchieri, G. 1996. The interleukin-12 p40 gene promoter is primed by interferon gamma in monocytic cells. J. Exp. Med. 183:147-157.

Medzhitov, R. 2001. Toll-like receptors and innate immunity. Nat. Rev. Immunol. 1:135-145.

Nurieva, R., Thomas, S., Nguyen, T., Martin-Orozco, N., Wang, Y., Kaja, M. K., Yu, X. Z., and Dong, C. 2006. T-cell tolerance or function is determined by combinatorial costimulatory signals. Embo J. 25:2623-2633.

Price, P., Santoso, F., Mastaglia, M., Garlepp, C., Kok, C., Allcock, R., and Laing, N. 2004. Two major histocompatibility complex haplotypes influence susceptibility to sporadic inclusion body myositis: critical evaluation of an association with HLA-DR3. Tissue Antigens. 64: 575-580.

Rhodes, D. A., Stammers, M., Malcherek, G., Beck, S., and Trowsdale, J. 2001. The cluster of BTN genes in the extended major histocompatibility complex. Genomics. 71: 351-362.

Ruddy, D. A., Kronmal, G. S., Lee, V. K., Mintier, G. A., Quintana, L., Domingo, R. Jr., Meyer, N. C., Irrinki, A., McClelland, E. E., Fullan, A., Mapa, F. A., Moore, T., Thomas, W., Loeb, D. B., Harmon, C., Tsuchihashi, Z., Wolff, R. K., Schatzman, R. C., Feder, J. N. 1997. A 1.1-Mb transcript map of the hereditary hemochromatosis locus. Genome Res. 7: 441-456.

Rybicki, B. A., Walewski, J. L., Maliarik, M. J., Kian, H., and Iannuzzi, M. C. 2005. The BTNL2 gene and sarcoidosis susceptibility in African Americans and Whites. Am. J. Hum. Genet. 77: 491-499.

Salmaso, C., Olive, D., Pesce, G., and Bagnasco, M. 2002. Costimulatory molecules and autoimmune thyroid diseases. Autoimmunity. 35:159-167.

Saverino, D., Tenca, C., Zarcone, D., Merlo, A., Megiovanni, A. M., Valle, M. T., Manca, F., Grossi, C. E., and Ciccone, E. 1998. CTLA-4 (CD152) inhibits the specific lysis mediated by human cytolytic T lymphocytes in a clonally distributed fashion. J. Immunol. 162:651-658.

Sun, M., Richards, S., Prasad, D. V., Mai, X. M., Rudensky, A., and Dong, C. 2002. Characterization of mouse and human B7-H3 genes. J. Immunol. 168:6294-6297.

Takeda, K., and Akira, S. 2003. Toll receptors and pathogen resistance. Cell Microbiol. 5:143-153.

Tseng, S. Y., Otsuji, M., Gorski, K., Huang, X., Slansky, J. E., Pai, S. I., Shalabi, A., Shin, T., Pardoll, D. M., and Tsuchiya, H. 2001. B7-DC, a new dendritic cell molecule with potent costimulatory properties for T cells. J. Exp. Med. 193:839-846.

Valentonyte, R., Hampe, J., Huse, K., Rosenstiel, P., Albrecht, M., Stenzel, A., Nagy, M., Gaede, K. I., Franke, A., Haesler, R., Koch, A, Lengauer, T., Seegert, D., Reiling, N., Ehlers, S., Schwinger, E., Platzer, M., Krawczak, M., Müller-Quernheim, J., Schürmann, M., Schreiber, S. 2005. Sarcoidosis is associated with a truncating splice site mutation in BTNL2. Nat. Genet. 37: 357-364-364.

Walunas, T. L., Lenschow, D. J., Bakker, C. Y., Linsley, P. S., Freeman, G. J., Green, J. M., Thompson, C. B., and Bluestone, J. A. 1994. CTLA-4 can function as a negative regulator of T cell activation. Immunity. 1:405-413.

Walunas, T. L., and Bluestone, J. A. 1998. CTLA-4 regulates tolerance induction and T cell differentiation in vivo. J. Immunol. 160:3855-3860.

Waterhouse, P., Penninger, J. M., Timms, E., Wakeham, A., Shahinian, A., Lee, K. P., Thompson, C. B., Griesser, H., and Mak, T. W. 1995. Lymphoproliferative disorders with early lethality in mice deficient in Ctla-4. Science. 270: 985-988.

Waterhouse, P., Marengere, L. E. M., Mittrucker, H.-W., and Mak, T. W. 1996. CTLA-4, a negative regulator of T-lymphocyte activation. Immnunol. Rev. 153:183-207.

Williams, A. F., and Barclay, A. N. 1988. The immunoglobulin superfamily-domains for cell surface recognition. Annu. Rev. Immunol. 6: 381-405.

Wolf, S. F., Sieburth, D., and Sypek, J. 1994. Interleukin-12: a key modulator of immune function. Stem Cells Dayt. 12:154-168.

Yi-qun, Z., Lorre, K., de Boer, M., and Ceuppens, J. L. 1997. B7-blocking agents, alone or in combination with cyclosporin A, induce antigen-specific anergy of human memory T cells. J. Immunol. 158:4734-4740.

1. Sharpe, A. H. and G. J. Freeman, *The B7-CD28 superfamily*. Nat Rev Immunol, 2002. 2(2): p. 116-26.
2. Greenwald, R. J., G. J. Freeman, and A. H. Sharpe, *The B7 family revisited*. Annu Rev Immunol, 2005. 23: p. 515-48.
3. Croft, M., *Co-stimulatory members of the TNFR family: keys to effective T-cell immunity?* Nat Rev Immunol, 2003. 3(8): p. 609-20.
4. Watts, T. H., *TNF/TNFR family members in costimulation of T cell responses*. Annu Rev Immunol, 2005. 23: p. 23-68.
5. Ishida, Y., et al., *Induced expression of PD-1, a novel member of the immunoglobulin gene superfamily, upon programmed cell death*. Embo J, 1992. 11(11): p. 3887-95.
6. Chambers, C. A. and J. P. Allison, *Co-stimulation in T cell responses*. Curr Opin Immunol, 1997. 9(3): p. 396-404.
7. Lenschow, D. J., T. L. Walunas, and J. A. Bluestone, *CD28/B7 system of T cell costimulation*. Annu Rev Immunol, 1996. 14: p. 233-58.
8. June, C. H., et al., *The B7 and CD28 receptor families*. Immunol Today, 1994. 15(7): p. 321-31.
9. Boise, L. H., et al., *CD28 costimulation can promote T cell survival by enhancing the expression of Bcl-XL*. Immunity, 1995. 3(1): p. 87-98.
10. Linsley, P. S., et al., *CTLA-4 is a second receptor for the B cell activation antigen B7*. J Exp Med, 1991. 174(3): p. 561-9.
11. Tazi-Ahnini, R., et al., *Cloning, localization, and structure of new members of the butyrophilin gene family in the juxta-telomeric region of the major histocompatibility complex*. Immunogenetics, 1997. 47(1): p. 55-63.
12. Rhodes, D. A., et al., *The cluster of BTN genes in the extended major histocompatibility complex*. Genomics, 2001. 71(3): p. 351-62.
13. Henry, J., et al., *Cloning, structural analysis, and mapping of the B30 and B7 multigenic families to the major histocompatibility complex (MHC) and other chromosomal regions*. Immunogenetics, 1997. 46(5): p. 383-95.
14. Henry, J., et al., *B30.2-like domain proteins: a growing family*. Biochem Biophys Res Commun, 1997. 235(1): p. 162-5.
15. Ogg, S. L., et al., *Expression of butyrophilin (Btn1a1) in lactating mammary gland is essential for the regulated secretion of milk-lipid droplets*. Proc Natl Acad Sci USA, 2004. 101(27): p. 10084-9.
16. Robenek, H., et al., *Butyrophilin controls milk fat globule secretion*. Proc Natl Acad Sci USA, 2006. 103 (27): p. 10385-90.
17. Ishii, T., et al., *Carboxy-terminal cytoplasmic domain of mouse butyrophilin specifically associates with a 150-kDa protein of mammary epithelial cells and milk fat globule membrane*. Biochim Biophys Acta, 1995. 1245(3): p. 285-92.
18. Henry, J., et al., *830.2-like domain proteins: update and new insights into a rapidly expanding family of proteins*. Mol Biol Evol, 1998. 15(12): p. 1696-705.
19. Ruddy, D. A., et al., *A 1.1-Mb transcript map of the hereditary hemochromatosis locus*. Genome Res, 1997. 7(5): p. 441-56.
20. Henry, J., M. M. Miller, and P. Pontarotti, *Structure and evolution of the extended B7 family*. Immunol Today, 1999. 20(6): p. 285-8.

21. Compte, E., et al., *Frontline: Characterization of BT3 molecules belonging to the B7 family expressed on immune cells*. Eur J Immunol, 2004. 34(8): p. 2089-99.
22. Malcherek, G., L. Mayr, P. Roda-Navarro, D. Rhodes, N. Miller, and J. Trowsdale. 2007. *The B7 homolog butyrophilin BTN2A1 is a novel ligand for DC-SIGN*. J. Immunol. 179: 3804-3811.
23. Nguyen, T., X. K. Liu, Y. Zhang, and C. Dong. 2006. *BTNL2, a butyrophilin-like molecule that functions to inhibit T cell activation*. J. Immunol. 176: 7354-736
24. Arnett, H. A., S. S. Escobar, E. Gonzalez-Suarez, A. L. Budelsky, L. A. Steffen, N. Boiani, M. Zhang, G. Siu, A. W. Brewer, and J. L. Viney. 2007. *BTNL2, a butyrophilin/B7-like molecule, is a negative costimulatory molecule modulated in intestinal inflammation*. J. Immunol. 178: 1523-1533.
25. Xerri L, Devilard E, Hassoun J, et al. In vivo expression of the CTLA4 inhibitory receptor in malignant and reactive cells from human lymphomas. J Pathol. 1997; 183: 182-187.
26. Yamashiro H, Yoshizaki S, Tadaki T, Egawa K and Seo N. 2010. Stimulation of human butyrophilin 3 molecules results in negative regulation of cellular immunity.
27. Firaguay G and Nunes J A. 2009. Analysis of signaling events by dynamic phosphoflow cytometry. Science Signaling.

References Cited in Example 3 are the Following

1. Tanaka, Y. et coll. Natural and synthetic non-peptide antigens recognized by human gamma delta T cells. *Nature* 375, 155-8 (1995).
2. Halary, F. et coll. Control of self-reactive cytotoxic T lymphocytes expressing gamma delta T cell receptors by natural killer inhibitory receptors. *Eur J Immunol* 27, 2812-21 (1997).
3. Das, H. et coll. MICA engagement by human Vgamma2Vdelta2 T cells enhances their antigen-dependent effector function. *Immunity* 15, 83-93 (2001).
4. Deetz, C. O. et coll. Gamma interferon secretion by human Vgamma2Vdelta2 T cells after stimulation with antibody against the T-cell receptor plus the Toll-Like receptor 2 agonist Pam3Cys. *Infect Immun* 74, 4505-11 (2006).
5. Wesch, D. et coll. Direct costimulatory effect of TLR3 ligand poly(I:C) on human gamma delta T lymphocytes. *J Immunol* 176, 1348-54 (2006).
6. Rincon-Orozco, B. et coll. Activation of V gamma 9V delta 2 T cells by NKG2D. *J Immunol* 175, 2144-51 (2005).
7. Boyden, L. M. et coll. Skint1, the prototype of a newly identified immunoglobulin superfamily gene cluster, positively selects epidermal gammadelta T cells. *Nat Genet* 40, 656-62 (2008).
8. Stammers, M. et coll. BTL-II: a polymorphic locus with homology to the butyrophilin gene family, located at the border of the major histocompatibility complex class II and class III regions in human and mouse. *Immunogenetics* 51, 373-82 (2000).
9. Arnett, H. A. et coll. BTNL2, a butyrophilin/B7-like molecule, is a negative costimulatory molecule modulated in intestinal inflammation. *J Immunol* 178, 1523-33 (2007).
10. Compte, E. et coll. Frontline: Characterization of BT3 molecules belonging to the B7 family expressed on immune cells. *Eur J Immunol* 34, 2089-99 (2004).
11. Mann, M. et coll. Analysis of protein phosphorylation using mass spectrometry: deciphering the phosphoproteome. *Trends Biotechnol* 20, 261-8 (2002).
12. Cantin, G. T. et coll. Combining protein-based IMAC, peptide-based IMAC, and MudPIT for efficient phosphoproteomic analysis. *J Proteome Res* 7, 1346-51 (2008).
13. Villén, J. et coll. Large-scale phosphorylation analysis of mouse liver. *Proc Natl Acad Sci USA* 104, 1488-93 (2007).
14. Park, H. et coll. A point mutation in the murine Hem1 gene reveals an essential role for Hematopoietic protein 1 in lymphopoiesis and innate immunity. *J Exp Med* 205, 2899-913 (2008).
15. Wang, Y. et coll. Profiling signaling polarity in chemotactic cells. *Proc Natl Acad Sci USA* 104, 8328-33 (2007).
16. Tzivion, G., Luo, Z. & Avruch, J. A dimeric 14-3-3 protein is an essential cofactor for Raf kinase activity. *Nature* 394, 88-92 (1998).
17. Di Bartolo, V. et coll. A novel pathway down-modulating T cell activation involves HPK-1-dependent recruitment of 14-3-3 proteins on SLP-76. *J Exp Med* 204, 681-91 (2007).
18. Zhang, H. et coll. RIP1-mediated AIP1 phosphorylation at a 14-3-3-binding site is critical for tumor necrosis factor-induced ASK1-JNK/p38 activation. *J Biol Chem* 282, 14788-96 (2007).
19. Parker, F. et coll. A Ras-GTPase-activating protein SH3-domain-binding protein. *Mol Cell Biol* 16, 2561-9 (1996).
20. Tourrière, H. et coll. The RasGAP-associated endoribonuclease G3BP assembles stress granules. *J Cell Biol* 160, 823-31 (2003).
21. Rahmouni, S. et coll. Removal of C-terminal SRC kinase from the immune synapse by a new binding protein. *Mol Cell Biol* 25, 2227-41 (2005).
22. Grewal, T. et coll. Annexin A6 stimulates the membrane recruitment of p120GAP to modulate Ras and Raf-1 activity. *Oncogene* 24, 5809-20 (2005).
23. Li, M., Makkinje, A. & Damuni, Z. The myeloid leukemia-associated protein SET is a potent inhibitor of protein phosphatase 2A. *J Biol Chem* 271, 11059-62 (1996).
24. Grantham, J. et coll. Eukaryotic chaperonin containing T-complex polypeptide 1 interacts with filamentous actin and reduces the initial rate of actin polymerization in vitro. *Cell Stress Chaperones* 7, 235-42 (2002).
25. Williams, J. C., Xie, H. & Hendrickson, W. A. Crystal structure of dynein light chain TcTex-1. *J Biol Chem* 280, 21981-6 (2005).
26. Sachdev, P. et coll. G protein beta gamma subunit interaction with the dynein light-chain component Tctex-1 regulates neurite outgrowth. *EMBO J* 26, 2621-32 (2007).
27. Schnapp, B. J. & Reese, T. S. Dynein is the motor for retrograde axonal transport of organelles. *Proc Natl Acad Sci USA* 86, 1548-52 (1989).
28. Wang, Y. et coll. Rim is a putative Rab3 effector in regulating synaptic-vesicle fusion. *Nature* 388, 593-8 (1997).
29. Martin-Cófreces, N. B. et coll. MTOC translocation modulates IS formation and controls sustained T cell signaling. *J Cell Biol* 182, 951-62 (2008).
30. Stremlau, M. et coll. The cytoplasmic body component TRIM5alpha restricts HIV-1 infection in Old World monkeys. *Nature* 427, 848-53 (2004).

31. Jéru, I. et coll. Interaction of pyrin with 14.3.3 in an isoform-specific and phosphorylation-dependent manner regulates its translocation to the nucleus. *Arthritis Rheum* 52, 1848-57 (2005).
32. Mansfield, E. et coll. The familial Mediterranean fever protein, pyrin, associates with microtubules and colocalizes with actin filaments. *Blood* 98, 851-9 (2001).
33. Yu, J. et coll. Pyrin activates the ASC pyroptosome in response to engagement by autoinflammatory PSTPIP1 mutants. *Mol Cell* 28, 214-27 (2007).
34. Badour, K. et coll. The Wiskott-Aldrich syndrome protein acts downstream of CD2 and the CD2AP and PSTPIP1 adaptors to promote formation of the immunological synapse. *Immunity* 18, 141-54 (2003).
35. Côté, J. et coll. PSTPIP is a substrate of PTP-PEST and serves as a scaffold guiding PTP-PEST toward a specific dephosphorylation of WASP. *J Biol Chem* 277, 2973-86 (2002).
36. Maeda, Y. et coll. Critical role of host gammadelta T cells in experimental acute graft versus-host disease. *Blood* 106, 749-55 (2005).
37. Pabst, C. et coll. The graft content of donor T cells expressing gamma delta TCR+ and CD4+foxp3+ predicts the risk of acute graft versus host disease after transplantation of allogeneic peripheral blood stem cells from unrelated donors. *Clin Cancer Res* 13, 2916-22 (2007).
38. Fitch, W. Toward defining the courfe of evolution: minimum change for a specific tree topology. *Systematic Zoology* 406-416 (1971).
39. Felsenstein, J. Evolutionary trees from DNA sequences: a maximum likelihood approach. *J Mol Evol* 17, 368-76 (1981).
40. Saitou, N. & Nei, M. The neighbor-joining method: a new method for reconstructing phylogenetic trees. *Mol Biol Evol* 4, 406-25 (1987).
41. Gouret, P. et coll. FIGENIX: Intelligent automation of genomic annotation: expertise integration in a new software platform. *BMC Bioinformatics* 6, 198(2005).

References Cited in Example 4 are the Following

1. Butturini A, Bortin M M, Gale R P. Graft-versus-leukemia following bone marrow transplantation. Bone Marrow Transplant. 1987; 2(3):233-242.
2. Kunzmann V, Bauer E, Feurle J, et al. Stimulation of gammadelta T cells by aminobisphosphonates and induction of antiplasma cell activity in multiple myeloma. Blood. 2000; 96(2):384-392.
3. Castella B, Vitale C, Coscia M, Massaia M. Vγ9Vδ2 T cell-based immunotherapy in hematological malignancies: from bench to bedside. Cell. Mol. Life Sci. CMLS. 2011; 68(14):2419-2432.
4. Kabelitz D, Wesch D, Pitters E, Zöller M. Characterization of tumor reactivity of human V gamma 9V delta 2 gamma delta T cells in vitro and in SCID mice in vivo. J. Immunol. Baltim. Md. 1950. 2004; 173(11):6767-6776.
5. Norell H, Moretta A, Silva-Santos B, Moretta L. At the Bench: Preclinical rationale for exploiting NK cells and γδ T lymphocytes for the treatment of high-risk leukemias. J. Leukoc. Biol. 2013; 94(6):1123-1139.
6. Locatelli F, Merli P, Rutella S. At the Bedside: Innate immunity as an immunotherapy tool for hematological malignancies. J. Leukoc. Biol. 2013; 94(6):1141-1157.
7. Godder K T, Henslee-Downey P J, Mehta J, et al. Long term disease-free survival in acute leukemia patients recovering with increased gammadelta T cells after partially mismatched related donor bone marrow transplantation. Bone Marrow Transplant. 2007; 39(12):751-757.
8. Meeh P F, King M, O'Brien R L, et al. Characterization of the gammadelta T cell response to acute leukemia. Cancer Immunol. Immunother. CII. 2006; 55(9):1072-1080.
9. Gober H-J, Kistowska M, Angman L, et al. Human T cell receptor gammadelta cells recognize endogenous mevalonate metabolites in tumor cells. J. Exp. Med. 2003; 197(2):163-168.
10. Correia D V, Lopes A, Silva-Santos B. Tumor cell recognition by γδ T lymphocytes: T-cell receptor vs. NK-cell receptors. Oncoimmunology. 2013; 2(1):e22892.
11. Bottino C, Castriconi R, Pende D, et al. Identification of PVR (CD155) and Nectin-2 (CD112) as cell surface ligands for the human DNAM-1 (CD226) activating molecule. J. Exp. Med. 2003; 198(4):557-567.
12. Rincon-Orozco B, Kunzmann V, Wrobel P, et al. Activation of V gamma 9V delta 2 T cells by NKG2D. J. Immunol. Baltim. Md. 1950. 2005; 175(4):2144-2151.
13. Gertner-Dardenne J, Castellano R, Mamessier E, et al. Human Vγ9Vδ2 T cells specifically recognize and kill acute myeloid leukemic blasts. J. Immunol. 2012; 188(9): 4701-4708.
14. Li J, Herold M J, Kimmel B, et al. Reduced expression of the mevalonate pathway enzyme farnesyl pyrophosphate synthase unveils recognition of tumor cells by Vgamma9Vdelta2 T cells. J. Immunol. 2009; 182(12): 8118-8124.
15. Kunzmann V, Smetak M, Kimmel B, et al. Tumor-promoting versus tumor-antagonizing roles of γδ T cells in cancer immunotherapy: results from a prospective phase I/II trial. J. Immunother. 2012; 35(2):205-213.
16. Coscia M, Vitale C, Peola S, et al. Dysfunctional Vγ9Vδ2 T cells are negative prognosticators and markers of dysregulated mevalonate pathway activity in chronic lymphocytic leukemia cells. Blood. 2012; 120(16):3271-3279.
17. Wilhelm M, Smetak M, Schaefer-Eckart K, et al. Successful adoptive transfer and in vivo expansion of haploidentical γδ T cells. J. Transl. Med. 2014; 12:45.
18. Gundermann S, Klinker E, Kimmel B, et al. A comprehensive analysis of primary acute myeloid leukemia identifies biomarkers predicting susceptibility to human allogeneic Vγ9Vδ2 T cells. J. Immunother. 2014; 37(6):321-330.
19. Compte E, Pontarotti P, Collette Y, Lopez M, Olive D. Frontline: Characterization of BT3 molecules belonging to the B7 family expressed on immune cells. Eur. J. Immunol. 2004; 34(8):2089-2099.
20. Le Page C, Marineau A, Bonza P K, et al. BTN3A2 expression in epithelial ovarian cancer is associated with higher tumor infiltrating T cells and a better prognosis. PloS One. 2012; 7(6):e38541.
21. Messal N, Mamessier E, Sylvain A, et al. Differential role for CD277 as a co-regulator of the immune signal in T and NK cells. Eur. J. Immunol. 2011; 41(12):3443-3454.
22. Simone R, Barbarat B, Rabellino A, et al. Ligation of the BT3 molecules, members of the B7 family, enhance the proinflammatory responses of human monocytes and monocyte-derived dendritic cells. Mol. Immunol. 2010; 48(1-3):109-118.
23. Harly C, Guillaume Y, Nedellec S, et al. Key implication of CD277/butyrophilin-3 (BTN3A) in cellular stress sensing by a major human γδ T-cell subset. Blood. 2012; 120(11):2269-2279.

24. Wang H, Henry O, Distefano M D, et al. Butyrophilin 3A1 plays an essential role in prenyl pyrophosphate stimulation of human Vγ2Vδ2 T cells. J. Immunol. 2013; 191(3):1029-1042.
25. Sandstrom A, Peigné C-M, Lèger A, et al. The intracellular B30.2 domain of butyrophilin 3A1 binds phosphoantigens to mediate activation of human Vγ9Vδ2 T cells. Immunity. 2014; 40(4):490-500.
26. Palakodeti A, Sandstrom A, Sundaresan L, et al. The molecular basis for modulation of human Vγ9Vδ2 T cell responses by CD277/butyrophilin-3 (BTN3A)-specific antibodies. J. Biol. Chem. 2012; 287(39):32780-32790.
27. Mortier E, Quéméner A, Vusio P, et al. Soluble interleukin-15 receptor alpha (IL-15R alpha)-sushi as a selective and potent agonist of IL-15 action through IL-15R beta/gamma. Hyperagonist IL-15×IL-15R alpha fusion proteins. J. Biol. Chem. 2006; 281(3):1612-1619.
28. Gertner J, Wiedemann A, Poupot M, Fournié J-J. Human gammadelta T lymphocytes strip and kill tumor cells simultaneously. Immunol. Lett. 2007; 110(1):42-53.
29. Gertner-Dardenne J, Poupot M, Gray B, Fournié J-J. Lipophilic fluorochrome trackers of membrane transfers between immune cells. Immunol. Invest. 2007; 36(5-6): 665-685.
30. Sanchez P V, Perry R L, Sarry J E, et al. A robust xenotransplantation model for acute myeloid leukemia. Leukemia. 2009; 23(11):2109-2117.
31. Pende D, Spaggiari G M, Marcenaro S, et al. Analysis of the receptor-ligand interactions in the natural killer-mediated lysis of freshly isolated myeloid or lymphoblastic leukemias: evidence for the involvement of the Poliovirus receptor (CD155) and Nectin-2 (CD112). Blood. 2005; 105(5):2066-2073.
32. Moretta L, Bottino C, Pende D, et al. Human natural killer cells: Molecular mechanisms controlling NK cell activation and tumor cell lysis. Immunol. Lett. 2005; 100(1):7-13.
33. Knorr D A, Bachanova V, Verneris M R, Miller J S. Clinical utility of natural killer cells in cancer therapy and transplantation. Semin. Immunol. 2014; 26(2):161-172.
34. Uchida R, Ashihara E, Sato K, et al. Gamma delta T cells kill myeloma cells by sensing mevalonate metabolites and ICAM-1 molecules on cell surface. Biochem. Biophys. Res. Commun. 2007; 354(2):613-618.
35. Liu Z, Guo B, Lopez R D. Expression of intercellular adhesion molecule (ICAM)-1 or ICAM-2 is critical in determining sensitivity of pancreatic cancer cells to cytolysis by human gammadelta-T cells: implications in the design of gammadelta-T-cell-based immunotherapies for pancreatic cancer. J. Gastroenterol. Hepatol. 2009; 24(5):900-911.
36. Ruggeri L, Capanni M, Urbani E, et al. Effectiveness of donor natural killer cell alloreactivity in mismatched hematopoietic transplants. Science. 2002; 295(5562): 2097-2100.
37. Idrees A S M, Sugie T, Inoue C, et al. Comparison of γδ T cell responses and farnesyl diphosphate synthase inhibition in tumor cells pretreated with zoledronic acid. Cancer Sci. 2013; 104(5):536-542.
38. Decaup E, Duault C, Bezombes C, et al. Phosphoantigens and butyrophilin 3A1 induce similar intracellular activation signaling in human TCRVγ9+γδ T lymphocytes. Immunol. Lett. 2014; 161(1):133-137.
39. Wilhelm M, Kunzmann V, Eckstein S, et al. Gammadelta T cells for immune therapy of patients with lymphoid malignancies. Blood. 2003; 102(1):200-206.
40. Riaño F, Karunakaran M M, Starick L, et al. Vγ9Vδ2 TCR-activation by phosphorylated antigens requires butyrophilin 3 A1 (BTN3A1) and additional genes on human chromosome 6. Eur. J. Immunol. 2014; 44(9): 2571-2576.
41. Hodi F S, O'Day S J, McDermott D F, et al. Improved survival with ipilimumab in patients with metastatic melanoma. N. Engl. J. Med. 2010; 363(8):711-723.
42. Topalian S L, Hodi F S, Brahmer J R, et al. Safety, activity, and immune correlates of anti-PD-1 antibody in cancer. N. Engl. J. Med. 2012; 366(26):2443-2454.
43. Bashey A, Medina B, Corringham S, et al. CTLA4 blockade with ipilimumab to treat relapse of malignancy after allogeneic hematopoietic cell transplantation. Blood. 2009; 113(7):1581-1588.
44. Ansell S M, Lesokhin A M, Borrello I, et al. PD-1 Blockade with Nivolumab in Relapsed or Refractory Hodgkin's Lymphoma. N. Engl. J. Med. 2014;

---

The invention claimed is:

1. An isolated anti-CD277 antibody, comprising the following CDRs:

|  | Amino acid sequence |
|---|---|
| H-CDR1 | RYYMY (SEQ ID NO: 27) |
| H-CDR2 | EINPNNGGTKFNEKFKN (SEQ ID NO: 28) |
| H-CDR3 | EDDYDGTPFAMDY (SEQ ID NO: 29) |
| L-CDR1 | HASQNINVWLS (SEQ ID NO: 30) |
| L-CDR2 | KASNLHT (SEQ ID NO: 31) |
| L-CDR3 | QQGQTYPYT (SEQ ID NO: 32). |

2. The anti-CD277 antibody of claim 1, wherein said anti-CD277 antibody is a chimeric or humanized antibody.

3. An anti-CD277 antibody having the CDRs of mAb7.2, said mAb7.2 being obtained from the hybridoma accessible under CNCM deposit number I-4401.

4. The anti-CD277 antibody of claim 1, wherein said anti-CD277 antibody is a murine antibody mAb7.2 as obtained from the hybridoma accessible under CNCM deposit number I-4401.

5. The anti-CD277 antibody of claim 1, wherein said anti-CD277 antibody:
  activates the cytolytic function, cytokine production and proliferation of Vγ9/Vδ2 T cells,
  costimulates T cells together with CD3-TCR,
  costimulates T cells in addition to CD28-B7 costimulation, and/or
  increases the activity and/or survival of monocytes and dendritic cells.

6. A pharmaceutical composition comprising the anti-CD277 antibody of claim 1, in combination with one or more pharmaceutically acceptable excipients.

7. The pharmaceutical composition of claim 6, wherein said pharmaceutical composition is an injectable solution.

8. The pharmaceutical composition of claim 6, wherein said pharmaceutical composition is formulated for intravenous or subcutaneous administration.

9. The anti-CD277 antibody of claim 3, wherein said anti-CD277 antibody:
  activates the cytolytic function, cytokine production and proliferation of Vγ9/Vδ2 T cells,
  costimulates T cells together with CD3-TCR,
  costimulates T cells in addition to CD28-B7 costimulation, and/or
  increases the activity and/or survival of monocytes and dendritic cells.

10. A pharmaceutical composition comprising the anti-CD277 antibody of claim 3, in combination with one or more pharmaceutically acceptable excipients.

11. The pharmaceutical composition of claim 10, wherein said pharmaceutical composition is an injectable solution.

12. The pharmaceutical composition of claim 10, wherein said pharmaceutical composition is formulated for intravenous or subcutaneous administration.

* * * * *

SEQUENCE LISTING

```
<160> NUMBER OF SEQ ID NOS: 60

<210> SEQ ID NO 1
<211> LENGTH: 15
<212> TYPE: DNA
<213> ORGANISM: Mus musculus

<400> SEQUENCE: 1
aggtactatt tgtac                                                    15

<210> SEQ ID NO 2
<211> LENGTH: 51
<212> TYPE: DNA
<213> ORGANISM: Mus musculus

<400> SEQUENCE: 2
gagataaatc ctaacaatgg tggtactaag ttcaatgaga agttcaagag c             51

<210> SEQ ID NO 3
<211> LENGTH: 39
<212> TYPE: DNA
```

<213> ORGANISM: Mus musculus

<400> SEQUENCE: 3
gaggatgatt acgacgggac ccccgatgct atggactac            39

<210> SEQ ID NO 4
<211> LENGTH: 33
<212> TYPE: DNA
<213> ORGANISM: Mus musculus

<400> SEQUENCE: 4
catgccagtc agaacattaa tctttggtta agc                  33

<210> SEQ ID NO 5
<211> LENGTH: 21
<212> TYPE: DNA
<213> ORGANISM: Mus musculus

<400> SEQUENCE: 5
agggcttcca acttgcacac a                               21

<210> SEQ ID NO 6
<211> LENGTH: 27
<212> TYPE: DNA
<213> ORGANISM: Mus musculus

<400> SEQUENCE: 6
caacagggtc atagttatcc gtacacg                         27

<210> SEQ ID NO 7
<211> LENGTH: 5
<212> TYPE: PRT
<213> ORGANISM: Mus musculus

<400> SEQUENCE: 7

Arg Tyr Tyr Leu Tyr
1               5

<210> SEQ ID NO 8
<211> LENGTH: 17
<212> TYPE: PRT
<213> ORGANISM: Mus musculus

<400> SEQUENCE: 8

Glu Ile Asn Pro Asn Asn Gly Gly Thr Lys Phe Asn Glu Lys Phe Lys
1               5                   10                  15

Ser

<210> SEQ ID NO 9
<211> LENGTH: 13
<212> TYPE: PRT
<213> ORGANISM: Mus musculus

<400> SEQUENCE: 9

Glu Asp Asp Tyr Asp Gly Thr Pro Asp Ala Met Asp Tyr
1               5                   10

<210> SEQ ID NO 10
<211> LENGTH: 11
<212> TYPE: PRT
<213> ORGANISM: Mus musculus

<400> SEQUENCE: 10

His Ala Ser Gln Asn Ile Asn Leu Trp Leu Ser
1               5                  10

<210> SEQ ID NO 11
<211> LENGTH: 7
<212> TYPE: PRT
<213> ORGANISM: Mus musculus

<400> SEQUENCE: 11

Arg Ala Ser Asn Leu His Thr
1               5

<210> SEQ ID NO 12
<211> LENGTH: 9
<212> TYPE: PRT
<213> ORGANISM: Mus musculus

<400> SEQUENCE: 12

Gln Gln Gly His Ser Tyr Pro Tyr Thr
1               5

<210> SEQ ID NO 13
<211> LENGTH: 423
<212> TYPE: DNA
<213> ORGANISM: Mus musculus

<400> SEQUENCE: 13

```
atgggatgga gctatatcat cctcttttg gtaacaacag caacaggtgt ccactcccag      60
gtccaactgc agcagtctgg ggctgaactg gtgaagcctg gggcttcagt gaagttgtcc    120
tgcaaggctt ctggctacac cttcaccagg tactatttgt actgggtgaa acagaggcct    180
ggacaaggcc ttgagtggat tggagagata aatcctaaca atggtggtac taagttcaat    240
gagaagttca gagcaaggc cacactgact gtagacaaat cctccagaac aacatacata    300
caactcagca gcctgacatc tgaggactct gcggtctatt actgttcaag agaggatgat    360
tacgacggga cccccgatgc tatggactac tggggtcaag aaccgcagt caccgtctcc    420
tca                                                                  423
```

<210> SEQ ID NO 14
<211> LENGTH: 141
<212> TYPE: PRT
<213> ORGANISM: Mus musculus

<400> SEQUENCE: 14

Met Gly Trp Ser Tyr Ile Ile Leu Phe Leu Val Thr Thr Ala Thr Gly
1               5                   10                  15

Val His Ser Gln Val Gln Leu Gln Gln Ser Gly Ala Glu Leu Val Lys
                20                  25                  30

Pro Gly Ala Ser Val Lys Leu Ser Cys Lys Ala Ser Gly Tyr Thr Phe
            35                  40                  45

Thr Arg Tyr Tyr Leu Tyr Trp Val Lys Gln Arg Pro Gly Gln Gly Leu
        50                  55                  60

Glu Trp Ile Gly Glu Ile Asn Pro Asn Asn Gly Gly Thr Lys Phe Asn
65                  70                  75                  80

Glu Lys Phe Lys Ser Lys Ala Thr Leu Thr Val Asp Lys Ser Ser Arg
                85                  90                  95

Thr Thr Tyr Ile Gln Leu Ser Ser Leu Thr Ser Glu Asp Ser Ala Val
            100                 105                 110

Tyr Tyr Cys Ser Arg Glu Asp Asp Tyr Asp Gly Thr Pro Asp Ala Met

Asp Tyr Trp Gly Gln Gly Thr Ala Val Thr Val Ser Ser
    130             135             140

<210> SEQ ID NO 15
<211> LENGTH: 381
<212> TYPE: DNA
<213> ORGANISM: Mus musculus

<400> SEQUENCE: 15
atgagggtcc ttgctgagct cctggggctg ctgctgttct gcttttagg tgtgagatgt      60 gacatccaga tgaaccagtc tccatccagt ctgtctgcat cccttggaga cacaattacc    120
atcacttgcc atgccagtca gaacattaat ctttggttaa gctggtacca gcagagacca    180
ggaaatattc ctaaacttct gatctatagg gcttccaact tgcacacagg cgtcccatca    240
aggtttagtg gcagtggatc tgcaacaggt ttcacattaa ccatcagcag cctgcagcct    300
gaagacattg ccacttacta ctgtcaacag ggtcatagtt atccgtacac gttcggaggg    360
gggaccaaac tggacataaa a                                              381

<210> SEQ ID NO 16
<211> LENGTH: 127
<212> TYPE: PRT
<213> ORGANISM: Mus musculus

<400> SEQUENCE: 16

Met Arg Val Leu Ala Glu Leu Leu Gly Leu Leu Leu Phe Cys Phe Leu
1               5                   10                  15

Gly Val Arg Cys Asp Ile Gln Met Asn Gln Ser Pro Ser Ser Leu Ser
            20                  25                  30

Ala Ser Leu Gly Asp Thr Ile Thr Ile Thr Cys His Ala Ser Gln Asn
        35                  40                  45

Ile Asn Leu Trp Leu Ser Trp Tyr Gln Gln Arg Pro Gly Asn Ile Pro
    50                  55                  60

Lys Leu Leu Ile Tyr Arg Ala Ser Asn Leu His Thr Gly Val Pro Ser
65                  70                  75                  80

Arg Phe Ser Gly Ser Gly Ser Ala Thr Gly Phe Thr Leu Thr Ile Ser
                85                  90                  95

Ser Leu Gln Pro Glu Asp Ile Ala Thr Tyr Tyr Cys Gln Gln Gly His
            100                 105                 110

Ser Tyr Pro Tyr Thr Phe Gly Gly Gly Thr Lys Leu Asp Ile Lys
        115                 120                 125

<210> SEQ ID NO 17
<211> LENGTH: 366
<212> TYPE: DNA
<213> ORGANISM: Mus musculus

<400> SEQUENCE: 17
caggtccaac tgcagcagtc tggggctgaa ctggtgaagc ctggggcttc agtgaagttg     60
tcctgcaagg cttctggcta caccttcacc aggtactatt tgtactgggt gaaacagagg    120
cctggacaag gccttgagtg gattggagag ataaatccta acaatggtgg tactaagttc    180
aatgagaagt tcaagagcaa ggccacactg actgtagaca atcctccag aacaacatac     240 atacaactca gcagcctgac atctgaggac tctgcggtct attactgttc aagagaggat    300
gattacgacg ggacccccga tgctatggac tactggggtc aaggaaccgc agtcaccgtc    360
tcctca                                                                    366

<210> SEQ ID NO 18
<211> LENGTH: 122
<212> TYPE: PRT
<213> ORGANISM: Mus musculus

<400> SEQUENCE: 18

Gln Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Arg Tyr
            20                  25                  30

Tyr Leu Tyr Trp Val Lys Gln Arg Pro Gly Gln Gly Leu Glu Trp Ile
        35                  40                  45

Gly Glu Ile Asn Pro Asn Asn Gly Gly Thr Lys Phe Asn Glu Lys Phe
    50                  55                  60

Lys Ser Lys Ala Thr Leu Thr Val Asp Lys Ser Ser Arg Thr Thr Tyr
65                  70                  75                  80

Ile Gln Leu Ser Ser Leu Thr Ser Glu Asp Ser Ala Val Tyr Tyr Cys
                85                  90                  95

Ser Arg Glu Asp Asp Tyr Asp Gly Thr Pro Asp Ala Met Asp Tyr Trp
            100                 105                 110

Gly Gln Gly Thr Ala Val Thr Val Ser Ser
        115                 120

<210> SEQ ID NO 19
<211> LENGTH: 321
<212> TYPE: DNA
<213> ORGANISM: Mus musculus

<400> SEQUENCE: 19
gacatccaga tgaaccagtc tccatccagt ctgtctgcat cccttggaga cacaattacc     60
atcacttgcc atgccagtca gaacattaat ctttggttaa ctggtaccagcagagacca    120 ggaaatattc ctaaacttct gatctatagg gcttccaact tgcacacagg cgtcccatca   180
aggtttagtg gcagtggatc tgcaacaggt ttcacattaa ccatcagcag cctgcagcct   240
gaagacattg ccacttacta ctgtcaacag ggtcatagtt atccgtacac gttcggaggg   300
gggaccaaac tggacataaa a                                              321

<210> SEQ ID NO 20
<211> LENGTH: 107
<212> TYPE: PRT
<213> ORGANISM: Mus musculus

<400> SEQUENCE: 20

Asp Ile Gln Met Asn Gln Ser Pro Ser Ser Leu Ser Ala Ser Leu Gly
1               5                   10                  15

Asp Thr Ile Thr Ile Thr Cys His Ala Ser Gln Asn Ile Asn Leu Trp
            20                  25                  30

Leu Ser Trp Tyr Gln Gln Arg Pro Gly Asn Ile Pro Lys Leu Leu Ile
        35                  40                  45

Tyr Arg Ala Ser Asn Leu His Thr Gly Val Pro Ser Arg Phe Ser Gly
    50                  55                  60

Ser Gly Ser Ala Thr Gly Phe Thr Leu Thr Ile Ser Ser Leu Gln Pro
65                  70                  75                  80

Glu Asp Ile Ala Thr Tyr Tyr Cys Gln Gln Gly His Ser Tyr Pro Tyr
                85                  90                  95

Thr Phe Gly Gly Gly Thr Lys Leu Asp Ile Lys
            100                 105

<210> SEQ ID NO 21
<211> LENGTH: 15
<212> TYPE: DNA
<213> ORGANISM: Mus musculus

<400> SEQUENCE: 21
agatactata tgtat                                                   15

<210> SEQ ID NO 22
<211> LENGTH: 51
<212> TYPE: DNA
<213> ORGANISM: Mus musculus

<400> SEQUENCE: 22
gagattaatc ctaacaatgg tggtactaag ttcaatgaga agttcaagaa c            51

<210> SEQ ID NO 23
<211> LENGTH: 39
<212> TYPE: DNA
<213> ORGANISM: Mus musculus

<400> SEQUENCE: 23
gaggatgatt acgacgggac cccctttgct atggactac                         39

<210> SEQ ID NO 24
<211> LENGTH: 33
<212> TYPE: DNA
<213> ORGANISM: Mus musculus

<400> SEQUENCE: 24
catgccagtc agaacattaa tgtttggtta agc                               33

<210> SEQ ID NO 25
<211> LENGTH: 21
<212> TYPE: DNA
<213> ORGANISM: Mus musculus

<400> SEQUENCE: 25
aaggcttcca acttgcacac a                                            21

<210> SEQ ID NO 26
<211> LENGTH: 27
<212> TYPE: DNA
<213> ORGANISM: Mus musculus

<400> SEQUENCE: 26
caacagggtc aaacttatcc atacacg                                      27

<210> SEQ ID NO 27
<211> LENGTH: 5
<212> TYPE: PRT
<213> ORGANISM: Mus musculus

<400> SEQUENCE: 27

Arg Tyr Tyr Met Tyr
1               5

<210> SEQ ID NO 28
<211> LENGTH: 17
<212> TYPE: PRT

<213> ORGANISM: Mus musculus

<400> SEQUENCE: 28

Glu Ile Asn Pro Asn Asn Gly Gly Thr Lys Phe Asn Glu Lys Phe Lys
1               5                   10                  15

Asn

<210> SEQ ID NO 29
<211> LENGTH: 13
<212> TYPE: PRT
<213> ORGANISM: Mus musculus

<400> SEQUENCE: 29

Glu Asp Asp Tyr Asp Gly Thr Pro Phe Ala Met Asp Tyr
1               5                   10

<210> SEQ ID NO 30
<211> LENGTH: 11
<212> TYPE: PRT
<213> ORGANISM: Mus musculus

<400> SEQUENCE: 30

His Ala Ser Gln Asn Ile Asn Val Trp Leu Ser
1               5                   10

<210> SEQ ID NO 31
<211> LENGTH: 7
<212> TYPE: PRT
<213> ORGANISM: Mus musculus

<400> SEQUENCE: 31

Lys Ala Ser Asn Leu His Thr
1               5

<210> SEQ ID NO 32
<211> LENGTH: 9
<212> TYPE: PRT
<213> ORGANISM: Mus musculus

<400> SEQUENCE: 32

Gln Gln Gly Gln Thr Tyr Pro Tyr Thr
1               5

<210> SEQ ID NO 33
<211> LENGTH: 423
<212> TYPE: DNA
<213> ORGANISM: Mus musculus

<400> SEQUENCE: 33
atgggatgga gctatatcat cctcttttg gtagcaacag caacaggtgt ccactcccag      60
gtccaactgc agcagtctgg ggctgaactg gtgaagcctg ggcttcagt gaagttgtcc     120 tgcaaggctt ctggctacat cttcaccaga tactatatgt attgggtgaa gcagaggcct    180
ggacaaggcc ttgagtggat tggagagatt aatcctaaca atggtggtac taagttcaat    240
gagaagttca agaacaaggc cacactgact gtagacaaat tttccagcac agcatacatg    300
caactcagga gcctgacatc tgaggactct gcggtctatt attgttcaag agaggatgat    360
tacgacggga ccccctttgc tatggactac tggggtcaag gaacctcagt caccgtctcc    420
tca                                                                    423

<210> SEQ ID NO 34

```
<211> LENGTH: 141
<212> TYPE: PRT
<213> ORGANISM: Mus musculus

<400> SEQUENCE: 34

Met Gly Trp Ser Tyr Ile Ile Leu Phe Leu Val Ala Thr Ala Thr Gly
1               5                   10                  15

Val His Ser Gln Val Gln Leu Gln Gln Ser Gly Ala Glu Leu Val Lys
            20                  25                  30

Pro Gly Ala Ser Val Lys Leu Ser Cys Lys Ala Ser Gly Tyr Ile Phe
        35                  40                  45

Thr Arg Tyr Tyr Met Tyr Trp Val Lys Gln Arg Pro Gly Gln Gly Leu
    50                  55                  60

Glu Trp Ile Gly Glu Ile Asn Pro Asn Asn Gly Gly Thr Lys Phe Asn
65                  70                  75                  80

Glu Lys Phe Lys Asn Lys Ala Thr Leu Thr Val Asp Lys Phe Ser Ser
                85                  90                  95

Thr Ala Tyr Met Gln Leu Arg Ser Leu Thr Ser Glu Asp Ser Ala Val
            100                 105                 110

Tyr Tyr Cys Ser Arg Glu Asp Asp Tyr Asp Gly Thr Pro Phe Ala Met
        115                 120                 125

Asp Tyr Trp Gly Gln Gly Thr Ser Val Thr Val Ser Ser
    130                 135                 140

<210> SEQ ID NO 35
<211> LENGTH: 381
<212> TYPE: DNA
<213> ORGANISM: Mus musculus

<400> SEQUENCE: 35
atgagggtcc ttgctgagct cctggggctg ctgctgttct gcttttagg tgtgagatgt       60 gacatccaga tgaaccagtc tccatccagt ctgtctgcat cccttggaga cacaattacc     120
atcacttgcc atgccagtca gaacattaat gtttggttaa gctggtacca gcagaaacca     180
ggaaatattc ctaaactatt gatctataag gcttccaact tgcacacagg cgtcccatca     240
agatttactg gcagtggatc tggaacaggt ttcactatta ccatcagcag cctgcagcct     300
gaagacattg ccacttacta ctgtcaacag ggtcaaactt atccatacac gttcggaggg     360
gggaccaagt tggaaataaa g                                                381

<210> SEQ ID NO 36
<211> LENGTH: 127
<212> TYPE: PRT
<213> ORGANISM: Mus musculus

<400> SEQUENCE: 36

Met Arg Val Leu Ala Glu Leu Leu Gly Leu Leu Leu Phe Cys Phe Leu
1               5                   10                  15

Gly Val Arg Cys Asp Ile Gln Met Asn Gln Ser Pro Ser Ser Leu Ser
            20                  25                  30

Ala Ser Leu Gly Asp Thr Ile Thr Ile Thr Cys His Ala Ser Gln Asn
        35                  40                  45

Ile Asn Val Trp Leu Ser Trp Tyr Gln Gln Lys Pro Gly Asn Ile Pro
    50                  55                  60

Lys Leu Leu Ile Tyr Lys Ala Ser Asn Leu His Thr Gly Val Pro Ser
65                  70                  75                  80

Arg Phe Thr Gly Ser Gly Ser Gly Thr Gly Phe Thr Leu Thr Ile Ser
```

```
                    85                  90                  95
Ser Leu Gln Pro Glu Asp Ile Ala Thr Tyr Tyr Cys Gln Gln Gly Gln
                100                 105                 110

Thr Tyr Pro Tyr Thr Phe Gly Gly Gly Thr Lys Leu Glu Ile Lys
            115                 120                 125

<210> SEQ ID NO 37
<211> LENGTH: 366
<212> TYPE: DNA
<213> ORGANISM: Mus musculus

<400> SEQUENCE: 37
caggtccaac tgcagcagtc tggggctgaa ctggtgaagc ctggggcttc agtgaagttg      60
tcctgcaagg cttctggcta catcttcacc agatactata tgtattgggt gaagcagagg     120
cctggacaag gccttgagtg gattggagag attaatccta acaatggtgg tactaagttc     180
aatgagaagt tcaagaacaa ggccacactg actgtagaca atttttccag cacagcatac     240
atgcaactca ggagcctgac atctgaggac tctgcggtct attattgttc aagagaggat     300
gattacgacg ggaccccctt tgctatggac tactggggtc aaggaacctc agtcaccgtc     360
tcctca                                                                366

<210> SEQ ID NO 38
<211> LENGTH: 122
<212> TYPE: PRT
<213> ORGANISM: Mus musculus

<400> SEQUENCE: 38

Gln Val Gln Leu Gln Gln Ser Gly Ala Glu Leu Val Lys Pro Gly Ala
1               5                   10                  15

Ser Val Lys Leu Ser Cys Lys Ala Ser Gly Tyr Ile Phe Thr Arg Tyr
            20                  25                  30

Tyr Met Tyr Trp Val Lys Gln Arg Pro Gly Gln Gly Leu Glu Trp Ile
        35                  40                  45

Gly Glu Ile Asn Pro Asn Asn Gly Gly Thr Lys Phe Asn Glu Lys Phe
    50                  55                  60

Lys Asn Lys Ala Thr Leu Thr Val Asp Lys Phe Ser Ser Thr Ala Tyr
65                  70                  75                  80

Met Gln Leu Arg Ser Leu Thr Ser Glu Asp Ser Ala Val Tyr Tyr Cys
                85                  90                  95

Ser Arg Glu Asp Asp Tyr Asp Gly Thr Pro Phe Ala Met Asp Tyr Trp
                100                 105                 110

Gly Gln Gly Thr Ser Val Thr Val Ser Ser
            115                 120

<210> SEQ ID NO 39
<211> LENGTH: 321
<212> TYPE: DNA
<213> ORGANISM: Mus musculus

<400> SEQUENCE: 39
gacatccaga tgaaccagtc tccatccagt ctgtctgcat cccttggaga cacaattacc      60
atcacttgcc atgccagtca gaacattaat gtttggttaa gctggtacca gcagaaacca     120
ggaaatattc ctaaactatt gatctataag gcttccaact tgcacacagg cgtcccatca     180
agatttactg gcagtggatc tggaacaggt ttcacattaa ccatcagcag cctgcagcct     240
gaagacattg ccacttacta ctgtcaacag ggtcaaactt atccatacac gttcggaggg     300
```
gggaccaagt tggaaataaa g                                        321

<210> SEQ ID NO 40
<211> LENGTH: 107
<212> TYPE: PRT
<213> ORGANISM: Mus musculus

<400> SEQUENCE: 40

Asp Ile Gln Met Asn Gln Ser Pro Ser Ser Leu Ser Ala Ser Leu Gly
1               5                   10                  15

Asp Thr Ile Thr Ile Thr Cys His Ala Ser Gln Asn Ile Asn Val Trp
            20                  25                  30

Leu Ser Trp Tyr Gln Gln Lys Pro Gly Asn Ile Pro Lys Leu Leu Ile
        35                  40                  45

Tyr Lys Ala Ser Asn Leu His Thr Gly Val Pro Ser Arg Phe Thr Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Gly Gln Thr Tyr Pro Tyr
                85                  90                  95

Thr Phe Gly Gly Gly Thr Lys Leu Glu Ile Lys
            100                 105

<210> SEQ ID NO 41
<211> LENGTH: 15
<212> TYPE: DNA
<213> ORGANISM: Mus musculus

<400> SEQUENCE: 41
ggcttcgcca ttaac                                               15

<210> SEQ ID NO 42
<211> LENGTH: 51
<212> TYPE: DNA
<213> ORGANISM: Mus musculus

<400> SEQUENCE: 42
cttatttatc cttacaatgg tggtactacc tacagccaga ggttcaaggg c        51

<210> SEQ ID NO 43
<211> LENGTH: 30
<212> TYPE: DNA
<213> ORGANISM: Mus musculus

<400> SEQUENCE: 43
cggcgggatg gttactcctg gtttgcttac                               30

<210> SEQ ID NO 44
<211> LENGTH: 45
<212> TYPE: DNA
<213> ORGANISM: Mus musculus

<400> SEQUENCE: 44
agagccagcg aaagtgttga gaattatggc attattttta tgaac              45

<210> SEQ ID NO 45
<211> LENGTH: 21
<212> TYPE: DNA
<213> ORGANISM: Mus musculus

<400> SEQUENCE: 45

```
tctgcatcca accaaggatc c                                          21
```

<210> SEQ ID NO 46
<211> LENGTH: 27
<212> TYPE: DNA
<213> ORGANISM: Mus musculus

<400> SEQUENCE: 46

```
cagcaaagta aggaggctcc gttcacg                                    27
```

<210> SEQ ID NO 47
<211> LENGTH: 5
<212> TYPE: PRT
<213> ORGANISM: Mus musculus

<400> SEQUENCE: 47

Gly Phe Ala Ile Asn
1               5

<210> SEQ ID NO 48
<211> LENGTH: 17
<212> TYPE: PRT
<213> ORGANISM: Mus musculus

<400> SEQUENCE: 48

Leu Ile Tyr Pro Tyr Asn Gly Gly Thr Thr Tyr Ser Gln Arg Phe Lys
1               5                   10                  15

Gly

<210> SEQ ID NO 49
<211> LENGTH: 10
<212> TYPE: PRT
<213> ORGANISM: Mus musculus

<400> SEQUENCE: 49

Arg Arg Asp Gly Tyr Ser Trp Phe Ala Tyr
1               5                   10

<210> SEQ ID NO 50
<211> LENGTH: 15
<212> TYPE: PRT
<213> ORGANISM: Mus musculus

<400> SEQUENCE: 50

Arg Ala Ser Glu Ser Val Glu Asn Tyr Gly Ile Ile Phe Met Asn
1               5                   10                  15

<210> SEQ ID NO 51
<211> LENGTH: 7
<212> TYPE: PRT
<213> ORGANISM: Mus musculus

<400> SEQUENCE: 51

Ser Ala Ser Asn Gln Gly Ser
1               5

<210> SEQ ID NO 52
<211> LENGTH: 9
<212> TYPE: PRT
<213> ORGANISM: Mus musculus

<400> SEQUENCE: 52

Gln Gln Ser Lys Glu Ala Pro Phe Thr

<210> SEQ ID NO 53
<211> LENGTH: 414
<212> TYPE: DNA
<213> ORGANISM: Mus musculus

<400> SEQUENCE: 53

```
atgggatgga gctggatctt tctcttcctc ctgtcaggaa ctgcaggtgt ccactctgag    60
gtccagttgc aacagtctgg acctgagctg gtgaagcctg gagcttcaat gaagatatcc   120
tgcaaggctt ctggttactc attcactggc ttcgccatta actgggtgaa acagagccat   180
ggacagaacc ttgagtggat tgggcttatt tatccttaca tggtggtac tacctacagc   240
cagaggttca aggcaaggc cacattaact gtagacaagt catccaccac agcctacatg   300
gagctcctca gtctgacatc tgaagactct gcagtctatt actgtgcaag acggcgggat   360
ggttactcct ggtttgctta ctggggccaa gggactctgg tcactgtctc tgca         414
```

<210> SEQ ID NO 54
<211> LENGTH: 138
<212> TYPE: PRT
<213> ORGANISM: Mus musculus

<400> SEQUENCE: 54

Met Gly Trp Ser Trp Ile Phe Leu Phe Leu Leu Ser Gly Thr Ala Gly
1               5                   10                  15

Val His Ser Glu Val Gln Leu Gln Gln Ser Gly Pro Glu Leu Val Lys
            20                  25                  30

Pro Gly Ala Ser Met Lys Ile Ser Cys Lys Ala Ser Gly Tyr Ser Phe
        35                  40                  45

Thr Gly Phe Ala Ile Asn Trp Val Lys Gln Ser His Gly Gln Asn Leu
    50                  55                  60

Glu Trp Ile Gly Leu Ile Tyr Pro Tyr Asn Gly Gly Thr Thr Tyr Ser
65                  70                  75                  80

Gln Arg Phe Lys Gly Lys Ala Thr Leu Thr Val Asp Lys Ser Ser Thr
                85                  90                  95

Thr Ala Tyr Met Glu Leu Leu Ser Leu Thr Ser Glu Asp Ser Ala Val
            100                 105                 110

Tyr Tyr Cys Ala Arg Arg Arg Asp Gly Tyr Ser Trp Phe Ala Tyr Trp
        115                 120                 125

Gly Gln Gly Thr Leu Val Thr Val Ser Ala
    130                 135

<210> SEQ ID NO 55
<211> LENGTH: 393
<212> TYPE: DNA
<213> ORGANISM: Mus musculus

<400> SEQUENCE: 55

```
atggagaaag acacactcct gctatggggc ctgcttctct gggttccagc ttccacaggt    60
gacattgtgc tgacccaatc tccagcttct ttggctgtgt ctctagggca gagggccacc   120
atctcctgca gagccagcga aagtgttgag aattatggca ttatttttat gaactggttc   180
caacagaaac caggacagcc acccaaactc ctcatctttt ctgcatccaa ccaaggatcc   240
ggggtccctg ccaggtttaa tggcagtggg tctgggacag acttcagcct caacatccat   300
cctatggagg aggatgatac tgcaatgtat ttctgtcagc aaagtaagga ggctccgttc   360
```
acgttcggag gggggaccaa gctggaaata aaa                                    393

<210> SEQ ID NO 56
<211> LENGTH: 131
<212> TYPE: PRT
<213> ORGANISM: Mus musculus

<400> SEQUENCE: 56

Met Glu Lys Asp Thr Leu Leu Leu Trp Gly Leu Leu Leu Trp Val Pro
1               5                   10                  15

Ala Ser Thr Gly Asp Ile Val Leu Thr Gln Ser Pro Ala Ser Leu Ala
            20                  25                  30

Val Ser Leu Gly Gln Arg Ala Thr Ile Ser Cys Arg Ala Ser Glu Ser
        35                  40                  45

Val Glu Asn Tyr Gly Ile Ile Phe Met Asn Trp Phe Gln Gln Lys Pro
    50                  55                  60

Gly Gln Pro Pro Lys Leu Leu Ile Phe Ser Ala Ser Asn Gln Gly Ser
65                  70                  75                  80

Gly Val Pro Ala Arg Phe Asn Gly Ser Gly Ser Gly Thr Asp Phe Ser
                85                  90                  95

Leu Asn Ile His Pro Met Glu Glu Asp Asp Thr Ala Met Tyr Phe Cys
            100                 105                 110

Gln Gln Ser Lys Glu Ala Pro Phe Thr Phe Gly Gly Gly Thr Lys Leu
        115                 120                 125

Glu Ile Lys
    130

<210> SEQ ID NO 57
<211> LENGTH: 357
<212> TYPE: DNA
<213> ORGANISM: Mus musculus

<400> SEQUENCE: 57
gaggtccagt tgcaacagtc tggacctgag ctggtgaagc ctggagcttc aatgaagata    60
tcctgcaagg cttctggtta ctcattcact ggcttcgcca ttaactgggt gaaacagagc    120
catggacaga accttgagtg gattgggctt atttatcctt acaatggtgg tactacctac    180
agccagaggt tcaagggcaa ggccacatta actgtagaca agtcatccac cacagcctac    240
atggagctcc tcagtctgac atctgaagac tctgcagtct attactgtgc aagacggcgg    300
gatggttact cctggtttgc ttactggggc caagggactc tggtcactgt ctctgca      357

<210> SEQ ID NO 58
<211> LENGTH: 119
<212> TYPE: PRT
<213> ORGANISM: Mus musculus

<400> SEQUENCE: 58

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Phe
            20                  25                  30

Ala Ile Asn Trp Val Lys Gln Ser His Gly Gln Asn Leu Glu Trp Ile
        35                  40                  45

Gly Leu Ile Tyr Pro Tyr Asn Gly Gly Thr Thr Tyr Ser Gln Arg Phe
    50                  55                  60

Lys Gly Lys Ala Thr Leu Thr Val Asp Lys Ser Ser Thr Thr Ala Tyr
65                  70                  75                  80

```
Met Glu Leu Leu Ser Leu Thr Ser Glu Asp Ser Ala Val Tyr Tyr Cys
                    85                  90                  95
Ala Arg Arg Arg Asp Gly Tyr Ser Trp Phe Ala Tyr Trp Gly Gln Gly
                100                 105                 110
Thr Leu Val Thr Val Ser Ala
            115

<210> SEQ ID NO 59
<211> LENGTH: 333
<212> TYPE: DNA
<213> ORGANISM: Mus musculus

<400> SEQUENCE: 59
gacattgtgc tgacccaatc tccagcttct ttggctgtgt ctctagggca gagggccacc      60
atctcctgca gagccagcga aagtgttgag aattatggca ttatttttat gaactggttc    120
caacagaaac caggacagcc acccaaactc ctcatctttt ctgcatccaa ccaaggatcc    180
ggggtccctg ccaggtttaa tggcagtggg tctgggacag acttcagcct caacatccat    240
cctatggagg aggatgatac tgcaatgtat ttctgtcagc aaagtaagga ggctccgttc    300
acgttcggag gggggaccaa gctggaaata aaa                                  333

<210> SEQ ID NO 60
<211> LENGTH: 111
<212> TYPE: PRT
<213> ORGANISM: Mus musculus

<400> SEQUENCE: 60

Asp Ile Val Leu Thr Gln Ser Pro Ala Ser Leu Ala Val Ser Leu Gly
1               5                   10                  15
Gln Arg Ala Thr Ile Ser Cys Arg Ala Ser Glu Ser Val Glu Asn Tyr
                20                  25                  30
Gly Ile Ile Phe Met Asn Trp Phe Gln Gln Lys Pro Gly Gln Pro Pro
            35                  40                  45
Lys Leu Leu Ile Phe Ser Ala Ser Asn Gln Gly Ser Gly Val Pro Ala
        50                  55                  60
Arg Phe Asn Gly Ser Gly Ser Gly Thr Asp Phe Ser Leu Asn Ile His
65                  70                  75                  80
Pro Met Glu Glu Asp Asp Thr Ala Met Tyr Phe Cys Gln Gln Ser Lys
                85                  90                  95
Glu Ala Pro Phe Thr Phe Gly Gly Gly Thr Lys Leu Glu Ile Lys
                100                 105                 110
```